(12) United States Patent
Moussy et al.

(10) Patent No.: US 10,570,122 B2
(45) Date of Patent: Feb. 25, 2020

(54) COMPOUNDS WITH ANTI-TUMORAL ACTIVITY

(71) Applicant: AB Science, Paris (FR)

(72) Inventors: Alain Moussy, Paris (FR); Abdellah Benjahad, Champigny-sur-Marne (FR); Didier Pez, Niévroz (FR); Franck Sandrinelli, Balan (FR); Jason Martin, L'Haÿ-les-Roses (FR); Willy Picoul, Lyons (FR); Emmanuel Chevenier, Limours (FR)

(73) Assignee: AB Science, Paris (FR)

( * ) Notice: Subject to any disclaimer, the term of this patent is extended or adjusted under 35 U.S.C. 154(b) by 0 days.

(21) Appl. No.: 15/548,451

(22) PCT Filed: Feb. 5, 2016

(86) PCT No.: PCT/EP2016/052523
§ 371 (c)(1),
(2) Date: Aug. 3, 2017

(87) PCT Pub. No.: WO2016/124747
PCT Pub. Date: Aug. 11, 2016

(65) Prior Publication Data
US 2018/0079747 A1    Mar. 22, 2018

(30) Foreign Application Priority Data

Feb. 5, 2015   (EP) ..................... 15154028

(51) Int. Cl.
| | | |
|---|---|---|
| *C07D 413/10* | (2006.01) | |
| *C07D 413/14* | (2006.01) | |
| *C07D 417/10* | (2006.01) | |
| *C07D 417/14* | (2006.01) | |
| *A61K 31/422* | (2006.01) | |
| *A61K 31/427* | (2006.01) | |
| *A61K 31/4439* | (2006.01) | |
| *A61K 31/5377* | (2006.01) | |

(52) U.S. Cl.
CPC .......... *C07D 413/10* (2013.01); *A61K 31/422* (2013.01); *A61K 31/427* (2013.01); *A61K 31/4439* (2013.01); *A61K 31/5377* (2013.01); *C07D 413/14* (2013.01); *C07D 417/10* (2013.01); *C07D 417/14* (2013.01)

(58) Field of Classification Search
CPC .. C07D 413/10; C07D 413/14; C07D 417/10; C07D 417/14; A61K 31/422; A61K 31/427; A61K 31/4439; A61K 31/5377
See application file for complete search history.

(56) References Cited

U.S. PATENT DOCUMENTS

| | | | | |
|---|---|---|---|---|
| 6,552,029 | B1* | 4/2003 | Davis ............... | C07D 401/04 514/275 |
| 7,781,442 | B2* | 8/2010 | Cheng .............. | C07D 277/42 514/269 |
| 7,799,808 | B2* | 9/2010 | Cheng .............. | C07D 277/42 514/256 |
| 8,017,629 | B2* | 9/2011 | Cheng .............. | C07D 277/42 514/256 |
| 8,088,806 | B2* | 1/2012 | Zhang .............. | C07D 277/38 514/342 |
| 8,119,680 | B2* | 2/2012 | Cheng .............. | C07D 277/42 514/399 |
| 8,546,400 | B2* | 10/2013 | Desai ............... | C07D 413/10 514/252.19 |
| 8,551,992 | B2* | 10/2013 | Desai ............... | C07D 413/10 514/236.8 |
| 8,835,451 | B2* | 9/2014 | Serrano-Wu ...... | C07D 213/74 514/277 |
| 8,865,709 | B2* | 10/2014 | Desai ............... | C07D 413/10 435/375 |

(Continued)

FOREIGN PATENT DOCUMENTS

| | | | |
|---|---|---|---|
| JP | 2001503047 | A | 3/2001 |
| JP | 2006347980 | A * | 12/2006 |

(Continued)

OTHER PUBLICATIONS

CAS Abstract RN 1346834-62-5 (2011) (Year: 2011).*

(Continued)

*Primary Examiner* — Alexander R Pagano
(74) *Attorney, Agent, or Firm* — Klarquist Sparkman, LLP

(57) ABSTRACT

The present invention relates to compounds of general formula (I).

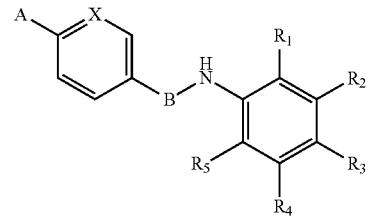

wherein A represents an optionally substituted heterocycle group, B represents an aryl or heteroaryl group and wherein X, R1, R2, R3, R4 and R5 are as defined in the description. Compounds of formula (I) are useful to destroy, inhibit, or prevent the growth or spread of cells, especially malignant cells, into surrounding tissues implicated in a variety of human and animal diseases.

19 Claims, No Drawings

(56) References Cited

U.S. PATENT DOCUMENTS

| | | | | |
|---|---|---|---|---|
| 8,871,460 B2* | 10/2014 | Kounnas | ............ | G01N 33/6896 435/23 |
| 8,912,208 B2* | 12/2014 | Serrano-Wu | ......... | C07D 213/74 514/277 |
| 8,946,266 B2* | 2/2015 | Wu | ...................... | C07D 233/60 514/340 |
| 2004/0110810 A1 | 6/2004 | Ciufolini | .............. | C07D 277/42 514/370 |
| 2005/0070538 A1* | 3/2005 | Cheng | ................. | C07D 277/42 514/241 |
| 2007/0142390 A1* | 6/2007 | Moussy | ............... | C07D 263/48 514/252.05 |
| 2008/0207572 A1* | 8/2008 | Moussy | ............. | A61K 31/4439 514/171 |
| 2008/0242704 A1* | 10/2008 | Grierson | .............. | C07D 263/46 514/340 |
| 2008/0275054 A1* | 11/2008 | Holzer | ................. | C07D 487/04 514/252.16 |
| 2010/0204187 A1* | 8/2010 | Salas Solana | ....... | C07D 473/04 514/157 |
| 2011/0201620 A1* | 8/2011 | Ciufolini | .............. | C07D 277/42 514/253.1 |
| 2012/0129843 A1* | 5/2012 | Zhang | .................. | C07D 417/04 514/218 |
| 2012/0302569 A1* | 11/2012 | Jackson | ............... | C07D 277/42 514/236.8 |
| 2012/0302578 A1* | 11/2012 | Desai | .................... | C07D 413/10 514/252.19 |
| 2013/0035331 A1* | 2/2013 | Moussy | ............... | C07D 413/12 514/227.8 |
| 2013/0165440 A1* | 6/2013 | Anand | ................. | C07D 217/22 514/234.5 |
| 2014/0179698 A1* | 6/2014 | Benjahad | ............. | C07D 413/14 514/235.8 |
| 2015/0045353 A1* | 2/2015 | Comer | ................. | A61K 9/2054 514/227.8 |
| 2018/0179195 A1* | 6/2018 | Benjahad | ............. | C07D 413/14 |
| 2019/0055230 A1* | 2/2019 | Moussy | ............... | A61K 31/506 |

FOREIGN PATENT DOCUMENTS

| | | | | |
|---|---|---|---|---|
| JP | 2013531055 A | 1/2012 | | |
| WO | 9818782 A1 | 5/1998 | | |
| WO | WO00/33841 | 6/2000 | | |
| WO | WO2004/110350 | 12/2004 | | |
| WO | WO-2004110350 A2 * | 12/2004 | ............ | C07D 277/42 |
| WO | 2006010637 A2 | 2/2006 | | |
| WO | 2006021458 A2 | 3/2006 | | |
| WO | WO2007/118903 | 10/2007 | | |
| WO | 2007131953 A1 | 11/2007 | | |
| WO | WO2007/126957 | 11/2007 | | |
| WO | WO2008/103500 | 8/2008 | | |
| WO | WO2008/139161 | 11/2008 | | |
| WO | WO2010/005841 | 1/2010 | | |
| WO | WO2011/001931 | 1/2011 | | |
| WO | WO2011/006903 | 1/2011 | | |
| WO | WO-2011001931 A1 * | 1/2011 | ........... | C07D 413/10 |
| WO | WO-2011006903 A1 * | 1/2011 | ........... | C07D 233/60 |
| WO | 2012010826 A1 | 1/2012 | | |
| WO | 2012037132 A1 | 3/2012 | | |
| WO | WO-2012037132 A1 * | 3/2012 | ........... | C07D 217/22 |
| WO | WO2012/068210 | 5/2012 | | |
| WO | WO2012/162461 | 11/2012 | | |
| WO | WO-2012162461 A1 * | 11/2012 | ........... | C07D 277/42 |
| WO | WO2012/166463 | 12/2012 | | |
| WO | WO2013/014170 | 1/2013 | | |
| WO | WO-2015021191 A1 * | 2/2015 | | |

OTHER PUBLICATIONS

CAS Index of Compound Registry No. 810665-30-6 (2005).*
R. Rishikesan et al., 52 Journal of Heterocyclic Chemistry,1321-1330 (Published online Jul. 17, 2014).*
CAS Communication Regarding RN 810665-30-6 (Oct. 11, 2018).*
CAS Abstract of JP 2006347980 (2006) (Year: 2006).*
English-Language Machine Translation JP 2006347980 (2006) (Year: 2006).*
A. Velter et al., 24 Bioorganic & Medicinal Chemistry Letters, 5805-5813 (2014) (Year: 2014).*
Al-Azzawi et al., "Synthesis and antimicrobial activity of new succinimides bearing different heterocycles," *International Journal of Research in Pharmacy and Chemistry*, 4(4):755-762 (2014).
Dawood et al., "Microwave-Assisted Synthesis of 2-Substituted 4-Biarylyl-1,3-thiazoles by Carbon-Carbon Cross-Coupling in Water," (Abstract) *Synthesis*, 2010(6):1030-1038 (Mar. 2010).
Deohate et al., "Synthesis, characterization and antimicrobial study of substituted bis-[1,3,4]-oxadiazole, bis-[1,3,4]-thiadiazole and bis-[1,2,4]-triazole derivatives," *Journal of the Indian Chemical Society*, 85(11):1153-1158 (Nov. 2008).
International Search Report and Written Opinion for PCT/EP2016/052523 dated Apr. 18, 2016.
Joshi et al, "Synthesis of some substituted pyrazoles as possible antibacterial agents," (Abstract) *Journal of the Indian Chemical Society*, 54(11):1081-1083 (1977).
Mane et al., "Synthesis of 2-aryl-3-[p-(2'-substituted-aminothiazol-4'-yl)phenyl]-4-thiazolidinones," (Abstract) *Indian Journal of Chemistry, Section B: Organic Chemistry Including Medicinal Chemistry*, 22B(1):81-82 (1983).
Bombrun et al., Tetrahedron Letters, Jul. 27, 2005, No. 36, pp. 6033-6036.
Frey et al., Tetrahedron Letters., Aug. 16, 2001, No. 39, p. 6815-6818.
Ohta et al., The Journal of Organic Chemistry, Sep. 30, 2009, vol. 74, pp. 8143-8153.
Van Leusen et al., Tetrahedron Letters, May 1972, No. 23, pp. 2369-2372.
Zhao et al., Tetrahedron Letters, Feb. 27, 2001, No. 42, pp. 2101-2102.

* cited by examiner

COMPOUNDS WITH ANTI-TUMORAL ACTIVITY

CROSS REFERENCE TO RELATED APPLICATIONS

This is the U.S. National Stage of International Application No. PCT/EP2016/052523, filed Feb. 5, 2016, which was published in English under PCT Article 21(2), which in turn claims the benefit of European Patent Application No, 15154028.3, filed Feb. 5, 2015, which is incorporated herein in its entirety.

FIELD OF INVENTION

The present invention relates to compounds of formula (I), or pharmaceutically acceptable salts thereof, that destroy, inhibit, or prevent the growth or spread of cells, especially malignant cells, into surrounding tissues implicated in a variety of human and animal diseases.

Especially, the invention relates to compounds that are useful in the treatment of diseases related to cell proliferation, such as hematopoietic cancers including lymphoma, leukemia and multiple myeloma, solid cancers including head and neck cancer, melanoma, kidney carcinoma, stomach carcinoma, liver carcinoma, colorectal carcinoma, pancreas carcinoma, lung carcinoma, neuronal carcinoma, bone carcinoma, breast carcinoma, ovary carcinoma, and prostate carcinoma.

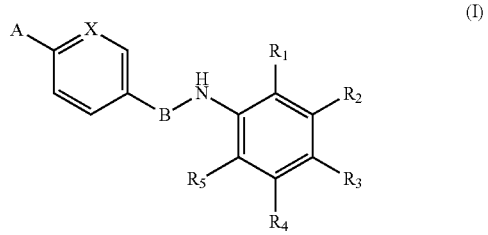

(I)

BACKGROUND OF INVENTION

Cancer is a generic term for a large group of diseases that can affect any part of the body. One defining feature of cancer is the rapid creation of abnormal cells that grow beyond their usual boundaries, and which can then invade adjoining parts of the body and spread to other organs, the latter process is referred to as metastasizing. Metastases are the major cause of death from cancer.

Cancers figure among the leading causes of morbidity and mortality worldwide, with approximately 14 million new cases and 8.2 million cancer related deaths in 2012. The most common causes of cancer death are cancers of lung (1.59 million deaths), liver (745 000 deaths), stomach (723 000 deaths), colorectal (694 000 deaths), breast (521 000 deaths), esophageal cancer (400 000 deaths). Among men, the 5 most common sites of cancer diagnosed in 2012 were lung, prostate, colorectal, stomach, and liver cancer. Among women the 5 most common sites diagnosed were breast, colorectal, lung, cervix, and stomach cancer.

The number of new cases is expected to rise by about 70% over the next two decades (World Cancer Report 2014, WHO).

Despite extraordinary advances in our understanding of the biology that underlies the development and progression of cancer as well as potential molecular targets for its treatment, more than 90% of all new oncology drugs that enter clinical development do not obtain marketing approval. Many drugs fail in late stages of development—often in Phase III trials—because of inadequate activity, lack of strategies for combating resistance to these drugs, unexpected safety issues or difficulties in determining efficacy because of reasons that include confounded outcomes of clinical trials. Moreover, an increased understanding of cancer biology has shown that cancers are heterogeneous diseases, which suggests that there is a high likelihood that effective cancer treatments will need to address patient-specific molecular defects and aspects of the tumor microenvironment.

The widespread occurrence of cancer and the high degree of heterogeneity of this disease underscores the need for improved anticancer regimens for the treatment of malignancy. The recent use of large panel of cancer cell lines agents is becoming an important tool for the discovery and evaluation of potential new anti-cancer. Indeed, large panel of tumor-derived cell lines may recapitulate the genotype-response relationship of new therapeutic agents and may be of utmost interest.

The present invention provides new compounds of formula (I) for the treatment of diseases related to cell proliferation, such as hematopoietic cancers or solid cancers.

Compounds of the invention have an anti-tumoral activity on a very large panel of cancer cell lines.

Compounds of formula (I) comprise a 6-membered aryl or heteroaryl moiety para-substituted by A and B moieties. Compounds comprising a 6-membered aryl or heteroaryl moiety meta-substituted by heteroaryl and heterocycle groups are disclosed in WO2013/014170. Compounds of WO2013/014170 are tyrosine kinases inhibitors and may be used for the treatment of proliferative diseases. Surprisingly, compounds of formula (I) the invention are not tyrosine kinase inhibitors, while having anti-proliferative properties. Therefore, compounds of the invention offer a new route of treatment of diseases related to cell proliferation.

SUMMARY

The present invention relates to a compound of formula (I):

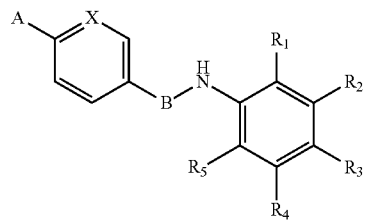

wherein A, B, X, R1, R2, R3, R4 and R5 are as defined below.

According to one embodiment, in compound of formula (I), B is a five member ring heteroaryl group.

According to one embodiment, B is not selected from 1,2 diazinyl, triazolopyridinyl or triazolyl. According to one embodiment, if B is oxazolyl, A is not tetrazolyl or tetrahydropyridinyl. According to one embodiment, if B is thiazolyl, A is not imidazolyl, triazolyl, piperazinyl, pyrrolidinyl, piperidinyl or 1,4-oxazinyl.

According to one embodiment, in compound of formula (I), X is CH and A is 2-oxoimidazolidinyl or pyrazolyl group.

According to one embodiment, in the compound of the invention, R3 is a hydrogen.

According to one embodiment, a compound of formula (I) is of formula (II) as defined below.

According to one embodiment, a compound of formula (I) is of formula (III) as defined below.

According to one embodiment, in the compound of the invention, R1 is methyl, R2, R3 and R5 are hydrogen and R4 is —CH$_2$OC$_2$H$_5$.

According to one embodiment, the compound of the invention is selected from:

(5-Methoxy-2-methyl-phenyl)-[5-(6-pyrazol-1-yl-pyridin-3-yl)-oxazol-2-yl]-amine;
(5-Ethoxymethyl-2-methyl-phenyl)-[5-(3-methoxy-4-pyrazol-1-yl-phenyl)-oxazol-2-yl]-amine;
1-{4-[2-(5-Ethoxymethyl-(2-methyl-phenylamino))-thiazol-4-yl]-phenyl}-imidazolidin-2-one;
(5-Ethoxymethyl-2-methyl-phenyl)-[5-(4-pyrazol-1-yl-phenyl)-thiazol-2-yl]-amine;
4-Methyl-N-(2-morpholin-4-yl-ethyl)-3-[5-(4-pyrazol-1-yl-phenyl)-oxazol-2-ylamino]-benzamide;
1-{4-[2-(5-Ethoxymethyl-(2-methyl-phenylamino))-oxazol-5-yl]-phenyl}-imidazolidin-2-one;
(5-Ethoxymethyl-2-methyl-phenyl)-[5-(6-pyrazol-1-yl-pyridin-3-yl)-oxazol-2-yl]-amine;
1-{4-[5-(5-Ethoxymethyl-(2-methyl-phenylamino))-[1,3,4]oxadiazol-2-yl]-phenyl}-imidazolidin-2-one;
(5-Ethoxymethyl-2-methyl-phenyl)-[5-(4-pyrazol-1-yl-phenyl)-[1,3,4]oxadiazol-2-yl]-amine;
1-{4-[5-(5-Ethoxymethyl-(2-methyl-phenylamino))-[1,2,4]thiadiazol-3-yl]-phenyl}-imidazolidin-2-one;
(5-Methoxy-2-methyl-phenyl)-[5-(4-pyrazol-1-yl-phenyl)-thiazol-2-yl]-amine;
1-{4-[2-(5-Methoxy-2-methyl-phenylamino)-thiazol-5-yl]-phenyl}-imidazolidin-2-one;
1-{4-[2-(5-Ethoxymethyl-(2-methyl-phenylamino))-thiazol-5-yl]-phenyl}-imidazolidin-2-one;
(5-Ethoxymethyl-2-methyl-phenyl)-[4-(4-pyrazol-1-yl-phenyl)-thiazol-2-yl]-amine;
{4-Methyl-3-[4-(4-pyrazol-1-yl-phenyl)-thiazol-2-ylamino]-phenyl}-methanol;
1-{4-[2-(3-Ethoxymethyl-(5-methyl-phenylamino))-thiazol-4-yl]-phenyl}-imidazolidin-2-one;
1-{4-[2-(3-Ethoxymethyl-(5-methyl-phenylamino))-oxazol-5-yl]-phenyl}-imidazolidin-2-one;
(3-Ethoxymethyl-phenyl)-[5-(4-pyrazol-1-yl-phenyl)-oxazol-2-yl]-amine;
(3-Ethoxymethyl-5-methyl-phenyl)-[5-(4-pyrazol-1-yl-phenyl)-oxazol-2-yl]-amine;
(3,5-Bis-(ethoxymethyl)-phenyl)-[5-(4-pyrazol-1-yl-phenyl)-oxazol-2-yl]-amine;
(5-Methoxy-2-methyl-phenyl)-[5-(4-pyrazol-1-yl-phenyl)-oxazol-2-yl]-amine;
[5-(2-Amino-ethoxymethyl)-2-methyl-phenyl]-[5-(4-pyrazol-1-yl-phenyl)-oxazol-2-yl]-amine;
N-(2-{4-Methyl-3-[5-(4-pyrazol-1-yl-phenyl)-oxazol-2-ylamino]-benzyloxy}-ethyl)-acetamide;
2-{4-Methyl-3-[5-(4-pyrazol-1-yl-phenyl)-oxazol-2-ylamino]-benzyloxy}-ethanol;
{4-Methyl-3-[5-(4-pyrazol-1-yl-phenyl)-oxazol-2-ylamino]-phenyl}-methanol;
{2-Methyl-5-[(2-morpholin-4-yl-ethylamino)-methyl]-phenyl}-[5-(4-pyrazol-1-yl-phenyl)-oxazol-2-yl]-amine;
[2-Methyl-5-(2-morpholin-4-yl-ethoxy)-phenyl]-[5-(4-pyrazol-1-yl-phenyl)-oxazol-2-yl]-amine;
[5-(2-Dimethylamino-ethoxy)-2-methyl-phenyl]-[5-(4-pyrazol-1-yl-phenyl)-oxazol-2-yl]-amine;
4,N-Dimethyl-3-[5-(4-pyrazol-1-yl-phenyl)-oxazol-2-ylamino]-benzamide;
4-Methyl-N-[2-(4-methyl-piperazin-1-yl)-ethyl]-3-[5-(4-pyrazol-1-yl-phenyl)-oxazol-2-ylamino]-benzamide;
(5-Ethoxymethyl-2-methyl-phenyl)-[5-(4-pyrazol-1-yl-phenyl)-oxazol-2-yl]-amine;
(5-Ethoxymethyl-2-methyl-phenyl)-[5-(4-[1,2,4]triazol-1-yl-phenyl)-oxazol-2-yl]-amine;
(5-Ethoxymethyl-2-methyl-phenyl)-[5-(4-[1,2,3]triazol-1-yl-phenyl)-oxazol-2-yl]-amine;
(5-Ethoxymethyl-2-methyl-phenyl)-[5-(4-[1,2,3]triazol-2-yl-phenyl)-oxazol-2-yl]-amine;
(5-Ethoxymethyl-2-methyl-phenyl)-[5-(4-imidazol-1-yl-phenyl)-oxazol-2-yl]-amine;
(5-Ethoxymethyl-2-methyl-phenyl)-[5-(4-thiazol-2-yl-phenyl)-oxazol-2-yl]-amine;
(5-Ethoxymethyl-2-methyl-phenyl)-{5-[4-(3-methyl-pyrazol-1-yl)-phenyl]-oxazol-2-yl}-amine;
(5-Ethoxymethyl-2-methyl-phenyl)-{5-[4-(4-methyl-pyrazol-1-yl)-phenyl]-oxazol-2-yl}-amine;
(5-Ethoxymethyl-2-methyl-phenyl)-{5-[4-(5-methyl-pyrazol-1-yl)-phenyl]-oxazol-2-yl}-amine;
(5-Ethoxymethyl-2-methyl-phenyl)-{5-[4-(3-methoxy-pyrazol-1-yl)-phenyl]-oxazol-2-yl}-amine;
2-{4-[2-(5-Ethoxymethyl-(2-methyl-phenylamino))-oxazol-5-yl]-phenyl}-2,4-dihydro-[1,2,4]triazol-3-one;
1-{4-[2-(5-Ethoxymethyl-(2-methyl-phenylamino))-oxazol-5-yl]-phenyl}-3-methyl-imidazolidin-2-one;
1-(2-Amino-ethyl)-3-{4-[2-(5-ethoxymethyl-(2-methyl-phenylamino))-oxazol-5-yl]-phenyl}-imidazolidin-2-one;
N-[2-(3-{4-[2-(5-Ethoxymethyl-(2-methyl-phenylamino))-oxazol-5-yl]-phenyl}-2-oxo-imidazolidin-1-yl)-ethyl]-acetamide;
1-{4-[2-(5-Ethoxymethyl-(2-methyl-phenylamino))-oxazol-5-yl]-phenyl}-pyrrolidin-2-one;
(5-Ethoxymethyl-2-methyl-phenyl)-[5-(4-pyridin-2-yl-phenyl)-oxazol-2-yl]-amine;
1-{4-[2-(5-Ethoxymethyl-(2-methyl-phenylamino))-oxazol-5-yl]-phenyl}-1H-pyridin-2-one;
3-{4-[2-(5-Ethoxymethyl-(2-methyl-phenylamino))-oxazol-5-yl]-phenyl}-1H-pyridin-2-one;
(R)-1-(4-(2-((5-(ethoxymethyl)-2-methylphenyl)amino)oxazol-5-yl)phenyl)-5-methylimidazolidin-2-one;
4-(4-(2-((5-(ethoxymethyl)-2-methylphenyl)amino)oxazol-5-yl)phenyl)-5-methyl-2,4-dihydro-3H-1,2,4-triazol-3-one;
1-(4-(2-((3,5-bis(ethoxymethyl)phenyl)amino)oxazol-5-yl)phenyl)imidazolidin-2-one;
1-(4-(2-((5-(ethoxymethyl)-2-methylphenyl)amino)oxazol-5-yl)phenyl)-3-(2-methoxyethyl)imidazolidin-2-one;
1-(5-(2-((5-(ethoxymethyl)-2-methylphenyl)amino)oxazol-5-yl)pyridin-2-yl)imidazolidin-2-one;
1-(4-(2-((3-(ethoxymethyl)-5-(2-methoxyethoxy)phenyl)amino)oxazol-5-yl)phenyl)imidazolidin-2-one;
5-(4-(1H-pyrazol-5-yl)phenyl)-N-(5-(ethoxymethyl)-2-methylphenyl)oxazol-2-amine;
(R)-1-(5-(2-((5-(ethoxymethyl)-2-methylphenyl)amino)oxazol-5-yl)pyridin-2-yl)-5-methylimidazolidin-2-one;
1-(4-(2-((3-(ethoxymethyl)-5-(2-hydroxyethoxy)phenyl)amino)oxazol-5-yl)phenyl)imidazolidin-2-one;

5-(4-(1H-pyrazol-4-yl)phenyl)-N-(5-(ethoxymethyl)-2-methylphenyl)oxazol-2-amine;

N-(5-(ethoxymethyl)-2-methylphenyl)-5-(4-(1-methyl-1H-pyrazol-5-yl)phenyl)oxazol-2-amine;

4-(6-(1H-pyrazol-1-yl)pyridin-3-yl)-N-(5-(ethoxymethyl)-2-methylphenyl)thiazol-2-amine;

1-(4-(2-((3-(ethoxymethyl)phenyl)amino)oxazol-5-yl)phenyl)imidazolidin-2-one;

1-(4-(2-((3-(ethoxymethyl)phenyl)amino)thiazol-4-yl)phenyl)imidazolidin-2-one.

The present invention further relates to a pharmaceutical composition comprising a compound according the invention, or a pharmaceutically acceptable salt thereof and at least one pharmaceutically acceptable excipients and/or carriers.

According to one embodiment, the pharmaceutical composition comprises a compound according to the invention, or a pharmaceutically acceptable salt thereof as sole active pharmaceutical ingredient.

According to one embodiment, the pharmaceutical composition of the invention further comprises another active pharmaceutical agent.

The invention also relates to a medicament comprising a compound according to the invention, or a pharmaceutically acceptable salt thereof.

The invention further relates to a compound according to the invention, or a pharmaceutically acceptable salt thereof, for use in the treatment of hematological disorders and/or proliferative disorders.

According to one embodiment, the hematological disorder is selected from lymphoma; leukemia such as Acute Myeloid Leukemia (AML), Acute Lymphoblastic Leukemia (ALL), Chronic Lymphoid Leukemia (CLL) or Chronic Myeloid Leukemia (CML); multiple myeloma (MM); myelodysplatic syndrome (MDS); and myelodysplasia with myelofibrosis.

According to one embodiment, the proliferative disorder is cancer, such as head and neck cancer, melanoma, kidney carcinoma, stomach carcinoma, liver carcinoma, colorectal carcinoma, pancreas carcinoma, lung carcinoma, neuronal carcinoma, glioblastoma multiform, osteosarcoma, Ewing sarcoma, breast carcinoma, ovary carcinoma, or prostate carcinoma.

The invention also relates to a pharmaceutical composition comprising a compound according to the invention, or a pharmaceutically acceptable salt thereof, and another active pharmaceutical ingredient as a combined preparation for sequential, simultaneous or separate use in the treatment of a disorder selected from the group consisting of hematological disorders and proliferative disorders.

DEFINITIONS

Unless otherwise specified, the below terms used herein are defined as follows.

Unless indicated otherwise, the nomenclature of substituents that are not explicitly defined herein are arrived at by naming the terminal portion of the functionality followed by the adjacent functionality toward the point of attachment. For example, the substituent "arylalkyl" refers to the group (aryl)-(alkyl)-.

As used herein the term "substituent" or "substituted" means that a hydrogen radical on a compound or group is replaced with any desired group that is substantially stable to reaction conditions in an unprotected form or when protected using a protecting group. Examples of preferred substituents are those found in the exemplary compounds and embodiments disclosed herein, as well as halogen, alkyl or aryl groups as defined above, hydroxyl, alkoxy group as defined above, nitro, thiol, heterocycloalkyl groups, heteroaryl groups, cyano, cycloalkyl groups as defined above, as well as a solubilizing group, —NRR', —NR—CO—W, —CONRR', —SO$_2$NRR' group wherein R and R' are each independently selected from hydrogen, alkyl, cycloalkyl, aryl, heterocycloalkyl or heteroaryl groups as defined above.

As used herein, the term "halogen" means fluoro, chloro, bromo, or iodo.

As used herein, the term "alkyl" means a saturated straight chain or branched non-cyclic hydrocarbon having from 1 to 10 carbon atoms, preferably from 1 to 6 carbon atoms, more preferably from 1 to 4 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents. Alkyl groups included in compounds of this invention may be optionally substituted with a solubilizing group.

As used herein, the term "alkoxy" refers to an alkyl group as defined above which is attached to another moiety by an oxygen atom. Examples of alkoxy groups include methoxy, isopropoxy, ethoxy, tert-butoxy, and the like. Alkoxy groups may be optionally substituted with one or more substituents. Alkoxy groups included in compounds of this invention may be optionally substituted with a solubilizing group.

As used herein, the term "heterocycle" refers collectively to heterocycloalkyl groups and heteroaryl groups.

As used herein, the term "heterocycloalkyl" means a monocyclic or polycyclic group having at least one heteroatom selected from O, N or S, and which has from 2 to 11 carbon atoms, which may be saturated or unsaturated, but is not aromatic. Examples of heterocycloalkyl groups including (but not limited to): piperidinyl, piperazinyl, N-methylpiperazinyl, 2-oxopiperazinyl, 2-oxopiperidinyl, 2-oxopyrrolidinyl, 4-piperidonyl, pyrrolidinyl, hydantoinyl, valerolactamyl, oxiranyl, oxetanyl, tetrahydropyranyl, tetrahydrothiopyranyl, 2-oxoimidazolidinyl, tetrahydro-pyrimidinyl-2-one, 2-oxopyrrolidinyl, tetrahydropyrindinyl, tetrahydropyrimidinyl, tetrahydrothiopyranyl sulfone, tetrahydrothiopyranyl sulfoxide, morpholinyl, thiomorpholinyl, thiomorpholinyl sulfoxide, thiomorpholinyl sulfone, 1,3-dioxolane, tetrahydrofuranyl, dihydrofuranyl-2-one, tetrahydrothienyl, and tetrahydro-1,1-dioxothienyl. Typically, monocyclic heterocycloalkyl groups have 3 to 7 members. Preferred 3 to 7 membered monocyclic heterocycloalkyl groups are those having 5 or 6 ring atoms. A heteroatom may be substituted with a protecting group known to those of ordinary skill in the art, for example, the hydrogen on a nitrogen may be substituted with a tert-butoxycarbonyl group. Furthermore, heterocycloalkyl groups may be optionally substituted with one or more substituents. In addition, the point of attachment of a heterocyclic ring to another group may be at either a carbon atom or a heteroatom of a heterocyclic ring. Only stable isomers of such substituted heterocyclic groups are contemplated in this definition.

As used herein, the term "heteroaryl" or like terms means a monocyclic or polycyclic heteroaromatic ring comprising carbon atom ring members and one or more heteroatom ring members (such as, for example, oxygen, sulfur or nitrogen). Typically, a heteroaryl group has from 1 to about 5 heteroatom ring members and from 1 to about 14 carbon atom ring members. Representative heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl, thiazolyl, thiadiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzo(b)thienyl. A heteroatom may be substituted with a protecting group known to those of ordinary skill in the art, for example, the hydrogen on nitrogen may be substituted with a tert-butoxycarbonyl group. In addition, nitrogen or sulfur heteroatom ring members may be oxidized. In one embodiment, the heteroaromatic ring is selected from 5-8 membered monocyclic heteroaryl rings. According to a specific embodiment, the heteroaryl group is a five member ring heteroaryl group. The point of attachment of a heteroaromatic or heteroaryl ring to another group may be at either a carbon atom or a heteroatom of the heteroaromatic or heteroaryl rings.

As used herein, the term "aryl" means a monocyclic or polycyclic-aromatic radical comprising carbon and hydrogen atoms. Examples of suitable aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl.

The term "cycloalkyl group" means a saturated or partially unsaturated, monocyclic, fused bicyclic or bridged polycyclic ring assembly containing the number of ring atoms indicated. This includes substituted or unsubstituted cycloalkyl groups. For example, cycloalkyl group may be C3-C10 alkyl group, such as C3 or C4, in particular a cyclopropyl, cyclobutyl, cyclopentyl, cyclohexyl, cycloheptyl or cyclooctyl group etc.

As used herein, the term "solubilizing group" means a group which improve the solubility of a compound in water or aqueous solution, as compared to an analog compound that does not include the group. Non-limiting examples of such solubilizing groups are groups that ionize under the conditions of use to form charged moieties (e.g., carboxylic acids, sulfonic acids, phosphoric acids, amines, etc.); groups that include permanent charges (e.g., quaternary ammonium groups); and/or heteroatoms or heteroatomic groups such as O, S, N, NH, N—$(CH_2)_z$R, N—$(CH_2)_z$—C(O)R, N—$(CH_2)_z$—C(O)OR, N—$(CH_2)_z$—S(O)$_2$R, N—$(CH_2)_z$—S(O)$_2$OR, N—$(CH_2)_z$—C(O)NRR', where z is an integer ranging from 0 to 6; R and R' each independently are selected from hydrogen, an alkyl group containing from 1 to 10 carbon atoms and optionally substituted with one or more hetereoatoms such as halogen (selected from F, Cl, Br or I), oxygen, and nitrogen; as well as alkoxy group containing from 1 to 10 carbon atoms; as well as aryl and heteroaryl group.

In some embodiments, the solubilizing group is a heterocycloalkyl that optionally includes from 1 to 5 substituents, which may themselves be solubilizing groups.

In a specific embodiment, the solubilizing group is of the formula:

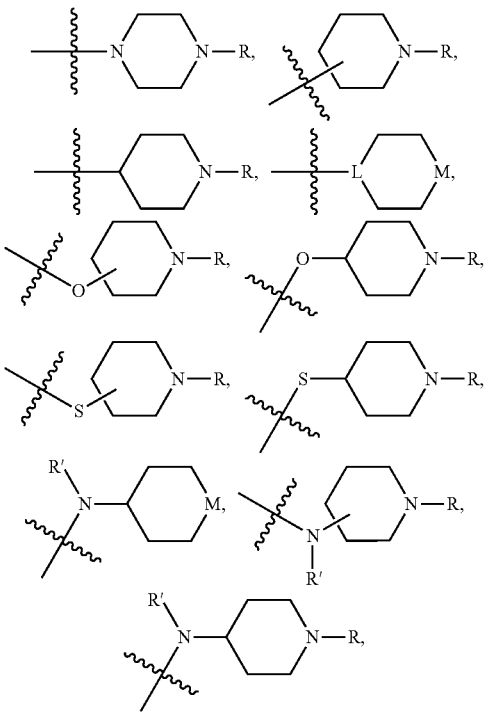

wherein L is selected from the group consisting of CH and N; M is selected from the group consisting of —CH(R)—, —$CH_2$—, —O—, —S—, —NH—, —N(—$(CH_2)_z$—R)—, —N(—$(CH_2)_z$—C(O)R)—, —N(—$(CH_2)_z$—C(O)OR)—, —N(—$(CH_2)_z$—S(O)$_2$R)—, —N($CH_2)_z$—S(O)$_2$OR)— and —N(—$(CH_2)_z$—C(O)NRR')—, where z is an integer ranging from 0 to 6, R and R' each independently are selected from hydrogen, an alkyl group containing from 1 to 10 carbon atoms and optionally substituted with one or more hetereoatoms such as halogen (selected from F, Cl, Br or I), oxygen, and nitrogen; as well as alkoxy group containing from 1 to 10 carbon atoms, NRR' group wherein R and R' are each independently selected from hydrogen, alkyl group as defined above optionally substituted with at least one heteroatom, notably oxygen or nitrogen optionally substituted with an alkyl group containing from 1 to 10 carbons optionally substituted; as well as aryl and heteroaryl group, with the proviso that L and M are not both simultaneously CH and $CH_2$, respectively.

In another specific embodiment, the solubilizing group is selected from the group consisting of morpholinyl, piperidinyl, pyrrolidinyl, N—(C1-C6)alkyl piperidinyl, in particular N-methyl piperidinyl and N-ethyl piperidinyl, N-(4-piperidinyl)piperidinyl, 4-(1-piperidinyl)piperidinyl, 1-pyrrolidinylpiperidinyl, 4-morpholinopiperidinyl, 4-(N-methyl-1-piperazinyl)piperidinyl, piperazinyl, N—(C1-C6) alkylpiperazinyl, in particular N-methyl piperazinyl and N-ethyl piperazinyl, N—(C3-C6)cycloalkyl piperazinyl, in particular N-cyclohexyl piperazinyl, pyrrolidinyl, N—(C1-C6)alkyl pyrrolidinyl, in particular N-methyl pyrrolidinyl and N-ethyl pyrrolidinyl, diazepinyl, N—(C1-C6)alkyl azepinyl, in particular N-methyl azepinyl and N-ethyl azepinyl, homopiperazinyl, N-methyl homopiperazinyl, N-ethyl homopiperazinyl, imidazolyl, and the like.

The term "solvate" is used herein to describe a molecular complex comprising the compound of the invention and one or more pharmaceutically acceptable solvent molecules, for example, ethanol. The term "hydrate" is employed when said solvent is water.

The term "solvate isomers" is used herein to describe two or more molecular complexes comprising the compound of the invention and one or more pharmaceutically acceptable solvent molecules, for example, ethanol, wherein said complexes differ by their number of solvent molecules per molecule of compound of the invention. The term "hydrate" is employed when said solvent is water.

The term "metabolite" is used herein to describe a compound resulting from the biochemical transformation of a parent compound by metabolism.

DETAILED DESCRIPTION

Compounds

The present invention relates to compounds capable to show an anti-proliferative activity against a large panel of tumor cell lines as single agent or in combination with other cytotoxic agents.

In a first embodiment, the invention is aimed at compounds of formula (I), which may represent either free base forms of the substances or pharmaceutically acceptable salts thereof:

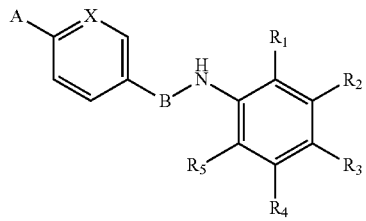

wherein:
R1, R2, R3, R4 and R5 are each independently selected from:
  hydrogen;
  heterocycle;
  cyano;
  $CF_3$;
  NRR';
  OH;
  halogen, preferably selected from F, Cl, Br and I;
  alkyl group optionally substituted by one or more group selected from heterocycle, NRR', OR and a solubilizing group;
  alkoxy group optionally substituted by one or more group selected from heterocycle, NRR', OR and a solubilizing group;
  CO—NRR';
  $SO_2$—NRR;
  NR—CO—R' and
  NR—$SO_2$R';
    wherein R and R' are each independently selected from hydrogen, cycloalkyl, heterocycle, solubilizing group and alkyl group optionally substituted by one or more group selected from OR", NR"R'", NR"COR'" and solubilizing group; wherein R" and R'" are each independently selected from hydrogen, alkyl or cycloalkyl;

A is an heterocycle group optionally substituted, preferably A is a heterocycle group optionally substituted by one or more group selected from halogen, alkyl, aryl, hydroxyl, alkoxy, nitro, thiol, heterocycloalkyl, heteroaryl, cyano, cycloalkyl, a solubilizing group, —NRR', -alkyl-NRR'; —NR—CO—R', -alkyl-NR—CO—R', —CONRR' and —$SO_2$NRR' group; wherein R and R' are each independently selected from hydrogen, alkyl, cycloalkyl, aryl, heterocycloalkyl and heteroaryl groups;

B is an aryl or a heteroaryl group;

X is N or C—R6, wherein R6 is selected from hydrogen, cyano, $CF_3$, alkyl and alkoxy.

According to one embodiment, among the compounds of formula (I), the present invention is directed to compounds wherein R3 is a hydrogen.

According to another embodiment, among the compounds of formula (I), the present invention is directed to compounds of the following formula (II):

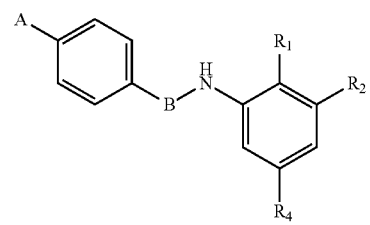

or a pharmaceutically acceptable salt thereof, wherein:
R1, R2 and R4 are each independently selected from:
  hydrogen; heterocycle; cyano; —$CF_3$; —NRR'; —OH; halogen preferably selected from F, Cl, Br and I; alkyl group optionally substituted by one or more group selected from heterocycle, NRR', OR and a solubilizing group; alkoxy group optionally substituted by one or more group selected from heterocycle, NRR', OR and a solubilizing group; —CO—NRR'; —$SO_2$—NRR'; —NR—CO—R' and —NR—$SO_2$R';
    wherein R and R' are each independently selected from hydrogen, cycloalkyl, heterocycle, solubilizing group and alkyl group optionally substituted by one or more group selected from OR", NR"R'", NR"COR'" and solubilizing group; wherein R" and R'" are each independently selected from hydrogen, alkyl or cycloalkyl;

A is selected from heterocycle group optionally substituted, preferable A is a heterocycle group optionally substituted by one or more group selected from halogen, alkyl, aryl, hydroxyl, alkoxy, nitro, thiol, heterocycloalkyl, heteroaryl, cyano, cycloalkyl, a solubilizing group, —NRR', -alkyl-NRR'; —NR—CO—R', -alkyl-NR—CO—R', —CONRR' and —$SO_2$NRR' group; wherein R and R' are each independently selected from hydrogen, alkyl, cycloalkyl, aryl, heterocycloalkyl and heteroaryl groups;

B is a five member ring heteroaryl group.

According to another embodiment, among the compounds of formula (I), the present invention is directed to compounds of the following formula

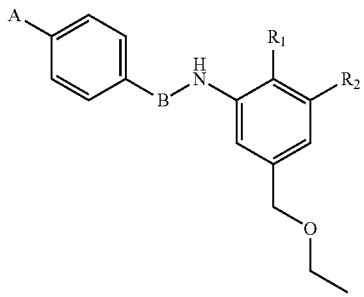

or a pharmaceutically acceptable salt thereof, wherein
R1 and R2 are each independently selected from: hydrogen; heterocycle; cyano; —CF$_3$; —NRR'; —OH; halogen preferably selected from F, Cl, Br and I; alkyl group optionally substituted by one or more group selected from heterocycle, NRR', OR and a solubilizing group; alkoxy group optionally substituted by one or more group selected from heterocycle, NRR', OR and a solubilizing group; —CO—NRR'; —SO$_2$—NRR'; —NR—CO—R' and —NR—SO$_2$R';
wherein R and R' are each independently selected from hydrogen, cycloalkyl, heterocycle, solubilizing group and alkyl group optionally substituted by one or more group selected from OR", NR"R'", NR"COR'" and solubilizing group; wherein R" and R'" are each independently selected from hydrogen, alkyl or cycloalkyl;
A is selected from heterocycle group optionally substituted, preferably A is a heterocycle group optionally substituted by one or more group selected from halogen, alkyl, aryl, hydroxyl, alkoxy, nitro, thiol, heterocycloalkyl, heteroaryl, cyano, cycloalkyl, a solubilizing group, —NRR', -alkyl-NRR'; —NR—CO—R', -alkyl-NR—CO—R', —CONRR' and —SO$_2$NRR' group; wherein R and R' are each independently selected from hydrogen, alkyl, cycloalkyl, aryl, heterocycloalkyl and heteroaryl groups;
B is a five member ring heteroaryl group.

According to a specific embodiment, in the compounds of the invention, R1 represents a hydrogen or an alkyl group, preferably R1 represents hydrogen or C1-C3 alkyl, more preferably R1 represents hydrogen, methyl, ethyl or propyl, even more preferably, R1 represents hydrogen or methyl. According to another specific embodiment, in the compounds of the invention, R1 represents an alkyl group, preferably R1 represents C1-C3 alkyl, more preferably R1 represents methyl, ethyl or propyl, even more preferably, R1 represents methyl.

According to a specific embodiment, in the compounds of the invention, R2 represents a hydrogen or an alkyl group optionally substituted by an alkoxy, preferably R2 represents hydrogen, methyl or —CH$_2$—O—C$_2$H$_5$. According to another specific embodiment, in the compounds of the invention, R2 represents a hydrogen.

According to a specific embodiment, in the compounds of the invention, R3 represents a hydrogen.

According to a specific embodiment, in the compounds of the invention, R4 represents alkyl group optionally substituted by one or more group selected from NRR' and OR; alkoxy group optionally substituted by one or more group selected from NRR' and a solubilizing group; or —CO—NRR'; wherein R and R are each independently selected from hydrogen and alkyl group optionally substituted by one or more group selected from OR", NR"R'", NR"COR'" and solubilizing group; wherein R" and R'" are each independently selected from hydrogen or alkyl. According to a specific embodiment, in the compounds of the invention, R4 represents alkyl group substituted by OR wherein R represents an alkyl group; or R4 represents an alkoxy group; preferably R4 represents —CH$_2$—O—C$_2$H$_5$ or —O—CH$_3$.

According to a specific embodiment, in the compounds of the invention, R5 represents a hydrogen.

According to a specific embodiment, in the compounds of the invention, R1 represents an alkyl group, R2 represents a hydrogen, R3 represents a hydrogen, R4 represents alkyl group substituted by OR wherein R represents an alkyl group; or R4 represents an alkoxy group; and R5 represents a hydrogen. According to a specific embodiment, in the compounds of the invention, R1 represents methyl, R2 represents a hydrogen, R3 represents a hydrogen, R4 represents —CH$_2$—O—C$_2$H$_5$ or —O—CH$_3$; and R5 represents a hydrogen. According to a specific embodiment, in the compounds of the invention, R1 is methyl, R2, R3 and R5 are hydrogen and R4 is —CH$_2$OC$_2$H$_5$.

According to a specific embodiment, in the compounds of the invention, X represents N or C—R6, wherein R6 is selected from hydrogen and alkoxy group. According to a specific embodiment, in the compounds of the invention, X represents N, CH or C(OCH$_3$). According to a preferred embodiment, in the compounds of the invention, X represents CH.

According to a specific embodiment, in the compounds of the invention, A represents a heterocycloalkyl group. Alternatively, in the compounds of the invention, A represents a heteroaryl group. According to a specific embodiment, in the compounds of the invention, A represents triazolyl, oxotriazolyl, imidazolyl, oxoimidazolidinyl, pyrazolyl, pyridyl, oxopyridyl, thiazolyl or oxopyrrolidinyl. According to a specific embodiment, in the compounds of the invention, A represents 2-oxoimidazolidinyl or pyrazolyl, more preferably A represents 2-oxoimidazolidinyl.

According to a specific embodiment, in the compounds of the invention, A is a heterocycle group substituted by one or more group selected from halogen, alkyl, aryl, hydroxyl, alkoxy, nitro, thiol, heterocycloalkyl, heteroaryl, cyano, cycloalkyl, a solubilizing group, —NRR', -alkyl-NRR'; —NR—CO—R', -alkyl-NR—CO—R', —CONRR' and —SO$_2$NRR' group; wherein R and R' are each independently selected from hydrogen, alkyl, cycloalkyl, aryl, heterocycloalkyl and heteroaryl groups. According to a specific embodiment, in the compounds of the invention, A is a heterocycle group substituted by alkyl, alkoxy, -alkyl-NRR' or -alkyl-NR—CO—R, more preferably A is substituted by methyl, methoxy, —CH$_2$—CH$_2$—NH$_2$ or —CH$_2$—CH$_2$—NHCO—CH$_3$.

According to a specific embodiment, in the compounds of the invention, B represents an aryl group. Alternatively, B represents a heteroaryl group. According to a specific embodiment, in the compounds of the invention, B represents a five member ring heteroaryl. According to specific embodiment, in the compounds of the invention, B represents oxadiazolyl, oxazolyl, thiadiazolyl or thiazolyl, preferably, B represents oxadiazolyl, oxazolyl or thiazolyl. According to a specific embodiment, B is not selected from 1,2 diazinyl, triazolopyridinyl or triazolyl.

According to a specific embodiment, in the compounds of the invention, B represents oxazolyl or thiazolyl. According to a specific embodiment, if B is oxazolyl, A is not tetrazolyl or tetrahydropyridinyl. According to a specific embodiment, if B is thiazolyl, A is not imidazolyl, triazolyl, piperazinyl, pyrrolidinyl, piperidinyl or 1,4-oxazinyl.

According to a specific embodiment, in the compounds of the invention, X is CH and A is 2-oxoimidazolidinyl or pyrazolyl group.

According to one embodiment, in compounds of formula (III), R1 and R2 are each independently hydrogen or alkyl group (preferably C1-C3 alkyl, more preferably methyl, ethyl or propyl), A is 2-oxoimidazolidinyl and B is heteroaryl group.

According to a specific embodiment, in compounds of formula (III), R1 is methyl, R2 is hydrogen, A is 2-oxoimidazolidinyl or pyrazolyl and B is oxazole, thiazol or oxadiazol ring.

According to one embodiment, among the compounds of formula (I), the present invention is directed to compounds of the following formula (IVa) or (IVb):

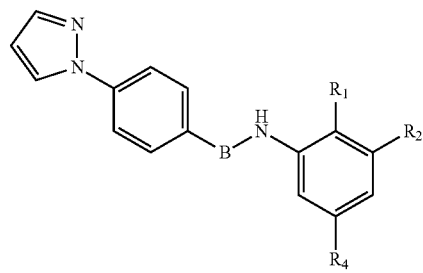

(IVa)

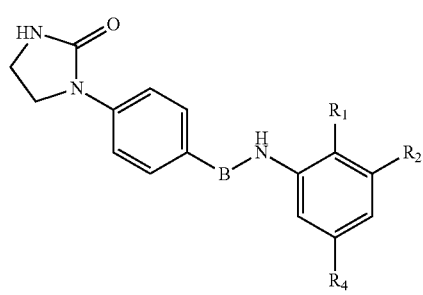

(IVb)

wherein B, R1, R2 and R4 are as described above.

According to one embodiment, among the compounds of formula (I), the present invention is directed to compounds of the following formula (Va) or (Vb):

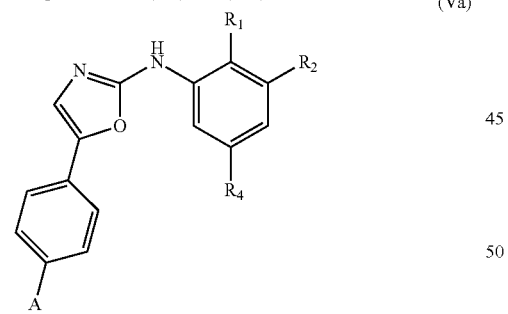

(Va)

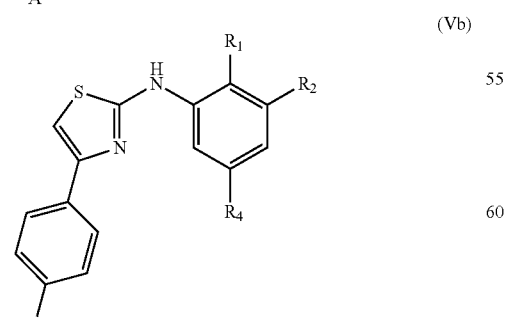

(Vb)

wherein A, R1, R2 and R4 are as described above.

According to one embodiment, among the compounds of formula (I), the present invention is directed to compounds of the following formula (VIa), (VIb), (VIc) or (VId):

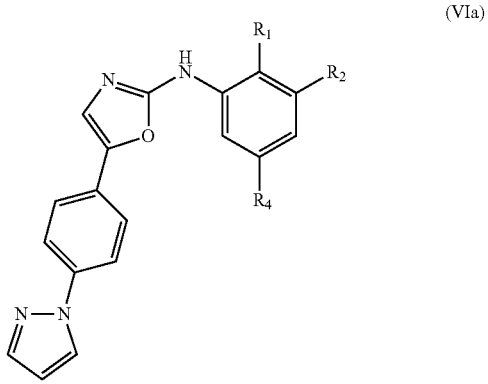

(VIa)

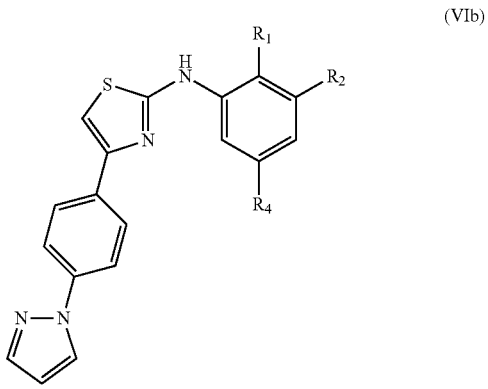

(VIb)

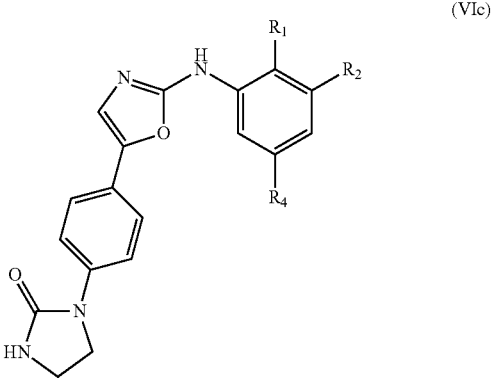

(VIc)

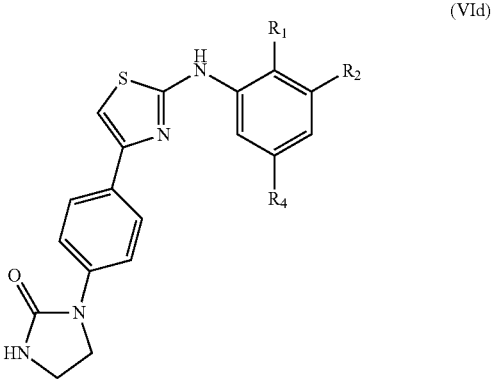

(VId)

wherein R1, R2 and R4 are as described above.

Examples of preferred compounds of the above formulas are depicted in table 1 below:

TABLE 1

| Ex # | Chemical structure | Name | ¹H NMR/LCMS |
|---|---|---|---|
| 001 | 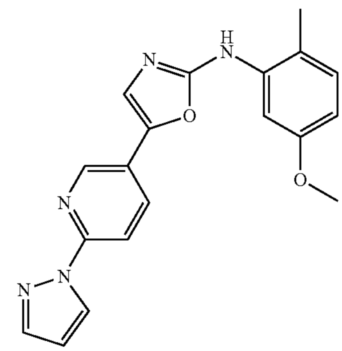 [SMILES: COc1ccc(C)c(Nc2ncc(-c3ccc(-n4cccn4)nc3)o2)c1] | (5-Methoxy-2-methyl-phenyl)-[5-(6-pyrazol-1-yl-pyridin-3-yl)-oxazol-2-yl]-amine | ¹H NMR (300 MHz, DMSO-d6) δ 9.38 (s, 1H), 8.68 (d, J = 2.1 Hz, 1H), 8.62 (d, J = 2.4 Hz, 1H), 8.12 (dd, J = 8.6, 2.3 Hz, 1H), 7.99 (d, J = 8.6 Hz, 1H), 7.84 (s, 1H), 7.59 (s, 2H), 7.09 (d, J = 8.3 Hz, 1H), 6.66-6.51 (m, 2H), 3.73 (s, 3H), 2.23 (s, 3H). |
| 002 | 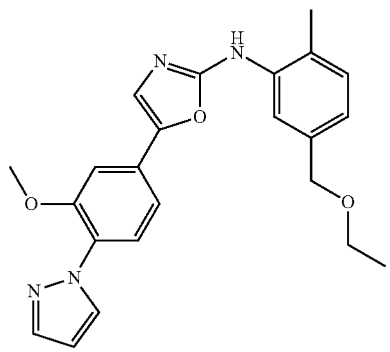 [SMILES: CCOCc1ccc(C)c(Nc2ncc(-c3ccc(-n4cccn4)c(OC)c3)o2)c1] | (5-Ethoxymethyl-2-methyl-phenyl)-[5-(3-methoxy-4-pyrazol-1-yl-phenyl)-oxazol-2-yl]-amine | ¹H NMR (500 MHz, DMSO-d6) δ 9.33 (s, 1H), 8.20 (d, J = 2.3 Hz, 1H), 7.85 (s, 1H), 7.74-7.66 (m, 2H), 7.55 (s, 1H), 7.39 (d, J = 1.6 Hz, 1H), 7.29 (dd, J = 8.3, 1.7 Hz, 1H), 7.18 (d, J = 7.7 Hz, 1H), 6.95 (dd, J = 7.6, 1.2 Hz, 1H), 6.52-6.45 (m, 1H), 4.43 (s, 2H), 3.95 (s, 3H), 3.49 (q, J = 7.0 Hz, 2H), 2.30 (s, 3H), 1.16 (t, J = 7.0 Hz, 3H). |
| 003 | 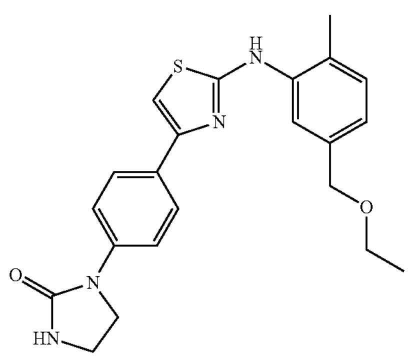 [SMILES: CCOCc1ccc(C)c(Nc2nc(-c3ccc(N4CCNC4=O)cc3)cs2)c1] | 1-{4-[2-(5-Ethoxymethyl-(2-methyl-phenylamino))-thiazol-4-yl]-phenyl}-imidazolidin-2-one | ¹H NMR (500 MHz, DMSO-d6) δ 9.29 (s, 1H), 8.05 (s, 1H), 7.81 (d, J = 8.8 Hz, 2H), 7.58 (d, J = 8.9 Hz, 2H), 7.18 (d, J = 7.7 Hz, 1H), 7.12 (s, 1H), 6.96 (s, 1H), 6.93 (d, J = 7.7 Hz, 1H), 4.44 (s, 2H), 3.91-3.83 (m, 2H), 3.50 (q, J = 7.0 Hz, 2H), 3.45-3.37 (m, 2H), 2.27 (s, 3H), 1.17 (t, J = 7.0 Hz, 3H). |
| 004 | 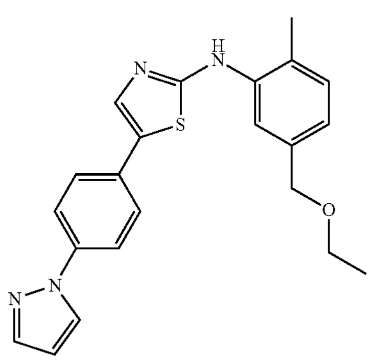 [SMILES: CCOCc1ccc(C)c(Nc2ncc(-c3ccc(-n4cccn4)cc3)s2)c1] | (5-Ethoxymethyl-2-methyl-phenyl)-[5-(4-pyrazol-1-yl-phenyl)-thiazol-2-yl]-amine | ¹H NMR (500 MHz, DMSO-d6) δ 9.42 (s, 1H), 8.50 (d, J = 2.4 Hz, 1H), 7.83 (d, J = 8.7 Hz, 2H), 7.79 (s, 1H), 7.75 (d, J = 1.6 Hz, 1H), 7.67 (s, 1H), 7.60 (d, J = 8.7 Hz, 2H), 7.20 (d, J = 7.7 Hz, 1H), 6.98 (d, J = 7.7 Hz, 1H), 6.60-6.52 (m, 1H), 4.42 (s, 2H), 3.48 (q, J = 7.0 Hz, 2H), 2.27 (s, 3H), 1.15 (t, J = 7.0 Hz, 3H). |

TABLE 1-continued

| Ex # | Chemical structure | Name | ¹H NMR/LCMS |
|---|---|---|---|
| 005 | 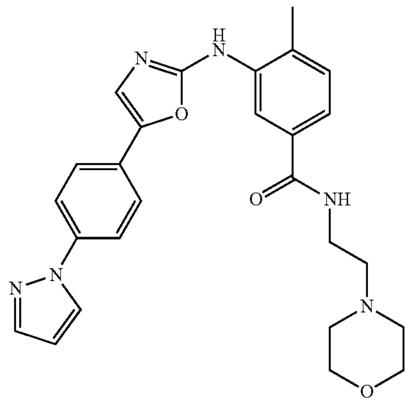 [SMILES: Cc1ccc(C(=O)NCCN2CCOCC2)cc1Nc1ncc(-c2ccc(-n3cccn3)cc2)o1] | 4-Methyl-N-(2-morpholin-4-yl-ethyl)-3-[5-(4-pyrazol-1-yl-phenyl)-oxazol-2-ylamino]-benzamide | ¹H NMR (300 MHz, DMSO-d6) δ 9.41 (s, 1H), 8.54 (d, J = 2.4 Hz, 1H), 8.32 (s, 1H), 8.29 (d, J = 5.7 Hz, 1H), 7.92 (d, J = 8.8 Hz, 2H), 7.76 (d, J = 1.6 Hz, 1H), 7.69 (d, J = 8.7 Hz, 2H), 7.47 (s, 1H), 7.45 (dd, J = 7.9, 1.7 Hz, 1H), 7.28 (d, J = 7.9 Hz, 1H), 6.59-6.53 (m, 1H), 3.61-3.52 (m, 4H), 3.42-3.33 (m, 2H), 2.47 (m, 2H), 2.42 (m, 4H), 2.34 (s, 3H). |
| 006 | 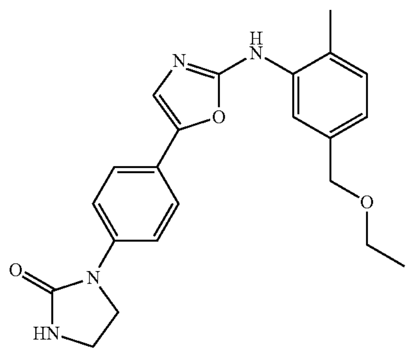 [SMILES: CCOCc1ccc(C)c(Nc2ncc(-c3ccc(N4CCNC4=O)cc3)o2)c1] | 1-{4-[2-(5-Ethoxymethyl-(2-methyl-phenylamino))-oxazol-5-yl]-phenyl}-imidazolidin-2-one | ¹H NMR (500 MHz, DMSO-d6) δ 9.16 (s, 1H), 7.84 (s, 1H), 7.63 (d, J = 8.9 Hz, 2H), 7.52 (d, J = 8.8 Hz, 2H), 7.28 (s, 1H), 7.16 (d, J = 7.7 Hz, 1H), 7.00 (s, 1H), 6.93 (d, J = 7.6 Hz, 1H), 4.42 (s, 2H), 3.91-3.85 (m, 2H), 3.48 (q, J = 7.0 Hz, 2H), 3.45-3.38 (m, 2H), 2.28 (s, 3H), 1.15 (t, J = 7.0 Hz, 3H). |
| 007 | 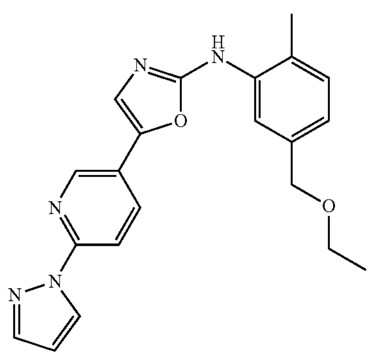 [SMILES: CCOCc1ccc(C)c(Nc2ncc(-c3ccc(-n4cccn4)nc3)o2)c1] | (5-Ethoxymethyl-2-methyl-phenyl)-[5-(6-pyrazol-1-yl-pyridin-3-yl)-oxazol-2-yl]-amine | ¹H NMR (500 MHz, DMSO-d6) δ 9.39 (s, 1H), 8.67 (d, J = 2.0 Hz, 1H), 8.62 (d, J = 2.5 Hz, 1H), 8.12 (dd, J = 8.6, 2.3 Hz, 1H), 7.98 (d, J = 8.6 Hz, 1H), 7.84 (d, J = 1.1 Hz, 1H), 7.80 (s, 1H), 7.57 (s, 1H), 7.18 (d, J = 7.7 Hz, 1H), 6.96 (d, J = 7.6 Hz, 1H), 6.61-6.56 (m, 1H), 4.42 (s, 2H), 3.48 (q, J = 7.0 Hz, 2H), 2.28 (s, 3H), 1.16 (t, J = 7.0 Hz, 3H). |
| 008 | 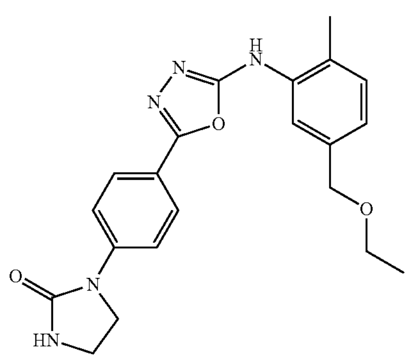 [SMILES: CCOCc1ccc(C)c(Nc2nnc(-c3ccc(N4CCNC4=O)cc3)o2)c1] | 1-{4-[5-(5-Ethoxymethyl-(2-methyl-phenylamino))-[1,3,4]oxadiazol-2-yl]-phenyl}-imidazolidin-2-one | ¹H NMR (500 MHz, DMSO-d6) δ 9.56 (s, 1H), 7.84-7.81 (m, 2H), 7.78 (d, J = 3.0 Hz, 1H), 7.78-7.75 (m, 2H), 7.20 (d, J = 7.7 Hz, 1H), 7.17 (s, 1H), 6.99 (dd, J = 7.7, 1.4 Hz, 1H), 4.44 (s, 2H), 3.92 (dd, J = 9.0, 7.0 Hz, 2H), 3.54-3.41 (m, 4H), 2.30 (s, 3H), 1.21-1.12 (m, 3H). |

TABLE 1-continued

| Ex # | Chemical structure | Name | ¹H NMR/LCMS |
|---|---|---|---|
| 009 | 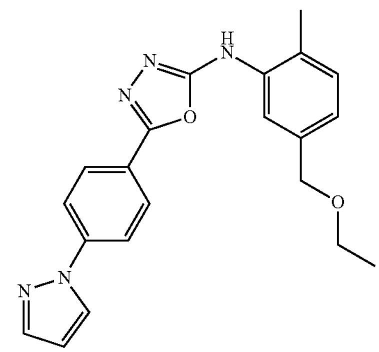 [SMILES: CCOCc1ccc(C)c(Nc2nnc(-c3ccc(-n4cccn4)cc3)o2)c1] | (5-Ethoxymethyl-2-methyl-phenyl)-[5-(4-pyrazol-1-yl-phenyl)-[1,3,4]oxadiazol-2-yl]-amine | ¹H NMR (500 MHz, DMSO-d6) δ 9.67 (s, 1H), 8.63 (d, J = 2.4 Hz, 1H), 8.10-8.05 (m, 2H), 8.03-7.95 (m, 2H), 7.83 (d, J = 1.6 Hz, 1H), 7.78 (d, J = 1.0 Hz, 1H), 7.22 (d, J = 7.7 Hz, 1H), 7.01 (dd, J = 7.7, 1.4 Hz, 1H), 6.62 (dd, J = 2.5, 1.8 Hz, 1H), 4.45 (s, 2H), 3.50 (q, J = 7.0 Hz, 2H), 2.31 (s, 3H), 1.20-1.12 (m, 3H). |
| 010 | 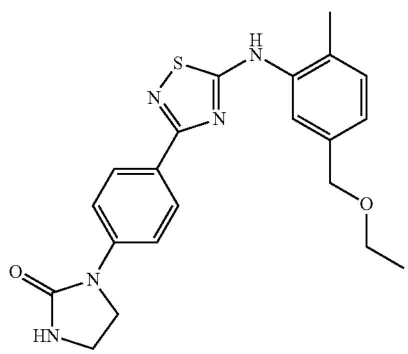 [SMILES: CCOCc1ccc(C)c(Nc2nc(-c3ccc(N4CCNC4=O)cc3)ns2)c1] | 1-{4-[5-(5-Ethoxymethyl-(2-methyl-phenylamino))-[1,2,4]thiadiazol-3-yl]-phenyl}-imidazolidin-2-one | ¹H NMR (500 MHz, CDCl₃) δ 8.08 (d, J = 8.9 Hz, 2H), 7.57 (d, J = 8.9 Hz, 2H), 7.47 (s, 1H), 7.29 (s, 1H), 7.22 (d, J = 7.7 Hz, 1H), 7.08 (d, J = 6.7 Hz, 1H), 4.48 (s, 2H), 4.00-3.92 (m, 2H), 3.55 (m, 4H), 2.31 (s, 3H), 1.22 (dd, J = 9.0, 5.0 Hz, 3H). |
| 011 | 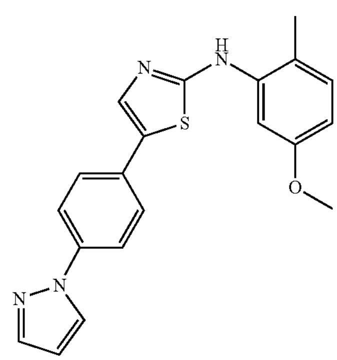 [SMILES: COc1ccc(C)c(Nc2ncc(-c3ccc(-n4cccn4)cc3)s2)c1] | (5-Methoxy-2-methyl-phenyl)-[5-(4-pyrazol-1-yl-phenyl)-thiazol-2-yl]-amine | ¹H NMR (500 MHz, DMSO-d6) δ 9.39 (s, 1H), 8.51 (d, J = 2.5 Hz, 1H), 7.86-7.82 (m, 2H), 7.75 (d, J = 1.6 Hz, 1H), 7.68 (s, 1H), 7.64-7.60 (m, 2H), 7.57 (d, J = 2.1 Hz, 1H), 7.11 (d, J = 8.4 Hz, 1H), 6.61 (dd, J = 8.3, 2.6 Hz, 1H), 6.56-6.54 (m, 1H), 3.73 (s, 3H), 2.21 (s, 3H). |
| 012 | 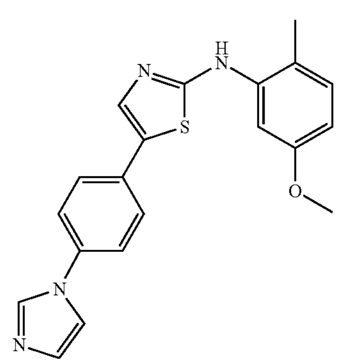 [SMILES: COc1ccc(C)c(Nc2ncc(-c3ccc(-n4ccnc4)cc3)s2)c1] | [5-(4-Imidazol-1-yl-phenyl)-thiazol-2-yl]-(5-methoxy-2-methyl-phenyl)-amine | ¹H NMR (500 MHz, DMSO-d6) δ 9.42 (s, 1H), 8.27 (s, 1H), 7.76 (t, J = 1.3 Hz, 1H), 7.71 (s, 1H), 7.67-7.60 (m, 4H), 7.57 (d, J = 1.6 Hz, 1H), 7.13-7.08 (m, 2H), 6.61 (dd, J = 8.3, 2.6 Hz, 1H), 3.73 (s, 3H), 2.21 (s, 3H). |

TABLE 1-continued

| Ex # | Chemical structure | Name | ¹H NMR/LCMS |
|---|---|---|---|
| 013 | 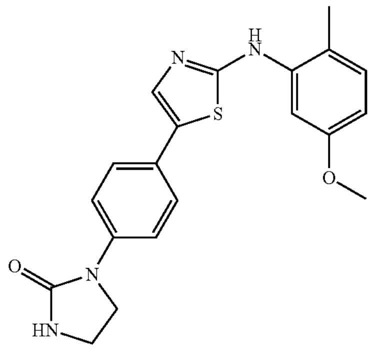 [SMILES: COc1ccc(C)c(Nc2ncc(-c3ccc(N4CCNC4=O)cc3)s2)c1] | 1-{4-[2-(5-Methoxy-2-methyl-phenylamino)-thiazol-5-yl]-phenyl}-imidazolidin-2-one | ¹H NMR (500 MHz, DMSO-d6) δ 9.27 (s, 1H), 7.59 (d, J = 2.2 Hz, 1H), 7.57 (d, J = 8.9 Hz, 2H), 7.53 (s, 1H), 7.44 (d, J = 8.8 Hz, 2H), 7.11 (d, J = 8.4 Hz, 1H), 6.97 (s, 1H), 6.59 (dd, J = 8.3, 2.6 Hz, 1H), 3.86 (dd, J = 8.9, 7.0 Hz, 2H), 3.73 (s, 3H), 3.45-3.39 (m, 2H), 2.21 (s, 3H). |
| 014 | 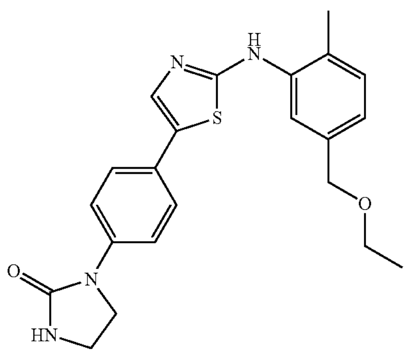 [SMILES: CCOCc1ccc(C)c(Nc2ncc(-c3ccc(N4CCNC4=O)cc3)s2)c1] | 1-{4-[2-(5-Ethoxymethyl-(2-methyl-phenylamino))-thiazol-5-yl]-phenyl}-imidazolidin-2-one | ¹H NMR (500 MHz, DMSO-d6) δ 9.29 (s, 1H), 7.81 (s, 1H), 7.56 (d, J = 8.9 Hz, 2H), 7.51 (s, 1H), 7.43 (d, J = 8.8 Hz, 2H), 7.19 (d, J = 7.7 Hz, 1H), 7.04-6.90 (m, 2H), 4.42 (s, 2H), 3.91-3.78 (m, 2H), 3.48 (q, J = 7.0 Hz, 2H), 3.45-3.39 (m, 2H), 2.27 (s, 3H), 1.15 (t, J = 7.0 Hz, 3H). |
| 015 | 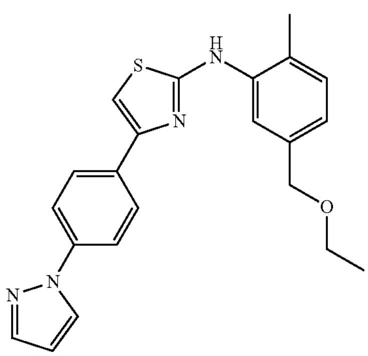 [SMILES: CCOCc1ccc(C)c(Nc2nc(-c3ccc(-n4cccn4)cc3)cs2)c1] | (5-Ethoxymethyl-2-methyl-phenyl)-[4-(4-pyrazol-1-yl-phenyl)-thiazol-2-yl]-amine | ¹H NMR (500 MHz, DMSO-d6) δ 9.36 (s, 1H), 8.54 (d, J = 2.4 Hz, 1H), 8.07 (s, 1H), 7.99 (d, J = 8.7 Hz, 2H), 7.87 (d, J = 8.7 Hz, 2H), 7.76 (d, J = 1.5 Hz, 1H), 7.33 (s, 1H), 7.19 (d, J = 7.7 Hz, 1H), 6.95 (d, J = 7.6 Hz, 1H), 6.60-6.51 (m, 1H), 4.45 (s, 2H), 3.52 (q, J = 7.0 Hz, 2H), 2.29 (s, 3H), 1.18 (t, J = 7.0 Hz, 3H). |
| 016 | 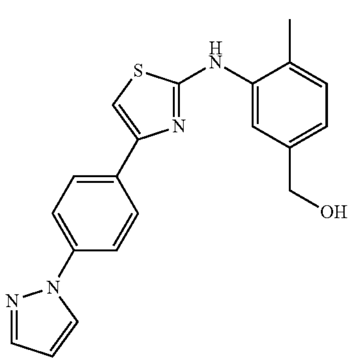 [SMILES: Cc1ccc(CO)cc1Nc1nc(-c2ccc(-n3cccn3)cc2)cs1] | {4-Methyl-3-[4-(4-pyrazol-1-yl-phenyl)-thiazol-2-ylamino]-phenyl}-methanol | ¹H NMR (500 MHz, DMSO-d6) δ 9.35 (s, 1H), 8.54 (d, J = 2.4 Hz, 1H), 7.99 (d, J = 8.8 Hz, 2H), 7.95 (s, 1H), 7.88 (d, J = 8.8 Hz, 2H), 7.76 (d, J = 1.6 Hz, 1H), 7.31 (s, 1H), 7.19 (d, J = 7.7 Hz, 1H), 6.99 (d, J = 7.7 Hz, 1H), 6.58-6.54 (m, 1H), 5.16 (t, J = 5.7 Hz, 1H), 4.50 (d, J = 5.9 Hz, 2H), 2.28 (s, 3H). |

TABLE 1-continued

| Ex # | Chemical structure | Name | ¹H NMR/LCMS |
|---|---|---|---|
| 017 | 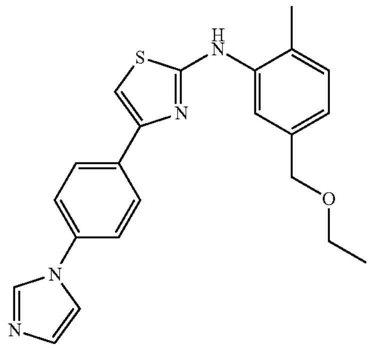 [SMILES: CCOCc1ccc(C)c(Nc2nc(-c3ccc(-n4ccnc4)cc3)cs2)c1] | (5-Ethoxymethyl-2-methyl-phenyl)-[4-(4-imidazol-1-yl-phenyl)-thiazol-2-yl]-amine | ¹H NMR (500 MHz, DMSO-d6) δ 9.38 (s, 1H), 8.30 (s, 1H), 8.06 (d, J = 0.9 Hz, 1H), 8.01 (d, J = 8.7 Hz, 2H), 7.79 (t, J = 1.3 Hz, 1H), 7.69 (d, J = 8.7 Hz, 2H), 7.37 (s, 1H), 7.20 (d, J = 7.7 Hz, 1H), 7.12 (s, 1H), 6.95 (dd, J = 7.6, 1.4 Hz, 1H), 4.45 (s, 2H), 3.51 (q, J = 7.0 Hz, 2H), 2.28 (s, 3H), 1.17 (t, J = 7.0 Hz, 3H). |
| 018 | 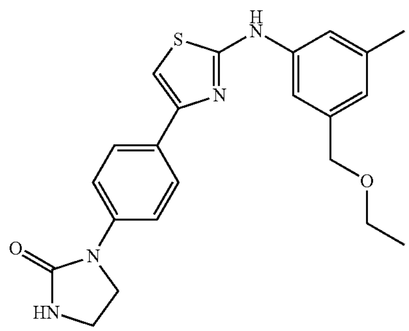 [SMILES: CCOCc1cc(C)cc(Nc2nc(-c3ccc(N4CCNC4=O)cc3)cs2)c1] | 1-{4-[2-(3-Ethoxymethyl-(5-methyl-phenylamino))-thiazol-4-yl]-phenyl}-imidazolidin-2-one | ¹H NMR (500 MHz, DMSO-d6) δ 10.15 (s, 1H), 7.85 (d, J = 8.8 Hz, 2H), 7.61 (d, J = 8.9 Hz, 3H), 7.38 (s, 1H), 7.18 (s, 1H), 6.97 (s, 1H), 6.72 (s, 1H), 4.43 (s, 2H), 3.92-3.84 (m, 2H), 3.51 (q, J = 7.0 Hz, 2H), 3.46-3.39 (m, 2H), 2.31 (s, 3H), 1.19 (t, J = 7.0 Hz, 3H). |
| 019 | 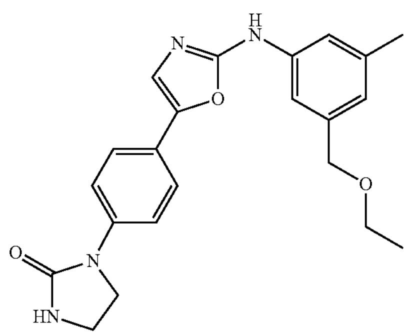 [SMILES: CCOCc1cc(C)cc(Nc2ncc(-c3ccc(N4CCNC4=O)cc3)o2)c1] | 1-{4-[2-(3-Ethoxymethyl-(5-methyl-phenylamino))-oxazol-5-yl]-phenyl}-imidazolidin-2-one | ¹H NMR (500 MHz, DMSO-d6) δ 10.16 (s, 1H), 7.63 (d, J = 8.9 Hz, 2H), 7.51 (d, J = 8.9 Hz, 2H), 7.41 (s, 1H), 7.38 (s, 1H), 7.31 (s, 1H), 7.00 (s, 1H), 6.71 (s, 1H), 4.39 (s, 2H), 3.91-3.83 (m, 2H), 3.49 (q, J = 7.0 Hz, 2H), 3.45-3.40 (m, 2H), 2.28 (s, 3H), 1.17 (t, J = 7.0 Hz, 3H). |
| 020 | 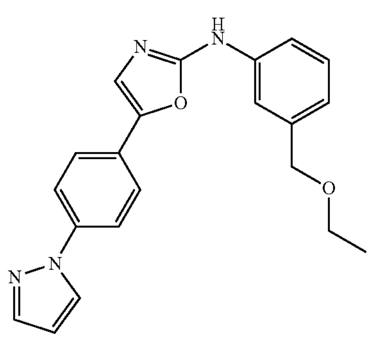 [SMILES: CCOCc1cccc(Nc2ncc(-c3ccc(-n4cccn4)cc3)o2)c1] | (3-Ethoxymethyl-phenyl)-[5-(4-pyrazol-1-yl-phenyl)-oxazol-2-yl]-amine | ¹H NMR (500 MHz, DMSO-d6) δ 10.33 (s, 1H), 8.53 (d, J = 2.4 Hz, 1H), 7.92 (d, J = 8.8 Hz, 2H), 7.76 (d, J = 1.5 Hz, 1H), 7.70 (d, J = 8.8 Hz, 2H), 7.64 (s, 1H), 7.55 (dd, J = 8.1, 1.4 Hz, 1H), 7.51 (s, 1H), 7.29 (t, J = 7.8 Hz, 1H), 6.91 (d, J = 7.5 Hz, 1H), 6.58-6.53 (m, 1H), 4.45 (s, 2H), 3.50 (q, J = 7.0 Hz, 2H), 1.17 (t, J = 7.0 Hz, 3H). |

TABLE 1-continued

| Ex # | Chemical structure | Name | ¹H NMR/LCMS |
|---|---|---|---|
| 021 | 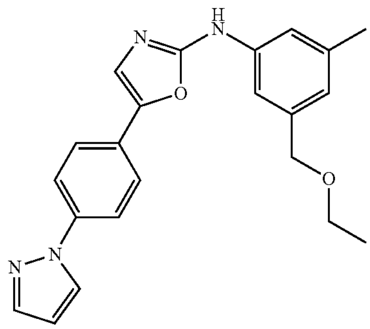 [SMILES: CCOCc1cc(C)cc(Nc2ncc(-c3ccc(-n4cccn4)cc3)o2)c1] | (3-Ethoxymethyl-5-methyl-phenyl)-[5-(4-pyrazol-1-yl-phenyl)-oxazol-2-yl]-amine | ¹H NMR (500 MHz, DMSO-d6) δ 10.25 (s, 1H), 8.53 (d, J = 2.4 Hz, 1H), 7.93 (d, J = 8.8 Hz, 2H), 7.76 (d, J = 1.6 Hz, 1H), 7.70 (d, J = 8.8 Hz, 2H), 7.50 (s, 1H), 7.42 (s, 1H), 7.38 (s, 1H), 6.73 (s, 1H), 6.59-6.51 (m, 1H), 4.40 (s, 2H), 3.49 (q, J = 7.0 Hz, 2H), 2.29 (s, 3H), 1.17 (t, J = 7.0 Hz, 3H). |
| 022 | 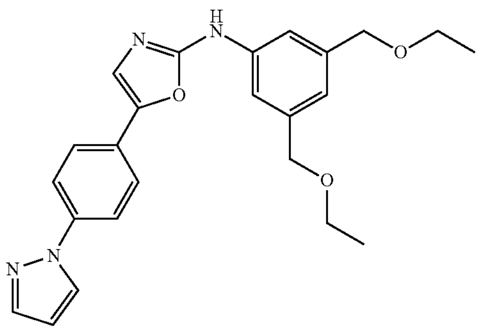 [SMILES: CCOCc1cc(COCC)cc(Nc2ncc(-c3ccc(-n4cccn4)cc3)o2)c1] | (3,5-Bis-(ethoxymethyl)-phenyl)-[5-(4-pyrazol-1-yl-phenyl)-oxazol-2-yl]-amine | ¹H NMR (500 MHz, DMSO-d6) δ 10.34 (s, 1H), 8.53 (d, J = 2.4 Hz, 1H), 7.93 (d, J = 8.8 Hz, 2H), 7.76 (d, J = 1.6 Hz, 1H), 7.70 (d, J = 8.8 Hz, 2H), 7.54 (s, 2H), 7.51 (s, 1H), 6.86 (s, 1H), 6.59-6.53 (m, 1H), 4.44 (s, 4H), 3.50 (q, J = 7.0 Hz, 4H), 1.17 (t, J = 7.0 Hz, 6H). |
| 023 | 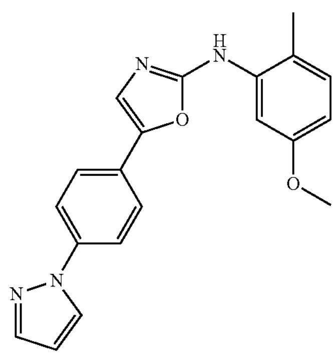 | (5-Methoxy-2-methyl-phenyl)-[5-(4-pyrazol-1-yl-phenyl)-oxazol-2-yl]-amine | ¹H NMR (500 MHz, DMSO-d6) δ 9.24 (s, 1H), 8.52 (d, J = 2.5 Hz, 1H), 7.92 (d, J = 8.9 Hz, 2H), 7.76 (d, J = 1.6 Hz, 1H), 7.69 (d, J = 8.8 Hz, 2H), 7.61 (d, J = 2.6 Hz, 1H), 7.47 (s, 1H), 7.09 (d, J = 8.4 Hz, 1H), 6.58-6.54 (m, 2H), 3.73 (s, 3H), 2.23 (s, 3H). |
| 024 | 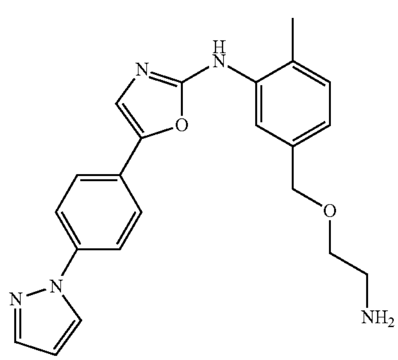 [SMILES: Cc1ccc(COCCN)cc1Nc1ncc(-c2ccc(-n3cccn3)cc2)o1] | [5-(2-Amino-ethoxymethyl)-2-methyl-phenyl]-[5-(4-pyrazol-1-yl-phenyl)-oxazol-2-yl]-amine | ¹H NMR (300 MHz, DMSO-d6) δ 8.53 (d, J = 2.4 Hz, 1H), 7.91 (d, J = 8.6 Hz, 2H), 7.85 (s, 1H), 7.76 (s, 1H), 7.68 (d, J = 8.6 Hz, 2H), 7.46 (s, 1H), 7.17 (d, J = 7.7 Hz, 1H), 6.95 (d, J = 7.5 Hz, 1H), 6.56 (s, 1H), 4.65 (s, 2H), 3.40 (t, J = 5.8 Hz, 2H), 3.27 (s, 2H), 2.69 (t, J = 5.8 Hz, 2H), 2.29 (s, 3H). |

TABLE 1-continued

| Ex # | Chemical structure | Name | $^1$H NMR/LCMS |
|---|---|---|---|
| 025 | 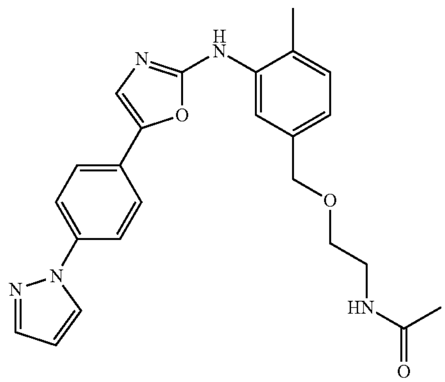 [SMILES: CC(=O)NCCOCc1ccc(C)c(Nc2ncc(-c3ccc(-n4cccn4)cc3)o2)c1] | N-(2-{4-Methyl-3-[5-(4-pyrazol-1-yl-phenyl)-oxazol-2-ylamino]-benzyloxy}-ethyl)-acetamide | $^1$H NMR (300 MHz, DMSO-d6) δ 9.30 (s, 1H), 8.54 (d, J = 2.3 Hz, 1H), 7.91 (d, J = 8.8 Hz, 3H), 7.84 (s, 1H), 7.76 (d, J = 1.5 Hz, 1H), 7.68 (d, J = 8.7 Hz, 2H), 7.46 (s, 1H), 7.18 (d, J = 7.7 Hz, 1H), 6.96 (d, J = 7.6 Hz, 1H), 6.60-6.53 (m, 1H), 4.44 (s, 2H), 3.42 (t, J = 5.9 Hz, 2H), 3.23 (dd, J = 11.5, 5.8 Hz, 2H), 2.29 (s, 3H), 1.78 (s, 3H). |
| 026 | 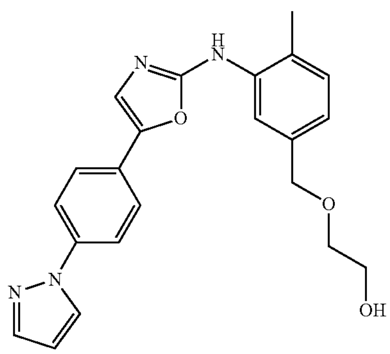 [SMILES: Cc1ccc(COCCO)cc1Nc1ncc(-c2ccc(-n3cccn3)cc2)o1] | 2-{4-Methyl-3-[5-(4-pyrazol-1-yl-phenyl)-oxazol-2-ylamino]-benzyloxy}-ethanol | $^1$H NMR (300 MHz, DMSO-d6) δ 9.30 (s, 1H), 8.53 (d, J = 2.4 Hz, 1H), 7.91 (d, J = 8.8 Hz, 2H), 7.83 (br s, 1H), 7.76 (d, J = 1.6 Hz, 1H), 7.68 (d, J = 8.8 Hz, 2H), 7.46 (s, 1H), 7.17 (d, J = 7.7 Hz, 1H), 6.96 (dd, J = 7.6, 1.3 Hz, 1H), 6.59-6.51 (m, 1H), 4.63 (t, J = 5.4 Hz, 1H), 4.46 (s, 2H), 3.61-3.49 (m, 2H), 3.46 (m, 2H), 2.29 (s, 3H). |
| 027 | 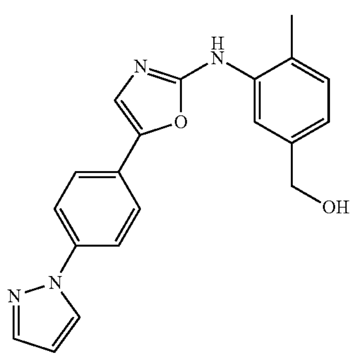 [SMILES: Cc1ccc(CO)cc1Nc1ncc(-c2ccc(-n3cccn3)cc2)o1] | {4-Methyl-3-[5-(4-pyrazol-1-yl-phenyl)-oxazol-2-ylamino]-phenyl}-methanol | $^1$H NMR (300 MHz, DMSO-d6) δ 9.26 (s, 1H), 8.53 (d, J = 2.1 Hz, 1H), 7.91 (d, J = 8.8 Hz, 2H), 7.82 (s, 1H), 7.76 (s, 1H), 7.68 (d, J = 8.7 Hz, 2H), 7.46 (s, 1H), 7.14 (d, J = 7.5 Hz, 1H), 6.94 (d, J = 7.6 Hz, 1H), 6.56 (s, 1H), 5.15 (t, J = 5.7 Hz, 1H), 4.47 (d, J = 5.4 Hz, 2H), 2.27 (s, 3H). |
| 028 | 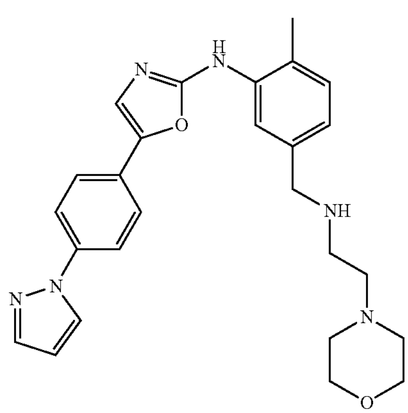 [SMILES: Cc1ccc(CNCCN2CCOCC2)cc1Nc1ncc(-c2ccc(-n3cccn3)cc2)o1] | {2-Methyl-5-[(2-morpholin-4-yl-ethylamino)-methyl]-phenyl}-[5-(4-pyrazol-1-yl-phenyl)-oxazol-2-yl]-amine | $^1$H NMR (300 MHz, DMSO-d6) δ 9.25 (s, 1H), 8.53 (d, J = 2.4 Hz, 1H), 7.91 (d, J = 8.8 Hz, 2H), 7.78 (d, J = 1.2 Hz, 1H), 7.76 (d, J = 1.6 Hz, 1H), 7.67 (d, J = 8.7 Hz, 2H), 7.45 (s, 1H), 7.13 (d, J = 7.7 Hz, 1H), 6.94 (dd, J = 7.6, 1.3 Hz, 1H), 6.60-6.52 (m, 1H), 3.66 (s, 2H), 3.57-3.48 (m, 4H), 2.58 (t, J = 6.4 Hz, 2H), 2.37 (t, J = 6.3 Hz, 2H), 2.34-2.28 (m, 4H), 2.26 (s, 3H). |

TABLE 1-continued

| Ex # | Chemical structure | Name | ¹H NMR/LCMS |
|---|---|---|---|
| 029 | 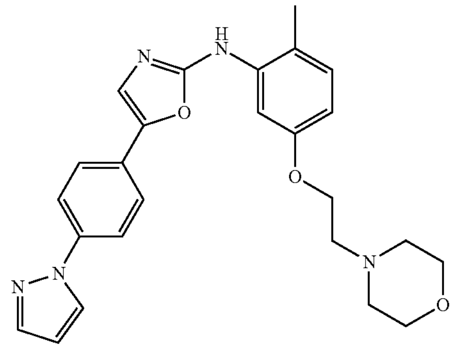 [SMILES: Cc1ccc(OCCN2CCOCC2)cc1Nc1ncc(-c2ccc(-n3cccn3)cc2)o1] | [2-Methyl-5-(2-morpholin-4-yl-ethoxy)-phenyl]-[5-(4-pyrazol-1-yl-phenyl)-oxazol-2-yl]-amine | ¹H NMR (300 MHz, DMSO-d6) δ 9.25 (s, 1H), 8.53 (d, J = 2.5 Hz, 1H), 7.92 (d, J = 8.7 Hz, 2H), 7.76 (d, J = 1.6 Hz, 1H), 7.69 (d, J = 8.6 Hz, 2H), 7.62 (d, J = 2.5 Hz, 1H), 7.48 (s, 1H), 7.07 (d, J = 8.4 Hz, 1H), 6.60-6.54 (m, 2H), 4.05 (t, J = 5.7 Hz, 2H), 3.61-3.54 (m, 4H), 2.69 (t, J = 5.7 Hz, 2H), 2.50-2.44 (m, 4H), 2.22 (s, 3H). |
| 030 | 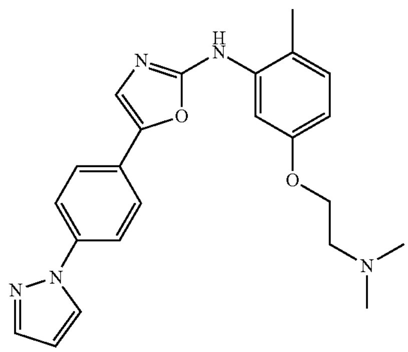 [SMILES: Cc1ccc(OCCN(C)C)cc1Nc1ncc(-c2ccc(-n3cccn3)cc2)o1] | [5-(2-Dimethylamino-ethoxy)-2-methyl-phenyl]-[5-(4-pyrazol-1-yl-phenyl)-oxazol-2-yl]-amine | ¹H NMR (300 MHz, DMSO-d6) δ 9.26 (s, 1H), 8.54 (d, J = 2.4 Hz, 1H), 7.92 (d, J = 8.8 Hz, 2H), 7.76 (d, J = 1.6 Hz, 1H), 7.69 (d, J = 8.8 Hz, 2H), 7.62 (d, J = 2.5 Hz, 1H), 7.48 (s, 1H), 7.07 (d, J = 8.4 Hz, 1H), 6.63-6.49 (m, 2H), 4.01 (t, J = 5.8 Hz, 2H), 2.64 (t, J = 5.8 Hz, 2H), 2.23 (s, 9H). |
| 031 | 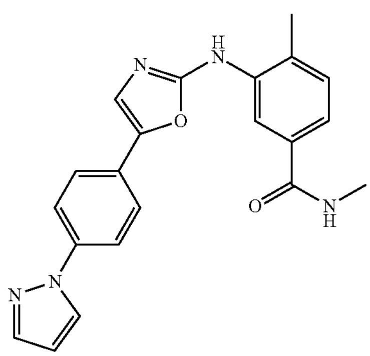 [SMILES: CNC(=O)c1ccc(C)c(Nc2ncc(-c3ccc(-n4cccn4)cc3)o2)c1] | 4,N-Dimethyl-3-[5-(4-pyrazol-1-yl-phenyl)-oxazol-2-ylamino]-benzamide | ¹H NMR (300 MHz, DMSO-d6) δ 9.40 (s, 1H), 8.54 (d, J = 2.4 Hz, 1H), 8.34 (s, 1H), 8.32 (d, J = 1.3 Hz, 1H), 7.92 (d, J = 8.8 Hz, 2H), 7.76 (d, J = 1.5 Hz, 1H), 7.69 (d, J = 8.7 Hz, 2H), 7.48 (s, 1H), 7.44 (dd, J = 7.8, 1.6 Hz, 1H), 7.27 (d, J = 7.9 Hz, 1H), 6.60-6.53 (m, 1H), 2.77 (d, J = 4.5 Hz, 3H), 2.33 (s, 3H). |
| 032 | 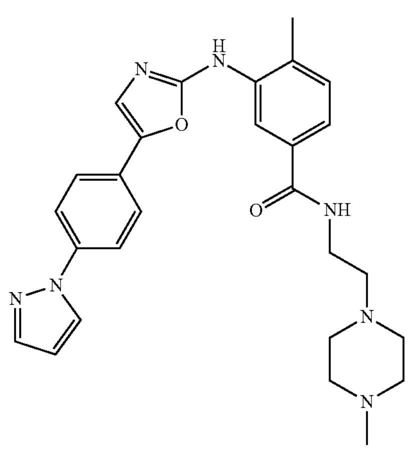 [SMILES: Cc1ccc(C(=O)NCCN2CCN(C)CC2)cc1Nc1ncc(-c2ccc(-n3cccn3)cc2)o1] | 4-Methyl-N-[2-(4-methyl-piperazin-1-yl)-ethyl]-3-[5-(4-pyrazol-1-yl-phenyl)-oxazol-2-ylamino]-benzamide | ¹H NMR (300 MHz, DMSO-d6) δ 9.41 (s, 1H), 8.54 (d, J = 2.5 Hz, 1H), 8.31 (s, 1H), 8.27 (t, J = 5.5 Hz, 1H), 7.92 (d, J = 8.7 Hz, 2H), 7.76 (d, J = 1.6 Hz, 1H), 7.69 (d, J = 8.7 Hz, 2H), 7.48 (s, 1H), 7.44 (dd, J = 7.9, 1.5 Hz, 1H), 7.28 (d, J = 7.9 Hz, 1H), 6.59-6.53 (m, 1H), 3.34 (m, 2H) 2.48-2.36 (m, 6H), 2.33 (s, 3H), 2.31-2.23 (m, 4H), 2.13 (s, 3H). |

TABLE 1-continued

| Ex # | Chemical structure | Name | ¹H NMR/LCMS |
|---|---|---|---|
| 033 | 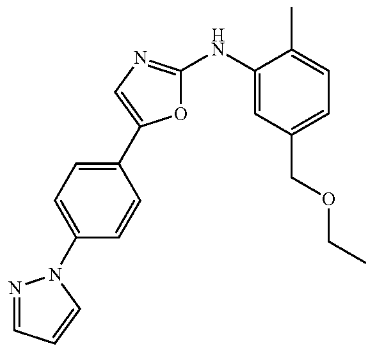 [SMILES: CCOCc1ccc(C)c(Nc2ncc(-c3ccc(-n4cccn4)cc3)o2)c1] | (5-Ethoxymethyl-2-methyl-phenyl)-[5-(4-pyrazol-1-yl-phenyl)-oxazol-2-yl]-amine | ¹H NMR (500 MHz, DMSO-d6) δ 9.27 (s, 1H), 8.52 (d, J = 2.4 Hz, 1H), 7.91 (d, J = 8.8 Hz, 2H), 7.83 (s, 1H), 7.76 (d, J = 1.6 Hz, 1H), 7.68 (d, J = 8.8 Hz, 2H), 7.46 (s, 1H), 7.16 (d, J = 7.7 Hz, 1H), 6.94 (dd, J = 7.6, 1.2 Hz, 1H), 6.57-6.53 (m, 1H), 4.42 (s, 2H), 3.48 (q, J = 7.0 Hz, 2H), 2.29 (s, 3H), 1.15 (t, J = 7.0 Hz, 3H). |
| 034 | 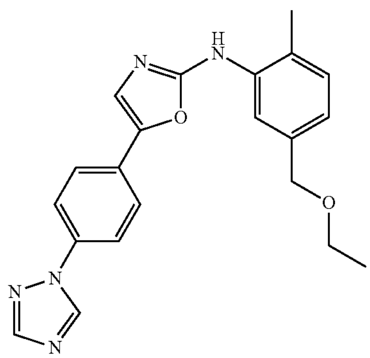 [SMILES: CCOCc1ccc(C)c(Nc2ncc(-c3ccc(-n4cncn4)cc3)o2)c1] | (5-Ethoxymethyl-2-methyl-phenyl)-[5-(4-[1,2,4]triazol-1-yl-phenyl)-oxazol-2-yl]-amine | ¹H NMR (300 MHz, DMSO-d6) δ 9.34 (s, 1H), 9.32 (s, 1H), 8.25 (s, 1H), 7.93 (d, J = 8.7 Hz, 2H), 7.82 (d, J = 1.1 Hz, 1H), 7.73 (d, J = 8.7 Hz, 2H), 7.53 (s, 1H), 7.17 (d, J = 7.7 Hz, 1H), 6.94 (dd, J = 7.6, 1.3 Hz, 1H), 4.42 (s, 2H), 3.48 (q, J = 7.0 Hz, 2H), 2.28 (s, 3H), 1.15 (t, J = 7.0 Hz, 3H). |
| 035 | 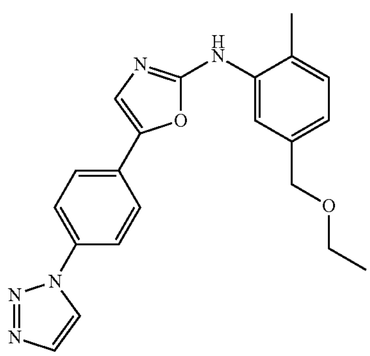 [SMILES: CCOCc1ccc(C)c(Nc2ncc(-c3ccc(-n4ccnn4)cc3)o2)c1] | (5-Ethoxymethyl-2-methyl-phenyl)-[5-(4-[1,2,3]triazol-1-yl-phenyl)-oxazol-2-yl]-amine | ¹H NMR (500 MHz, DMSO-d6) δ 9.35 (s, 1H), 8.86 (d, J = 1.1 Hz, 1H), 8.03-7.97 (m, 3H), 7.82 (d, J = 0.9 Hz, 1H), 7.77 (d, J = 8.8 Hz, 2H), 7.57 (s, 1H), 7.18 (d, J = 7.7 Hz, 1H), 6.96 (dd, J = 7.6, 1.4 Hz, 1H), 4.43 (s, 2H), 3.49 (q, J = 7.0 Hz, 2H), 2.30 (s, 3H), 1.16 (t, J = 7.0 Hz, 3H). |
| 036 | 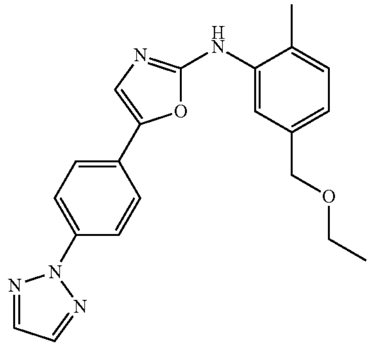 [SMILES: CCOCc1ccc(C)c(Nc2ncc(-c3ccc(-n4nccn4)cc3)o2)c1] | (5-Ethoxymethyl-2-methyl-phenyl)-[5-(4-[1,2,3]triazol-2-yl-phenyl)-oxazol-2-yl]-amine | ¹H NMR (500 MHz, DMSO-d6) δ 9.34 (s, J = 20.3 Hz, 1H), 8.14 (s, 2H), 8.09 (d, J = 8.8 Hz, 2H), 7.82 (s, 1H), 7.75 (d, J = 8.8 Hz, 2H), 7.52 (s, 1H), 7.18 (d, J = 7.7 Hz, 1H), 6.96 (dd, J = 7.6, 1.2 Hz, 1H), 4.43 (s, 2H), 3.49 (q, J = 7.0 Hz, 2H), 2.29 (s, 3H), 1.16 (t, J = 7.0 Hz, 3H). |

TABLE 1-continued

| Ex # | Chemical structure | Name | ¹H NMR/LCMS |
|---|---|---|---|
| 037 | 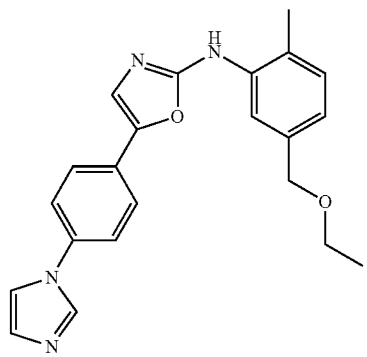 [SMILES: CCOCc1ccc(C)c(Nc2ncc(-c3ccc(-n4ccnc4)cc3)o2)c1] | (5-Ethoxymethyl-2-methyl-phenyl)-[5-(4-imidazol-1-yl-phenyl)-oxazol-2-yl]-amine | ¹H NMR (300 MHz, DMSO-d6) δ 9.31 (s, 1H), 8.30 (s, 1H), 7.82 (d, J = 1.2 Hz, 1H), 7.78 (t, J = 1.1 Hz, 1H), 7.73 (d, J = 8.9 Hz, 2H), 7.68 (d, J = 8.9 Hz, 2H), 7.50 (s, 1H), 7.17 (d, J = 7.7 Hz, 1H), 7.12 (s, 1H), 6.94 (dd, J = 7.6, 1.3 Hz, 1H), 4.41 (s, 2H), 3.48 (q, J = 7.0 Hz, 2H), 2.28 (s, 3H), 1.15 (t, J = 7.0 Hz, 3H). |
| 038 | 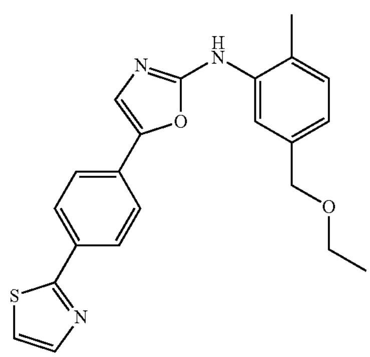 [SMILES: CCOCc1ccc(C)c(Nc2ncc(-c3ccc(-c4nccs4)cc3)o2)c1] | (5-Ethoxymethyl-2-methyl-phenyl)-[5-(4-thiazol-2-yl-phenyl)-oxazol-2-yl]-amine | ¹H NMR (300 MHz, DMSO-d6) δ 9.40 (s, 1H), 8.00 (d, J = 8.2 Hz, 2H), 7.93 (d, J = 3.1 Hz, 1H), 7.84-7.76 (m, 2H), 7.68 (d, J = 8.3 Hz, 2H), 7.56 (s, 1H), 7.17 (d, J = 7.6 Hz, 1H), 6.94 (d, J = 7.5 Hz, 1H), 4.41 (s, 2H), 3.47 (q, J = 7.0 Hz, 2H), 2.28 (s, 3H), 1.16 (q, J = 6.6 Hz, 3H). |
| 039 | 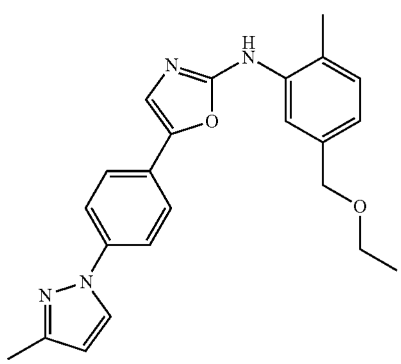 [SMILES: CCOCc1ccc(C)c(Nc2ncc(-c3ccc(-n4ccc(C)n4)cc3)o2)c1] | (5-Ethoxymethyl-2-methyl-phenyl)-{5-[4-(3-methyl-pyrazol-1-yl)-phenyl]-oxazol-2-yl}-amine | ¹H NMR (500 MHz, DMSO-d6) δ 9.25 (s, 1H), 8.39 (d, J = 2.4 Hz, 1H), 7.85 (d, J = 8.8 Hz, 2H), 7.83 (s, 1H), 7.65 (d, J = 8.8 Hz, 2H), 7.43 (s, 1H), 7.16 (d, J = 7.7 Hz, 1H), 6.94 (dd, J = 7.6, 1.3 Hz, 1H), 6.34 (d, J = 2.3 Hz, 1H), 4.42 (s, 2H), 3.48 (q, J = 7.0 Hz, 2H), 2.28 (s, 3H), 2.28 (s, 3H), 1.15 (t, J = 7.0 Hz, 3H). |
| 040 | 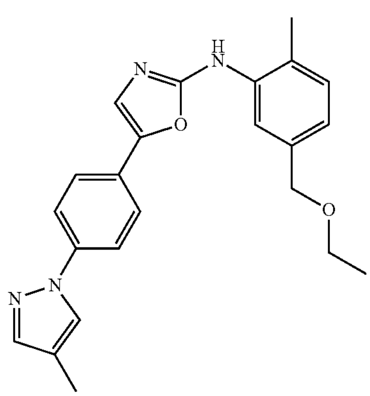 [SMILES: CCOCc1ccc(C)c(Nc2ncc(-c3ccc(-n4cc(C)cn4)cc3)o2)c1] | (5-Ethoxymethyl-2-methyl-phenyl)-{5-[4-(4-methyl-pyrazol-1-yl)-phenyl]-oxazol-2-yl}-amine | ¹H NMR (500 MHz, DMSO-d6) δ 9.25 (s, 1H), 8.29 (s, 1H), 7.87-7.80 (m, 3H), 7.66 (d, J = 8.8 Hz, 2H), 7.57 (s, 1H), 7.43 (s, 1H), 7.16 (d, J = 7.7 Hz, 1H), 6.94 (dd, J = 7.6, 1.3 Hz, 1H), 4.42 (s, 2H), 3.49 (q, J = 7.0 Hz, 2H), 2.28 (s, 3H), 2.11 (s, 3H), 1.15 (t, J = 7.0 Hz, 3H). |

TABLE 1-continued

| Ex # | Chemical structure | Name | $^1$H NMR/LCMS |
|---|---|---|---|
| 041 | 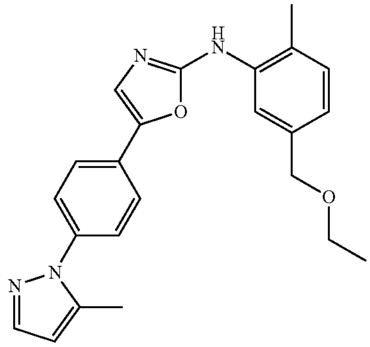 [SMILES: CCOCc1ccc(C)c(Nc2ncc(-c3ccc(-n4nccc4C)cc3)o2)c1] | (5-Ethoxymethyl-2-methyl-phenyl)-{5-[4-(5-methyl-pyrazol-1-yl)-phenyl]-oxazol-2-yl}-amine | $^1$H NMR (500 MHz, CDCl$_3$) δ 8.00 (d, J = 1.1 Hz, 1H), 7.63 (d, J = 8.7 Hz, 2H), 7.59 (d, J = 1.6 Hz, 1H), 7.48 (d, J = 8.7 Hz, 2H), 7.20 (s, 1H), 7.18 (d, J = 7.7 Hz, 1H), 7.02 (dd, J = 7.6, 1.3 Hz, 1H), 6.77 (s, 1H), 6.21 (dd, J = 1.6, 0.7 Hz, 1H), 4.54 (s, 2H), 3.57 (q, J = 7.0 Hz, 2H), 2.38 (s, 3H), 2.34 (s, 3H), 1.26 (t, J = 7.0 Hz, 3H). |
| 042 | 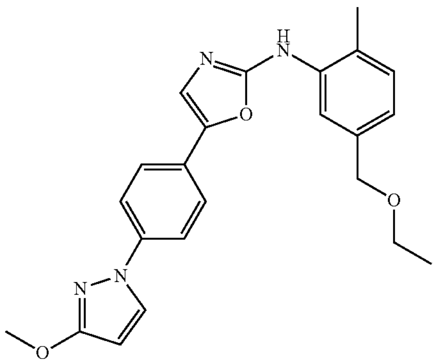 [SMILES: CCOCc1ccc(C)c(Nc2ncc(-c3ccc(-n4ccc(OC)n4)cc3)o2)c1] | (5-Ethoxymethyl-2-methyl-phenyl)-{5-[4-(3-methoxy-pyrazol-1-yl)-phenyl]-oxazol-2-yl}-amine | $^1$H NMR (500 MHz, DMSO-d6) δ 9.25 (s, 1H), 8.37 (d, J = 2.6 Hz, 1H), 7.83 (s, 1H), 7.79 (d, J = 8.8 Hz, 2H), 7.64 (d, J = 8.8 Hz, 2H), 7.41 (s, 1H), 7.16 (d, J = 7.7 Hz, 1H), 6.93 (d, J = 7.6 Hz, 1H), 6.04 (d, J = 2.6 Hz, 1H), 4.41 (s, 2H), 3.89 (s, 3H), 3.48 (q, J = 7.0 Hz, 2H), 2.28 (s, 3H), 1.15 (t, J = 7.0 Hz, 3H). |
| 043 | 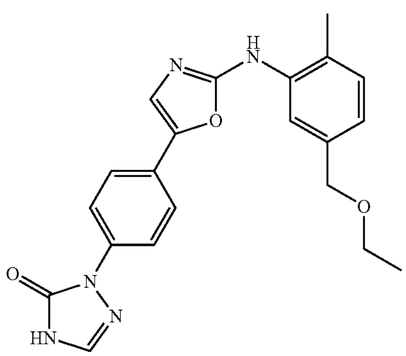 [SMILES: CCOCc1ccc(C)c(Nc2ncc(-c3ccc(-n4nc[nH]c4=O)cc3)o2)c1] | 2-{4-[2-(5-Ethoxymethyl-(2-methyl-phenylamino))-oxazol-5-yl]-phenyl}-2,4-dihydro-[1,2,4]triazol-3-one | $^1$H NMR (500 MHz, DMSO-d6) δ 9.25 (s, 1H), 8.11 (s, 1H), 7.95 (d, J = 8.9 Hz, 2H), 7.82 (d, J = 1.1 Hz, 1H), 7.64 (d, J = 8.8 Hz, 2H), 7.38 (s, 1H), 7.16 (d, J = 7.7 Hz, 1H), 6.93 (dd, J = 7.6, 1.3 Hz, 1H), 4.41 (s, 2H), 3.47 (q, J = 7.0 Hz, 2H), 2.27 (s, 3H), 1.14 (t, J = 7.0 Hz, 3H). |
| 044 | 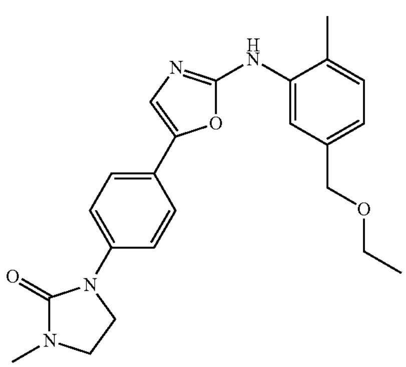 [SMILES: CCOCc1ccc(C)c(Nc2ncc(-c3ccc(N4CCN(C)C4=O)cc3)o2)c1] | 1-{4-[2-(5-Ethoxymethyl-(2-methyl-phenylamino))-oxazol-5-yl]-phenyl}-3-methyl-imidazolidin-2-one | $^1$H NMR (500 MHz, DMSO-d6) δ 9.15 (s, 1H), 7.82 (s, 1H), 7.63 (d, J = 8.9 Hz, 2H), 7.51 (d, J = 8.9 Hz, 2H), 7.27 (s, 1H), 7.15 (d, J = 7.7 Hz, 1H), 6.92 (dd, J = 7.6, 1.3 Hz, 1H), 4.41 (s, 2H), 3.83-3.76 (m, 2H), 3.52-3.41 (m, 4H), 2.77 (s, 3H), 2.27 (s, 3H), 1.14 (t, J = 7.0 Hz, 3H). |

TABLE 1-continued

| Ex # | Chemical structure | Name | $^1$H NMR/LCMS |
|---|---|---|---|
| 045 | 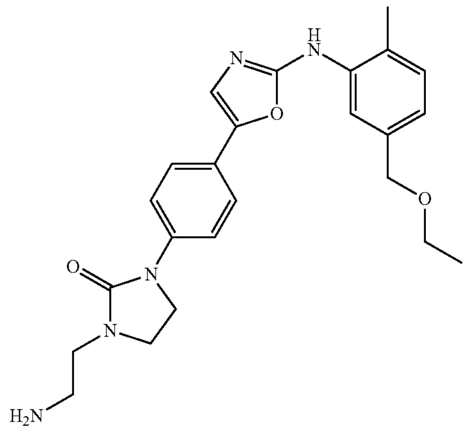 [SMILES: CCOCc1ccc(C)c(Nc2ncc(-c3ccc(N4CCN(CCN)C4=O)cc3)o2)c1] | 1-(2-Amino-ethyl)-3-{4-[2-(5-ethoxymethyl-(2-methyl-phenylamino))-oxazol-5-yl]-phenyl}-imidazolidin-2-one | $^1$H NMR (500 MHz, DMSO-d6) δ 9.17 (s, 1H), 7.83 (d, J = 1.2 Hz, 1H), 7.63 (d, J = 8.9 Hz, 2H), 7.51 (d, J = 8.9 Hz, 2H), 7.27 (s, J = 4.5 Hz, 1H), 7.15 (d, J = 7.7 Hz, 1H), 6.92 (dd, J = 7.6, 1.3 Hz, 1H), 4.41 (s, 2H), 3.81 (dd, J = 9.3, 6.7 Hz, 2H), 3.50 (dd, J = 10.1, 6.1 Hz, 2H), 3.48 (q, J = 7.0 Hz, 2H), 3.18 (t, J = 6.5 Hz, 2H), 2.69 (t, J = 6.5 Hz, 2H), 2.27 (s, 3H), 1.56 (s, 2H), 1.15 (t, J = 7.0 Hz, 3H). |
| 046 | 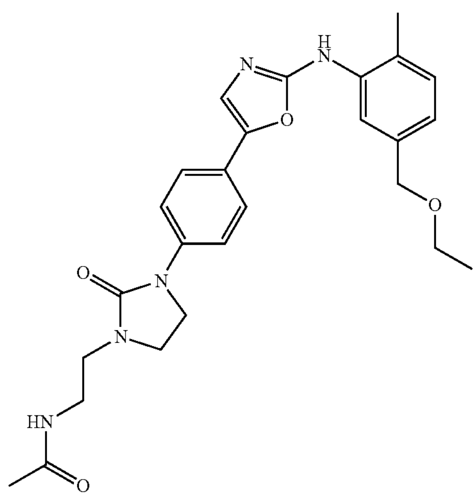 [SMILES: CCOCc1ccc(C)c(Nc2ncc(-c3ccc(N4CCN(CCNC(C)=O)C4=O)cc3)o2)c1] | N-[2-(3-{4-[2-(5-Ethoxymethyl-(2-methyl-phenylamino))-oxazol-5-yl]-phenyl}-2-oxo-imidazolidin-1-yl)-ethyl]-acetamide | $^1$H NMR (500 MHz, DMSO-d6) δ 9.15 (s, 1H), 7.92 (s, 1H), 7.82 (br s, 1H), 7.63 (d, J = 9.0 Hz, 2H), 7.52 (d, J = 8.9 Hz, 2H), 7.27 (s, 1H), 7.15 (d, J = 7.7 Hz, 1H), 6.92 (dd, J = 7.7, 1.4 Hz, 1H), 4.41 (s, 2H), 3.84-3.75 (m, 2H), 3.54-3.49 (m, 2H), 3.47 (q, J = 7.0 Hz, 2H), 3.23 (t, J = 5.4 Hz, 4H), 2.27 (s, 3H), 1.79 (s, 3H), 1.14 (t, J = 7.0 Hz, 3H). |
| 047 | 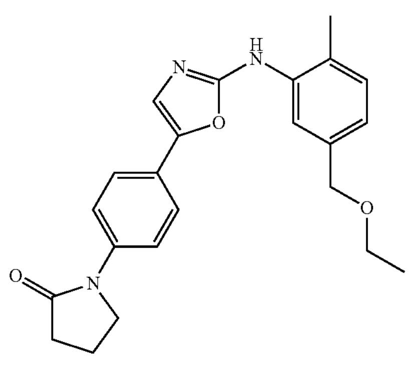 [SMILES: CCOCc1ccc(C)c(Nc2ncc(-c3ccc(N4CCCC4=O)cc3)o2)c1] | 1-{4-[2-(5-Ethoxymethyl-(2-methyl-phenylamino))-oxazol-5-yl]-phenyl}-pyrrolidin-2-one | $^1$H NMR (500 MHz, DMSO-d6) δ 9.21 (s, 1H), 7.82 (br s, 1H), 7.74 (d, J = 8.9 Hz, 2H), 7.57 (d, J = 8.8 Hz, 2H), 7.34 (s, 1H), 7.16 (d, J = 7.7 Hz, 1H), 6.92 (dd, J = 7.6, 1.4 Hz, 1H), 4.41 (s, 2H), 3.85 (t, J = 7.0 Hz, 2H), 3.48 (q, J = 7.0 Hz, 2H), 2.56-2.48 (m, 2H), 2.27 (s, 3H), 2.12-2.01 (m, 2H), 1.14 (t, J = 7.0 Hz, 3H). |

TABLE 1-continued

| Ex # | Chemical structure | Name | ¹H NMR/LCMS |
|---|---|---|---|
| 048 | 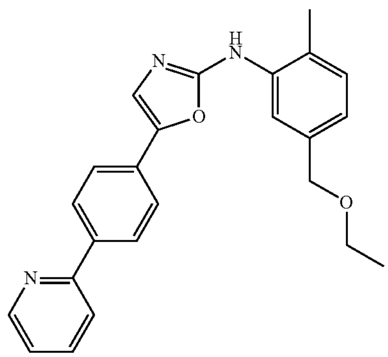 [SMILES: CCOCc1ccc(C)c(Nc2ncc(-c3ccc(-c4ccccn4)cc3)o2)c1] | (5-Ethoxymethyl-2-methyl-phenyl)-[5-(4-pyridin-2-yl-phenyl)-oxazol-2-yl]-amine | ¹H NMR (500 MHz, DMSO-d6) δ 9.31 (s, 1H), 8.67 (d, J = 3.9 Hz, 1H), 8.16 (d, J = 8.4 Hz, 2H), 7.99 (d, J = 7.8 Hz, 1H), 7.88 (td, J = 7.6, 1.6 Hz, 1H), 7.83 (s, 1H), 7.68 (d, J = 8.3 Hz, 2H), 7.52 (s, 1H), 7.35 (dd, J = 7.2, 5.0 Hz, 1H), 7.17 (d, J = 7.6 Hz, 1H), 6.95 (d, J = 7.0 Hz, 1H), 4.42 (s, 2H), 3.49 (q, J = 7.0 Hz, 2H), 2.29 (s, 3H), 1.15 (t, J = 7.0 Hz, 3H). |
| 049 | 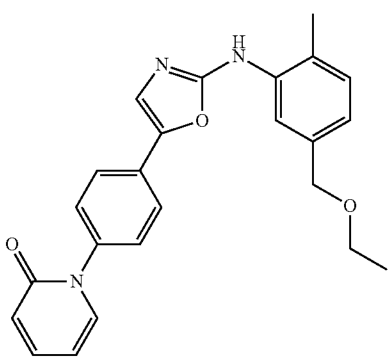 [SMILES: CCOCc1ccc(C)c(Nc2ncc(-c3ccc(-n4ccccc4=O)cc3)o2)c1] | 1-{4-[2-(5-Ethoxymethyl-(2-methyl-phenylamino))-oxazol-5-yl]-phenyl}-1H-pyridin-2-one | ¹H NMR (500 MHz, DMSO-d6) δ 9.32 (s, 1H), 7.81 (d, J = 1.1 Hz, 1H), 7.71-7.65 (m, 3H), 7.55-7.48 (m, 2H), 7.47 (d, J = 8.6 Hz, 2H), 7.17 (d, J = 7.7 Hz, 1H), 6.95 (dd, J = 7.6, 1.4 Hz, 1H), 6.49 (d, J = 8.8 Hz, 1H), 6.32 (td, J = 6.7, 1.3 Hz, 1H), 4.42 (s, 2H), 3.48 (q, J = 7.0 Hz, 2H), 2.29 (s, 3H), 1.16 (t, J = 7.0 Hz, 3H). |
| 050 | 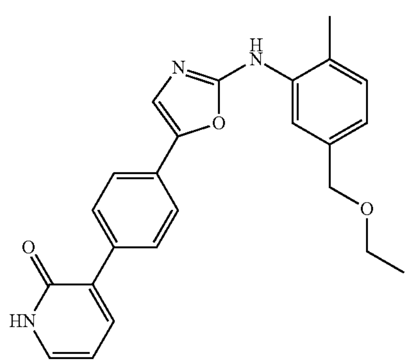 [SMILES: CCOCc1ccc(C)c(Nc2ncc(-c3ccc(-c4ccc[nH]c4=O)cc3)o2)c1] | 3-{4-[2-(5-Ethoxymethyl-(2-methyl-phenylamino))-oxazol-5-yl]-phenyl}-1H-pyridin-2-one | ¹H NMR (500 MHz, DMSO-d6) δ 11.80 (s, 1H), 9.27 (s, 1H), 7.90-7.78 (m, 3H), 7.71 (dd, J = 6.9, 2.0 Hz, 1H), 7.57 (d, J = 8.5 Hz, 2H), 7.44 (s, 1H), 7.39 (dd, J = 6.4, 2.0 Hz, 1H), 7.16 (d, J = 7.7 Hz, 1H), 6.94 (dd, J = 7.6, 1.0 Hz, 1H), 6.30 (t, J = 6.7 Hz, 1H), 4.42 (s, 2H), 3.48 (q, J = 7.0 Hz, 2H), 2.28 (s, 3H), 1.15 (t, J = 7.0 Hz, 3H). |
| 051 | 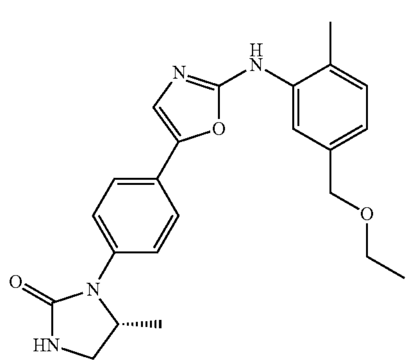 [SMILES: CCOCc1ccc(C)c(Nc2ncc(-c3ccc(N4C(=O)NC[C@H]4C)cc3)o2)c1] | (R)-1-(4-(2-((5-(ethoxymethyl)-2-methylphenyl)amino)oxazol-5-yl)phenyl)-5-methyl-imidazolidin-2-one | ¹H NMR (500 MHz, Chloroform-d) δ 8.03 (s, 1H), 7.59-7.46 (m, 4H), 7.20 (d, J = 7.7 Hz, 1H), 7.12 (s, 1H), 7.06-6.97 (m, 1H), 6.63 (s, 1H), 4.56 (s, 2H), 4.54-4.46 (m, 2H), 3.80-3.73 (m, 2H), 3.59 (q, J = 7.0 Hz, 2H), 2.35 (s, 3H), 1.37 (dd, J = 6.2, 4.1 Hz, 3H), 1.28 (t, J = 7.0 Hz, 3H). |

TABLE 1-continued

| Ex # | Chemical structure | Name | ¹H NMR/LCMS |
|---|---|---|---|
| 052 | 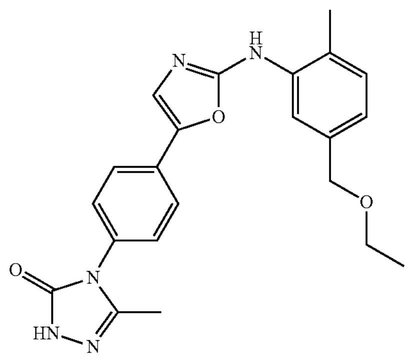 [SMILES: CCOCc1ccc(C)c(Nc2ncc(-c3ccc(-n4c(C)n[nH]c4=O)cc3)o2)c1] | 4-(4-(2-((5-(ethoxymethyl)-2-methylphenyl)amino)oxazol-5-yl)phenyl)-5-methyl-2,4-dihydro-3H-1,2,4-triazol-3-one | ¹H NMR (500 MHz, DMSO-d₆) δ 11.62 (s, 1H), 9.33 (s, 1H), 7.81 (s, 1H), 7.73-7.66 (m, 2H), 7.53 (s, 1H), 7.50-7.44 (m, 2H), 7.18 (d, J = 7.6 Hz, 1H), 6.99-6.93 (m, 1H), 4.43 (s, 2H), 3.53-3.33 (m, 2H), 2.29 (s, 3H), 2.10 (s, 3H), 1.16 (t, J = 7.0 Hz, 3H). |
| 053 | 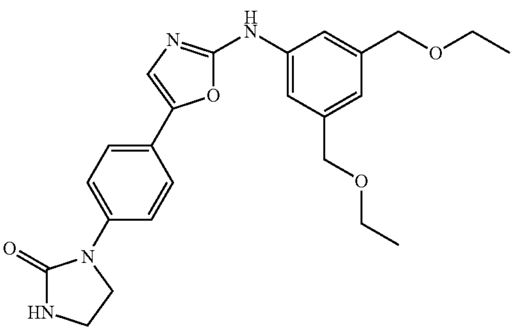 [SMILES: CCOCc1cc(COCC)cc(Nc2ncc(-c3ccc(N4CCNC4=O)cc3)o2)c1] | 1-(4-(2-((3,5-bis(ethoxymethyl)phenyl)amino)oxazol-5-yl)phenyl)imidazolidin-2-one | ¹H NMR (500 MHz, DMSO-d₆) δ 10.26 (s, 1H), 7.67-7.58 (m, 2H), 7.53 (dd, J = 5.2, 3.7 Hz, 4H), 7.33 (s, 1H), 7.01 (s, 1H), 6.85 (s, 1H), 4.44 (s, 4H), 3.92-3.85 (m, 2H), 3.51 (q, J = 7.0 Hz, 4H), 3.43 (m, 2H), 1.18 (t, J = 7.0 Hz, 6H). |
| 054 | 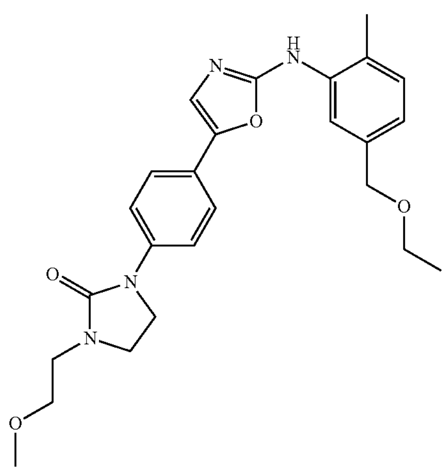 [SMILES: CCOCc1ccc(C)c(Nc2ncc(-c3ccc(N4CCN(CCOC)C4=O)cc3)o2)c1] | 1-(4-(2-((5-(ethoxymethyl)-2-methylphenyl)amino)oxazol-5-yl)phenyl)-3-(2-methoxyethyl)imidazolidin-2-one | ¹H NMR (500 MHz, DMSO-d₆) δ 9.16 (s, 1H), 7.84 (d, J = 1.7 Hz, 1H), 7.67-7.61 (m, 2H), 7.53 (d, J = 8.9 Hz, 2H), 7.29 (s, 1H), 7.16 (d, J = 7.6 Hz, 1H), 6.96-6.90 (m, 1H), 4.42 (s, 2H), 3.83 (dd, J = 9.2, 6.8 Hz, 2H), 3.57-3.44 (m, 5H), 3.37 (t, J = 5.5 Hz, 2H), 2.28 (s, 3H), 1.16 (t, J = 7.0 Hz, 3H). |
| 055 | 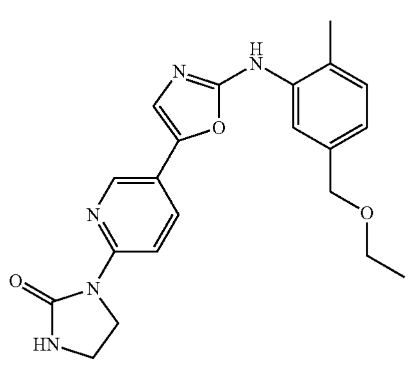 [SMILES: CCOCc1ccc(C)c(Nc2ncc(-c3ccc(N4CCNC4=O)nc3)o2)c1] | 1-(5-(2-((5-(ethoxymethyl)-2-methylphenyl)amino)oxazol-5-yl)pyridin-2-yl)imidazolidin-2-one | ¹H NMR (500 MHz, Chloroform-d) δ 8.49 (dd, J = 2.4, 0.9 Hz, 1H), 8.32 (dd, J = 9.0, 0.8 Hz, 1H), 7.98 (d, J = 1.6 Hz, 1H), 7.76 (dd, J = 8.9, 2.4 Hz, 1H), 7.18 (d, J = 7.7 Hz, 1H), 7.11 (s, 1H), 7.01 (d, J = 7.0 Hz, 1H), 6.67 (s, 1H), 4.53 (s, 2H), 4.20 (dd, J = 8.8, 7.3 Hz, 2H), 3.63-3.53 (m, 4H), 2.33 (s, 3H), 1.26 (t, J = 7.0 Hz, 3H). |

TABLE 1-continued

| Ex # | Chemical structure | Name | ¹H NMR/LCMS |
|---|---|---|---|
| 056 | 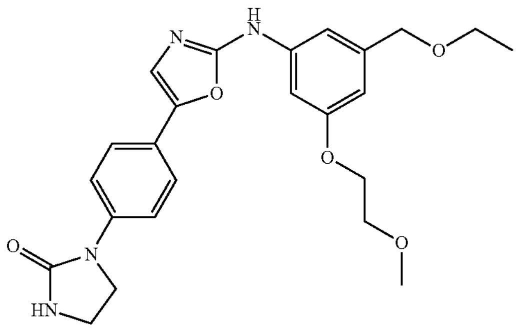 [SMILES: CCOCc1cc(Nc2ncc(-c3ccc(N4CCNC4=O)cc3)o2)cc(OCCOC)c1] | 1-(4-(2-((3-(ethoxymethyl)-5-(2-methoxyethoxy)phenyl)amino)oxazol-5-yl)phenyl)imidazolidin-2-one | ¹H NMR (500 MHz, Chloroform-d) δ 7.61 (d, J = 8.8 Hz, 2H), 7.53 (d, J = 8.8 Hz, 2H), 7.21 (t, J = 2.3 Hz, 1H), 7.09 (s, 1H), 7.02 (s, 1H), 6.97 (s, 1H), 6.65 (s, 1H), 4.51 (s, 2H), 4.22-4.17 (m, 2H), 4.03-3.96 (m, 2H), 3.79 (dd, J = 5.6, 3.9 Hz, 2H), 3.66-3.54 (m, 4H), 3.49 (s, 3H), 1.28 (td, J = 7.1, 1.6 Hz, 3H). |
| 057 | 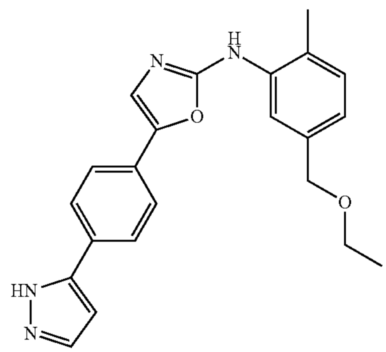 [SMILES: CCOCc1ccc(C)c(Nc2ncc(-c3ccc(-c4ccn[nH]4)cc3)o2)c1] | 5-(4-(1H-pyrazol-5-yl)phenyl)-N-(5-(ethoxymethyl)-2-methylphenyl)oxazol-2-amine | ¹H NMR (500 MHz, Chloroform-d) δ 7.97 (d, J = 4.2 Hz, 1H), 7.78 (dd, J = 8.4, 2.6 Hz, 2H), 7.64 (t, J = 2.3 Hz, 1H), 7.57 (dq, J = 6.3, 2.5, 1.8 Hz, 2H), 7.23-7.17 (m, 2H), 7.04 (dd, J = 7.7, 1.6 Hz, 1H), 6.65 (t, J = 2.3 Hz, 1H), 4.55 (s, 2H), 3.60 (q, J = 7.0 Hz, 2H), 2.35 (s, 3H), 1.29 (t, J = 7.0 Hz, 3H). |
| 058 | 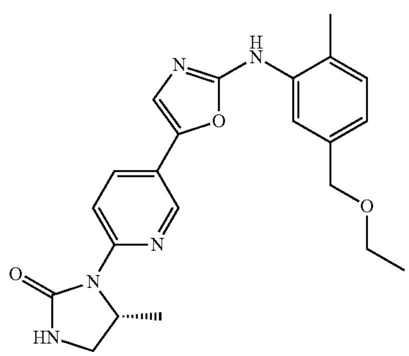 [SMILES: CCOCc1ccc(C)c(Nc2ncc(-c3ccc(N4C(=O)NC[C@H]4C)nc3)o2)c1] | (R)-1-(5-(2-((5-(ethoxymethyl)-2-methylphenyl)amino)oxazol-5-yl)pyridin-2-yl)-5-methyl-imidazolidin-2-one | ¹H NMR (500 MHz, Chloroform-d) δ 8.42 (d, J = 2.4 Hz, 1H), 8.16 (d, J = 8.8 Hz, 1H), 7.89 (d, J = 1.6 Hz, 1H), 7.67 (dd, J = 8.8, 2.5 Hz, 1H), 7.17-7.08 (m, 1H), 7.03 (s, 1H), 6.94 (dd, J = 7.7, 1.7 Hz, 1H), 6.83 (s, 1H), 4.82 (dqd, J = 9.7, 6.2, 3.6 Hz, 1H), 4.46 (s, 2H), 3.66 (td, J = 8.5, 1.1 Hz, 2H), 3.50 (q, J = 7.0 Hz, 2H), 2.26 (s, 3H), 1.38 (d, J = 6.2 Hz, 3H), 1.19 (t, J = 7.0 Hz, 3H). |
| 059 | 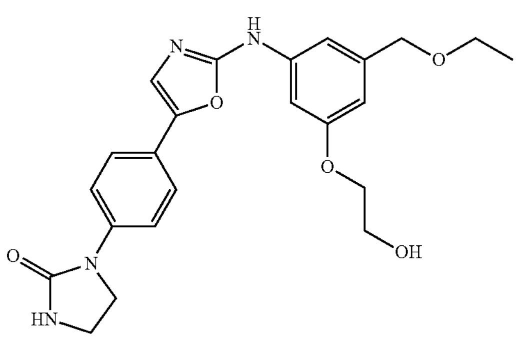 [SMILES: CCOCc1cc(Nc2ncc(-c3ccc(N4CCNC4=O)cc3)o2)cc(OCCO)c1] | 1-(4-(2-((3-(ethoxymethyl)-5-(2-hydroxy-ethoxy)phenyl)amino)oxazol-5-yl)phenyl)imidazolidin-2-one | ¹H NMR (500 MHz, Chloroform-d) δ 7.52 (d, J = 8.8 Hz, 2H), 7.44 (d, J = 8.9 Hz, 2H), 7.40 (s, 1H), 7.00 (s, 1H), 6.88 (s, 1H), 6.55 (s, 1H), 4.42 (s, 2H), 4.06 (dd, J = 9.5, 5.1 Hz, 4H), 3.91 (t, J = 7.8 Hz, 2H), 3.57-3.45 (m, 4H), 1.23-1.16 (m, 3H). |

TABLE 1-continued

| Ex # | Chemical structure | Name | $^1$H NMR/LCMS |
|---|---|---|---|
| 060 | 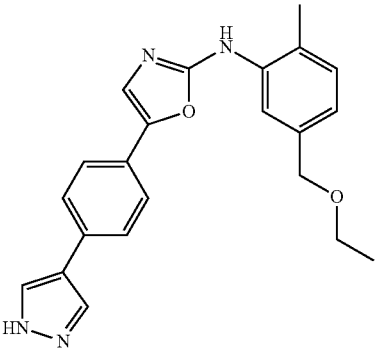 [SMILES: CCOCc1ccc(C)c(Nc2ncc(-c3ccc(-c4cn[nH]c4)cc3)o2)c1] | 5-(4-(1H-pyrazol-4-yl)phenyl)-N-(5-(ethoxymethyl)-2-methylphenyl)oxazol-2-amine | $^1$H NMR (500 MHz, Chloroform-d) δ 7.63 (d, J = 1.6 Hz, 2H), 7.60-7.55 (m, 2H), 7.41 (s, 2H), 7.36-7.30 (m, 3H), 7.09 (s, 1H), 6.26 (d, J = 1.9 Hz, 2H), 4.47 (s, 2H), 3.50 (q, J = 7.0 Hz, 2H), 2.27 (s, 3H), 1.19 (t, J = 7.0 Hz, 3H). |
| 061 | 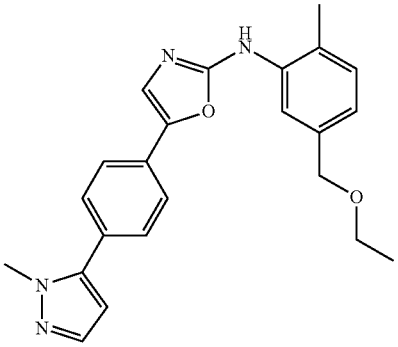 [SMILES: CCOCc1ccc(C)c(Nc2ncc(-c3ccc(-c4ccnn4C)cc3)o2)c1] | N-(5-(ethoxymethyl)-2-methylphenyl)-5-(4-(1-methyl-1H-pyrazol-5-yl)phenyl)oxazol-2-amine | $^1$H NMR (500 MHz, Chloroform-d) δ 7.92 (d, J = 1.7 Hz, 1H), 7.64-7.51 (m, 2H), 7.45 (s, 1H), 7.42-7.33 (m, 3H), 7.21-7.09 (m, 2H), 6.95 (dd, J = 7.7, 1.7 Hz, 1H), 6.26 (d, J = 1.9 Hz, 1H), 4.47 (s, 2H), 3.85 (s, 3H), 3.50 (q, J = 7.0 Hz, 2H), 2.27 (s, 3H), 1.19 (t, J = 7.0 Hz, 3H). |
| 062 | 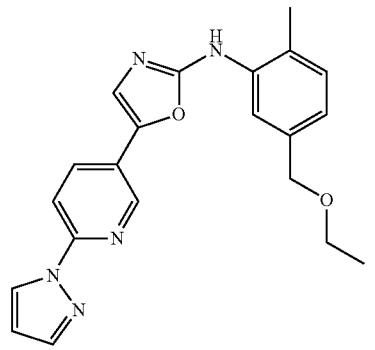 [SMILES: CCOCc1ccc(C)c(Nc2ncc(-c3ccc(-n4cccn4)nc3)o2)c1] | 4-(6-(1H-pyrazol-1-yl)pyridin-3-yl)-N-(5-(ethoxymethyl)-2-methylphenyl)thiazol-2-amine | $^1$H NMR (500 MHz, DMSO-d$_6$) δ 9.47 (s, 1H), 8.97 (dd, J = 2.3, 0.9 Hz, 1H), 8.64 (dd, J = 2.6, 0.8 Hz, 1H), 8.40 (dd, J = 8.5, 2.2 Hz, 1H), 8.06 (d, J = 1.8 Hz, 1H), 7.96 (dd, J = 8.5, 0.9 Hz, 1H), 7.85 (dd, J = 1.7, 0.8 Hz, 1H), 7.48 (s, 1H), 7.21 (d, J = 7.7 Hz, 1H), 6.97 (dd, J = 7.7, 1.7 Hz, 1H), 6.60 (dd, J = 2.6, 1.6 Hz, 1H), 4.47 (s, 2H), 3.53 (q, J = 6.9 Hz, 2H), 2.30 (s, 3H), 1.20 (t, J = 7.1 Hz, 3H). |
| 063 | 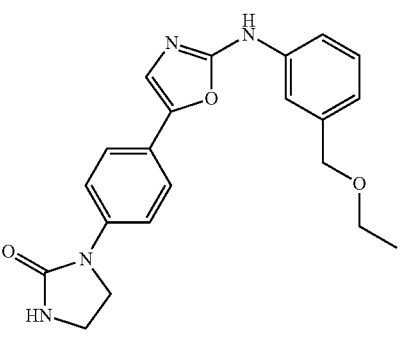 [SMILES: CCOCc1cccc(Nc2ncc(-c3ccc(N4CCNC4=O)cc3)o2)c1] | 1-(4-(2-((3-(ethoxymethyl)phenyl)amino)oxazol-5-yl)phenyl)imidazolidin-2-one | $^1$H NMR (500 MHz, DMSO-d$_6$) δ 10.26 (s, 1H), 7.64 (d, J = 8.9 Hz, 3H), 7.53 (d, J = 7.7 Hz, 3H), 7.33 (s, 1H), 7.28 (t, J = 7.8 Hz, 1H), 7.02 (s, 1H), 6.90 (d, J = 7.5 Hz, 1H), 4.45 (s, 2H), 3.89 (s, 2H), 3.51 (d, J = 7.1 Hz, 2H), 3.43 (s, 2H), 1.18 (t, J = 7.2 Hz, 3H). |

TABLE 1-continued

| Ex # | Chemical structure | Name | ¹H NMR/LCMS |
|---|---|---|---|
| 064 | 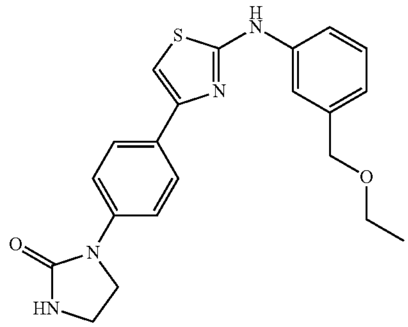 [SMILES: CCOCc1cccc(Nc2nc(-c3ccc(N4CCNC4=O)cc3)cs2)c1] | 1-(4-(2-((3-(ethoxymethyl)phenyl)amino)thiazol-4-yl)phenyl)imidazolidin-2-one | ¹H NMR (500 MHz, DMSO-d$_6$) δ 10.24 (s, 1H), 7.87 (d, J = 8.8 Hz, 2H), 7.79 (s, 1H), 7.61 (t, J = 8.2 Hz, 3H), 7.31 (t, J = 7.8 Hz, 1H), 7.20 (s, 1H), 6.98 (s, 1H), 6.90 (d, J = 7.6 Hz, 1H), 4.49 (s, 2H), 3.93-3.86 (m, 2H), 3.54 (q, J = 7.0 Hz, 2H), 3.47-3.40 (m, 2H), 3.30 (s, 2H), 1.24-1.14 (m, 3H). |

Where one or more chiral centers are present in a compound, mixtures of enantiomers or diastereomers may be present. Such compounds may be used as pharmaceuticals in enantiomerically or diastereoisomerically pure form, as racemic mixtures or mixtures enriched in one or more stereoisomer. The scope of the present invention as claimed describes the racemic forms of such compounds as well as the individual enantiomers, diastereomers, and stereoisomer-enriched mixtures.

A single stereoisomer of a chiral compound is commonly prepared from an optically pure precursor, or by separation of enantiomers by chromatography, for example chiral high pressure liquid chromatography (HPLC). Racemic mixtures may also be converted into separable diastereomers by reacting with a suitably reactive chiral compound for isolation by chromatography. Alternatively, separation may be achieved by converting into a chiral salt. For example, a racemic chiral compound containing a basic group may form a diastereomeric salt with a chiral acid such as malic acid. The mixture of diastereomeric salts so produced may then be separated by fractional crystallization. The pure synthetic diastereomers produced by these methods may then be converted to the desired stereoisomer by classical chemical means known to one skilled in the art. In the present invention, chiral racemic compounds may be separated by chiral HPLC on a suitable chiral stationary phase eluting with a mixture of heptane/ethanol or with a pure alcohol (methanol or ethanol). Stereoisomer conglomerates may be separated by conventional techniques known to those skilled in the art. See, e.g. "Stereochemistry of Organic Compounds" by Ernest L. Eliel (Wiley, New York, 1994).

The compounds of formula (I) may be used in the form of salts derived from pharmaceutically acceptable inorganic or organic acids. Unless otherwise indicated, "pharmaceutically acceptable salt" refers to a salt prepared by combining a compound of formula (I) with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid. Suitable pharmaceutically acceptable acid addition salts of the compounds of the present invention when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, β-hydroxybutyrate, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate. Furthermore, where the compounds of the invention carry an acidic moiety, suitable pharmaceutically acceptable salts thereof may include alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts. Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl (CrCe) halides (e.g., methyl, ethyl, propyl, and butyl chlorides, bromides, and iodides), dialkyl sulfates (i.e., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Hemisalts of acids and bases may also be formed, for example, hemisulfate and hemicalcium salts.

The language "compounds of formula (I)" include all subformulae and specific embodiments herein disclosed. Moreover, unless otherwise indicated, the language "compounds of formula (I)" include all forms of the compound of formula (I), including hydrates, solvates isomers, crystalline and non-crystalline forms, isomorphs, polymorphs, and metabolites thereof. For example, the compounds of formula (I), or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm. Stereoisomers of the compounds of formula (I) include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Unless otherwise indicated, the language "compounds of formula (I)" include the tautomeric forms of compounds. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. The various ratios of the tautomers in solid and liquid form is dependent on the various substituents on the molecule as well as the particular crystallization technique used to isolate a compound.

Pharmaceutical Composition, Medicament and Use

The invention also relates to a pharmaceutical composition comprising a compound as depicted above.

Accordingly the invention relates to pharmaceutical composition comprising at least one compound of the invention and an acceptable pharmaceutical excipient.

According to one embodiment, the invention relates to a pharmaceutical composition comprising a compound of formula (I) or a pharmaceutically acceptable salt thereof and art least one pharmaceutically acceptable carrier and/or excipient.

As is known to the person skilled in the art, various forms of excipients can be used adapted to the mode of administration and some of them can promote the effectiveness of the active molecule, e.g. by promoting a release profile rendering this active molecule overall more effective for the desired treatment.

The pharmaceutical compositions of the invention are thus able to be administered in various forms, for example as injectable, pulverizable or ingestible form, for example via intramuscular, intravenous, subcutaneous, intradermal, oral, topical, rectal, vaginal, ophthalmic, nasal, transdermal or parenteral route. The present invention notably covers the use of a compound according to the present invention for the manufacture of a composition, particularly a pharmaceutical composition.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The composition of the invention can also take the form of a pharmaceutical or cosmetic composition for topical administration.

Such compositions may be presented in the form of a gel, paste, ointment, cream, lotion, liquid suspension, aqueous-alcoholic or oily solutions, or dispersions of the lotion or serum type, or anhydrous or lipophilic gels, or emulsions of liquid or semi-solid consistency of the milk type, obtained by dispersing a fatty phase in an aqueous phase or vice versa, or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

The composition according to the invention may comprise any ingredient commonly used in dermatology and cosmetics. It may comprise at least one ingredient selected from hydrophilic or lipophilic gelling agents, hydrophilic or lipophilic active agents, preservatives, emollients, viscosity enhancing polymers, humectants, surfactants, preservatives, antioxidants, solvents, perfumes, fillers, screening agents, bactericides, odor absorbers and coloring matter.

As oils which can be used in the invention, mineral oils (liquid paraffin), vegetable oils (liquid fraction of shea butter, sunflower oil), animal oils, synthetic oils, silicone oils (cyclomethicone) and fluorinated oils may be mentioned. Fatty alcohols, fatty acids (stearic acid) and waxes (paraffin, carnauba, beeswax) may also be used as fatty substances.

Emulsifiers which can be used in the invention include, for example, glycerol stearate, polysorbate 60 and the PEG-6/PEG-32/glycol stearate mixture.

Hydrophilic gelling agents which can be used in the invention include, for example, carboxyvinyl polymers (carbomer), acrylic copolymers such as acrylate/alkylacrylate copolymers, polyacrylamides, polysaccharides such as hydroxypropylcellulose, clays and natural gums. Lipophilic gelling agents which can be used in the invention include, for example modified clays such as bentones, metal salts of fatty acids such as aluminum stearates and hydrophobic silica, or alternatively ethylcellulose and polyethylene.

As hydrophilic active agents, proteins or protein hydrolysates, amino acids, polyols, urea, allantoin, sugars and sugar derivatives, vitamins, starch and plant extracts, in particular those of Aloe Vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

In addition, a surfactant can be included in the composition so as to provide deeper penetration of the compound capable to show an anti-proliferative activity against a large panel of tumor cell lines as single agent or in combination with other cytotoxic agents.

Among the contemplated ingredients, the invention embraces penetration enhancing agents selected for example from the group consisting of mineral oil, water, ethanol, triacetin, glycerin and propylene glycol; cohesion agents selected for example from the group consisting of polyisobutylene, polyvinyl acetate and polyvinyl alcohol, and thickening agents.

Chemical methods of enhancing topical absorption of drugs are well known in the art. For example, compounds with penetration enhancing properties include sodium lauryl sulfate (Dugard, P. H. and Sheuplein, R. J., "Effects of Ionic Surfactants on the Permeability of Human Epidermis: An Electrometric Study," J. Ivest. Dermatol., V. 60, pp. 263-69, 1973), lauryl amine oxide (Johnson et. al., U.S. Pat. No. 4,411,893), azone (Rajadhyaksha, U.S. Pat. Nos. 4,405,616 and 3,989,816) and decylmethyl sulfoxide (Sekura, D. L. and Scala, J., "The Percutaneous Absorption of Alkylmethyl Sulfides," Pharmacology of the Skin, Advances In Biology of Skin, (Appleton-Century Craft) V. 12, pp. 257-69, 1972). It has been observed that increasing the polarity of the head group in amphoteric molecules increases their penetration-enhancing properties but at the expense of increasing their skin irritating properties (Cooper, E. R. and Berner, B., "Interaction of Surfactants with Epidermal Tissues: Physiochemical Aspects," Surfactant Science Series, V. 16, Rieger, M. M. ed. (Marcel Dekker, Inc.) pp. 195-210, 1987).

A second class of chemical enhancers is generally referred to as co-solvents. These materials are absorbed topically relatively easily, and, by a variety of mechanisms, achieve permeation enhancement for some drugs. Ethanol (Gale et al., U.S. Pat. No. 4,615,699 and Campbell et al., U.S. Pat. Nos. 4,460,372 and 4,379,454), dimethyl sulfoxide (U.S. Pat. Nos. 3,740,420 and 3,743,727, and 4,575,515), and glycerine derivatives (U.S. Pat. No. 4,322,433) are a few examples of compounds which have shown an ability to enhance the absorption of various compounds.

The pharmaceutical compositions of the invention can also be intended for administration with aerosolized formulation to target areas of a patient's respiratory tract.

Devices and methodologies for delivering aerosolized bursts of a formulation of a drug is disclosed in U.S. Pat. No. 5,906,202. Formulations are preferably solutions, e.g. aqueous solutions, ethanolic solutions, aqueous/ethanolic solutions, saline solutions, colloidal suspensions and microcrystalline suspensions. For example aerosolized particles comprise the active ingredient mentioned above and a carrier, (e.g., a pharmaceutically active respiratory drug and carrier) which are formed upon forcing the formulation through a nozzle which nozzle is preferably in the form of a flexible porous membrane. The particles have a size which is sufficiently small such that when the particles are formed they remain suspended in the air for a sufficient amount of time such that the patient can inhale the particles into the patient's lungs.

The invention encompasses the systems described in U.S. Pat. No. 5,556,611:
liquid gas systems (a liquefied gas is used as propellant gas e.g. low-boiling FCHC or propane, butane in a pressure container),
suspension aerosol (the active substance particles are suspended in solid form in the liquid propellant phase),
pressurized gas system (a compressed gas such as nitrogen, carbon dioxide, dinitrogen monoxide, or air is used).

Thus, according to the invention the pharmaceutical preparation is made in that the active substance is dissolved or dispersed in a suitable nontoxic medium and said solution or dispersion atomized to an aerosol, i.e. distributed extremely finely in a carrier gas. This is technically possible for example in the form of aerosol propellant gas packs, pump aerosols or other devices known per se for liquid misting and solid atomizing which in particular permit an exact individual dosage.

Therefore, the invention is also directed to aerosol devices comprising the compound as defined above and such a formulation, preferably with metered dose valves.

The pharmaceutical compositions of the invention can also be intended for intranasal administration.

In this regard, pharmaceutically acceptable carriers for administering the compound to the nasal mucosal surfaces will be readily appreciated by the ordinary artisan. These carriers are described in the Remington's Pharmaceutical Sciences" 16th edition, 1980, Ed. by Arthur Osol.

The selection of appropriate carriers depends upon the particular type of administration that is contemplated. For administration via the upper respiratory tract, the composition can be formulated into a solution, e.g., water or isotonic saline, buffered or unbuffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2 (Remington's, Id. at page 1445). Of course, the ordinary artisan can readily determine a suitable saline content and pH for an innocuous aqueous carrier for nasal and/or upper respiratory administration.

Common intranasal carriers include nasal gels, creams, pastes or ointments with a viscosity of, e.g., from about 10 to about 3000 cps, or from about 2500 to 6500 cps, or greater, may also be used to provide a more sustained contact with the nasal mucosal surfaces. Such carrier viscous formulations may be based upon, simply by way of example, alkylcelluloses and/or other biocompatible carriers of high viscosity well known to the art (see e.g., Remington's, cited supra). A preferred alkylcellulose is, e.g., methylcellulose in a concentration ranging from about 5 to about 1000 or more mg per 100 ml of carrier. A more preferred concentration of methyl cellulose is, simply by way of example, from about 25 to about 150 mg per 100 ml of carrier.

Other ingredients, such as known preservatives, colorants, lubricating or viscous mineral or vegetable oils, perfumes, natural or synthetic plant extracts such as aromatic oils, and humectants and viscosity enhancers such as, e.g., glycerol, can also be included to provide additional viscosity, moisture retention and a pleasant texture and odor for the formulation. For nasal administration of solutions or suspensions according to the invention, various devices are available in the art for the generation of drops, droplets and sprays.

A premeasured unit dosage dispenser including a dropper or spray device containing a solution or suspension for delivery as drops or as a spray is prepared containing one or more doses of the drug to be administered and is another object of the invention. The invention also includes a kit containing one or more unit dehydrated doses of the compound, together with any required salts and/or buffer agents, preservatives, colorants and the like, ready for preparation of a solution or suspension by the addition of a suitable amount of water.

Another aspect of the invention is directed to the use of said compound to manufacture a medicament. Especially, the invention relates to a medicament comprising a compound according to the invention or a pharmaceutically acceptable salt thereof. In other words, the invention embraces a method for treating a disease by inhibiting the proliferation of tumor cells comprising administering an effective amount of at least one compound as defined above to a subject in need of such treatment.

Advantageously, the compounds according to the invention can be used in an efficient amount. These quantities are generally comprised between 0.1 mg and 2 g of the compound of the invention per day per kilogram of body weight.

In another aspect, the present invention is directed to a method for modulating, regulating, and/or inhibiting cells proliferation. Said method comprises administering to cells at least one compound of formula (I) as defined above, such as a compound of formula (II) or (III), or a pharmaceutically acceptable salt thereof.

The methods presently disclosed may be for treating a hematological and/or a proliferative disease or disorder in a subject. In a specific embodiment, the disease or disorder is a proliferative disease or disorder. In a specific embodiment, the disease or disorder is a hematological disease or disorder. In a specific embodiment, the disease or disorder is a proliferative hematological disease or disorder. In a specific embodiment, the disease is cancer.

In one embodiment, said subject has been diagnosed as having a proliferative disease or disorder. In one embodiment, said subject has been diagnosed as having a hematological disease or disorder.

In one embodiment, the methods presently disclosed do not induce nor lead to inhibition of protein kinases.

Diseases and disorders known to be associated with these hematological and proliferative diseases include for example:
- hematological disorders such as lymphomas and leukemias including Non-Hodgkin Lymphoma, Diffuse large B-cell lymphoma (DLBCL) Follicular lymphoma (FL), Mantle cell lymphoma (MCL), B-cell chronic lymphocytic leukemia (B-CLL)/small lymphocytic lymphoma (SLL), Waldenstrom's macroglbulinemia (WM), Marginal zone lymphoma (MZL), Burkitt lymphoma and peripheral T-cell lymphomas (PTCL); as well as multiple myeloma (MM), myelodysplatic syndrome (MDS), myelodysplasia with myelofibrosis;
- proliferative diseases such as mastocytosis including urticaria pigmentosa (UP), telangiectasia macularis eruptiva perstans (TMEP), indolent systemic mastocytosis, aggressive systemic mastocytosis and Leukemic systemic mastocytosis;
- proliferative diseases such as solid tumours including head and neck cancer, melanoma, kidney carcinoma, stomach carcinoma, liver carcinoma, colorectal carcinoma, pancreas carcinoma, lung carcinoma, neuronal carcinoma, glioblastoma multiforme, bone carcinoma, osteosarcoma, Ewing sarcoma, breast carcinoma, ovary carcinoma, prostate carcinoma.

A compound of formula (I), such as a compound of formula (II) or (III), or a pharmaceutically acceptable salt thereof may be used for treating a disease or disorder as disclosed above such as hematological disorders and/or proliferative disorders. Proliferative disorder may be cancer.

In one embodiment, a compound of formula (I), such as a compound of formula (II) or (III), or a pharmaceutically acceptable salt thereof is for use in the treatment of a disease or disorder as disclosed above such as hematological and/or proliferative diseases or disorders. In a specific embodiment, the disease or disorder is a proliferative disease or disorder. In a specific embodiment, the disease or disorder is a hematological disease or disorder. In a specific embodiment, the disease or disorder is a proliferative hematological disease or disorder. In a specific embodiment, the disease is cancer.

In a specific embodiment, compounds of formula (I) are for use in modulating, regulating, and/or inhibiting hematopoietic tumor cell lines proliferation. In a specific embodiment, compounds of formula (I) are for use in modulating, regulating, and/or inhibiting solid tumor cell lines proliferation.

In the methods presently disclosed, the compound of formula (I) or a pharmaceutically acceptable salt thereof, may be used as sole active pharmaceutical ingredient or in combination with another active pharmaceutical ingredient. In one embodiment, the compound of formula (I) or a pharmaceutically acceptable salt thereof, is used as sole active pharmaceutical ingredient. In one embodiment, the compound of formula (I) or a pharmaceutically acceptable salt thereof, is used in combination with another active pharmaceutical ingredient.

The present invention relates to a method for preventing or treating a disease or disorder selected form hematological disorders and proliferative disorders, that method comprising simultaneously or sequentially administering to a human or animal subject in need thereof at least one compound of formula (I) or a pharmaceutically acceptable salt thereof in combination with another active pharmaceutical ingredient, in sufficient amounts to provide a therapeutic effect.

The present invention is directed to a pharmaceutical composition comprising a compound of formula (I) such as a compound of formula (II) or (III), or a pharmaceutically acceptable salt thereof, and another active pharmaceutical agent as a combined preparation for sequential, simultaneous or separate use in the treatment of a disease or disorder selected from the group consisting of hematological disorders and proliferative disorders.

The present invention is directed to the use of a compound of formula (I) such as a compound of formula (II) or (III), or a pharmaceutically acceptable salt thereof optionally in combination with another pharmaceutically active agent, for the manufacture of a medicament for the treatment of a disease or disorder selected from the group consisting of a hematological disorder and a proliferative disorder.

Although methods and uses disclosed above refer to a compound of formula (I), such as a compound of formula (II) or (III), or a pharmaceutically acceptable salt thereof, whenever technically compatible, they are to be understood to equally refer to pharmaceutical compositions including the same compounds.

General Synthetic Procedures

Compounds of the invention can be prepared by several methods including methods outlined in Schemes 1-2, wherein the substituents are as defined in formula (I), above, except where further noted. The synthetic methods described below are merely exemplary, and the compounds of the invention may be synthesized by alternate routes as appreciated by persons of ordinary skill in the art.

Accordingly, the synthesis of the aminooxazole derivatives V were undergone by firstly reacting aromatic aldehydes I with p-toluenesulfonylmethyl isocyanide (TosMIC) to prepare the corresponding oxazole derivatives II using the method of Van Leusen et al. (*Tetrahedron Lett.*, 1972, 23, 2369) (Scheme 1). The non-commercial aldehydes were prepared using literature methods to introduce the aldehyde group either from the corresponding brominated aromatic compound using an organometallic reagent and DMF or from the oxidation of corresponding toluene according the method of Frey et al. (*Tetrahedron Lett.*, 2001, 39, 6815) or from the reaction employing the dibromination of bromopicolines followed by hydrolysis using an aqueous solution of calcium carbonate used in the method of Bombrun et al. (*Tetrahedron Lett.*, 2005, 36, 6033). Secondly, those compounds II were then further functionalised by deprotonation of the oxazole moiety by a suitable organic base and subsequent electrophilic chlorination was used to prepare the 2-chlorooxazole compounds III. A direct nucleophilic displacement reaction by aniline compounds IV (wherein R' is hydrogen), in the presence of a suitable solvent such as alcohol and with heating in elevated temperature, should generally afford the final target compounds V. Compounds V can also obtained by reacting compounds IV (wherein R' is an acetyl group) and compounds III in the presence of sodium hydride and in a suitable solvent such as tetrahydrofurane or dimethylformamide (WO/2007/131953).

The synthesis of the aminothiazole derivatives VIII were undergone firstly by reacting aromatic aldehydes I with (methoxymethyl)triphenyl phosphonium chloride to prepare the corresponding enole ether derivatives VI using Wittig reaction described by Iwao et al. (*J. Org. Chem.* 2009, 74, 8143). Secondly, a cyclisation was performed with the enole ether VI, thiourea derivatives VII and N-bromosuccinimide (NBS) using the method of Zhao et al. (*Tetrahedron Lett.*, 2001, 42, 2101). The thiourea derivatives VII was synthesised by reacting aniline IX and ammonium thiocyanate.

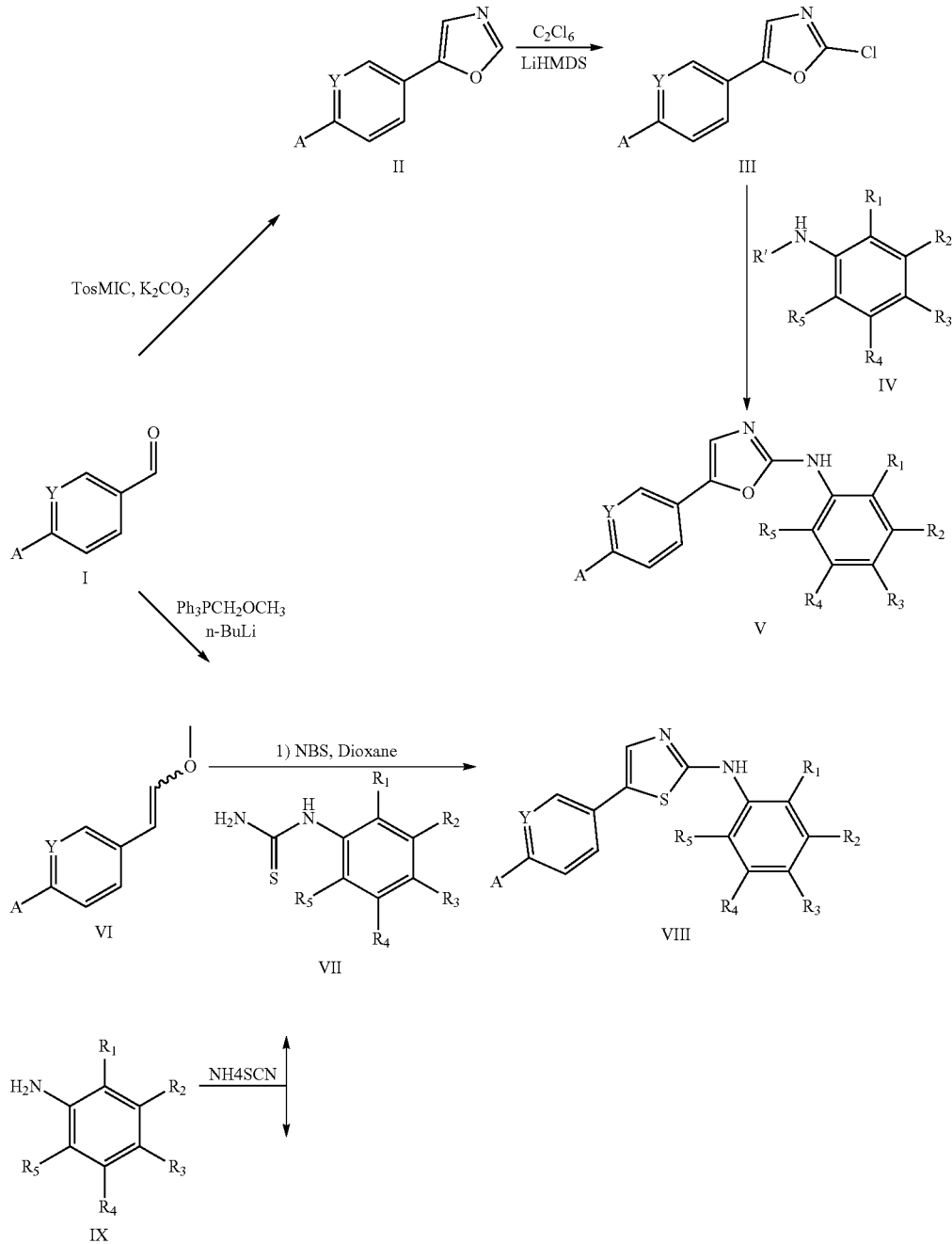

Scheme 1

The synthesis of the aminothiazole derivatives XI were undergone using Hantzsch reaction by a cyclisation with the 2-bromoketone X and thiourea derivatives VII under basic conditions in the presence of a suitable solvent such as alcohol and with heating in elevated temperature.

Compounds of formula (I) may alternatively be prepared through copper or palladium coupling reaction according to scheme 2 below, by reacting compound XII and optionally substituted heterocycle A-L, where Y can be I, Br or Cl and L is hydrogen, boronic acid, boronic ester or trialkyl stanyl. Person of ordinary skill in the art is able to recognize that compounds XII may alternatively be prepared according to the protocol outlined in scheme 1 above.

Scheme 2

EXAMPLES

The invention is now illustrated by Examples which represent currently preferred embodiments which make up a part of the invention but which in no way are to be used to limit the scope of it.

A. Compound Synthesis

The invention will be more fully understood by reference to the following preparative examples, but they should not be construed as limiting the scope of the invention. General: All chemicals used were commercial reagent grade products. Solvents were of anhydrous commercial grade and were used without further purification. The progress of the reactions was monitored by thin layer chromatography using precoated silica gel 60F 254, Merck TLC plates, which were visualized under UV light. Multiplicities in $^1$H NMR spectra are indicated as singlet (s), broad singlet (br s), doublet (d), triplet (t), quadruplet (q), and multiplet (m) and the NMR spectrum were performed either on a Bruker 300 or 500 MHz spectrometer.

Abbreviations n-Buli n-Buthyl lithium
t-BuOH Tert-Butyl alcohol
$CaCO_3$ Calcium carbonate
$CCl_4$ Carbone tetrachloride
$C_2Cl_6$ Hexachloroethane
$CDCl_3$ Deuterochloroform
$Cs_2CO_3$ Cesium carbonate
CuI Cupper Iodide
DCC Dicyclohexylcarbodiimide
DCM Dichloromethane
DMAP 4-Dimethylaminopyridine
DMF Dimethylformamide
DMSO-$d_6$ Hexadeuterodimethyl sulfoxide
EDCI 1-Ethyl-3-(3-dimethylaminopropyl)carbodiimide
EtOAc Ethyl acetate
EtOH Ethanol
$Et_2O$ Diethyl ether
$Et_3N$ Triethylamine
h Hour(s)
$H_2O$ Water
$H_4N_2$ Hydrazine monohydrate
HCl Hydrochloric acid
Conc. HCl Concentrated hydrochloric acid (37%)
HOBt Hydroxybenzotriazole
iPrOH 2-Propanol
$K_2CO_3$ Potassium carbonate
$KHCO_3$ Potassium hydrogen carbonate
LiHMDS Lithium bis(trimethylsilyl)amide
MeOH Methanol
$MgSO_4$ Magnesium sulfate
Mins Minutes
NaCl Sodium chloride
NaH Sodium hydride
$NaHCO_3$ Sodium hydrogen carbonate
$NaNO_2$ Sodium nitrite NaOEt Sodium ethoxide
NaOH Sodium hydroxide
NBS N-bromo-succinimide
NH$_4$Cl Ammonium chloride
NH$_4$SCN Ammonium thiocyanate
Pd/C Palladium on carbon 10 wt. %
Pd$_2$(dba)$_3$ Tris(dibenzylidenacetone)dipalladium(0)
PE Petroleum ether
(PhCO)$_2$O$_2$ Benzoyl peroxide
SnCl$_2$.2H$_2$O Tin(II)chloride dihydrate
RT Room temperature
TFA Trifluoroacetic acid
THF Tetrahydrofuran
TosMIC p-Toluenesulfonylmethyl isocyanide
Xantphos 4,5-Bis(diphenylphosphino)-9,9-dimethylxanthene A.1. Compound 001

Synthetic Approach of Compound 001

Preparation of 2-bromo-5-(dibromomethyl)pyridine
(Ia)

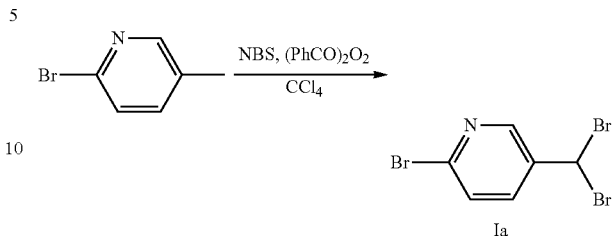

To a solution of 2-Bromo-5-methyl-pyridine (3.000 g, 17.44 mmol) in CCl$_4$ (30 ml) were added N-bromosuccinimide (6.829 g, 38.36 mmol) and benzoylperoxide (506 mg, 2.09 mmol). The reaction mixture was stirred at 90° C. for 16 hours under darkness conditions. The reaction mixture was cooled down and PE was added. The resulting solid was

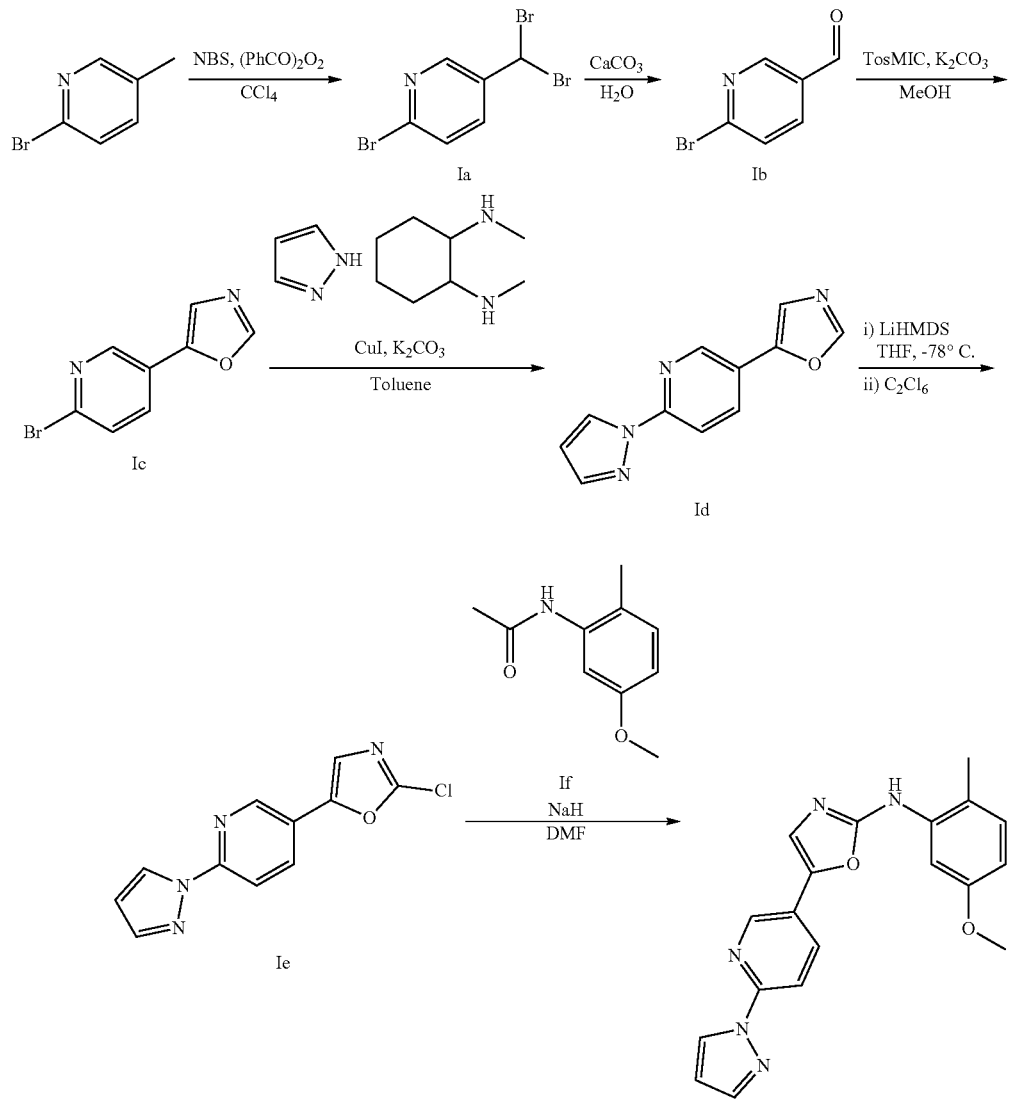

filtered off and washed with more PE. The cooled mixture was evaporated to dryness, diluted with water and extracted with EtOAc. The combined organics were dried over MgSO₄, filtered and evaporated. The final product was purified by silica gel chromatography using 10% EtOAc/cyclohexane as eluent to give intermediate Ia (4.6 g, 80%). ¹H NMR (500 MHz, CDCl₃) δ 8.46 (d, J=2.6 Hz, 1H), 7.87 (dd, J=8.4, 2.7 Hz, 1H), 7.55 (d, J=8.4 Hz, 1H), 6.61 (s, 1H).

Preparation of 6-bromonicotinaldehyde (Ib)

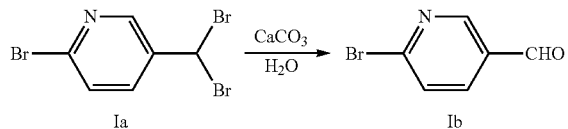

A solution of intermediate Ia (3.650 g, 11.07 mmol), calcium carbonate (2.437 g, 24.35 mmol) in water (80 ml) was stirred at 105° C. for 16 hours. The cooled mixture was diluted with water and extracted with EtOAc twice. The combined organics were washed with water, with saturated solution of NaCl, dried over MgSO₄, filtered and evaporated to give intermediate Ib (1.890 g, 92%). ¹H NMR (500 MHz, CDCl₃) δ 10.05 (s, 1H), 8.78 (d, J=2.2 Hz, 1H), 7.98 (dd, J=8.2, 2.4 Hz, 1H), 7.65 (d, J=8.2 Hz, 1H).

Preparation of 5-(6-bromopyridin-3-yl)oxazole (Ic)

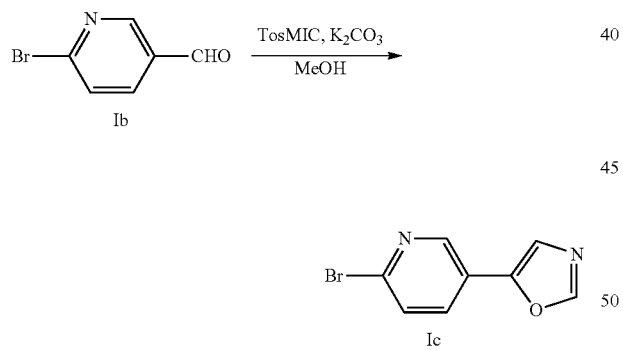

To a solution of intermediate Ib (1.600 g, 8.60 mmol) in MeOH (35 ml) were added K₂CO₃ (3.567 g, 25.80 mmol) and TosMIC (2.015 g, 10.32 mmol). The reaction mixture was stirred at room temperature for 16 hours. The cooled mixture was evaporated to dryness, diluted with water and extracted with EtOAc twice. The combined organics were washed with water, with saturated solution of NaCl, dried over MgSO₄, filtered and evaporated. The final product was purified by silica gel chromatography using 30% EtOAc/cyclohexane as eluent to give intermediate Ic (1.371 g, 71%). ¹H NMR (500 MHz, CDCl₃) δ 8.68 (d, J=2.4 Hz, 1H), 7.98 (s, 1H), 7.78 (dd, J=8.3, 2.5 Hz, 1H), 7.56 (d, J=8.3 Hz, 1H), 7.46 (s, 1H).

Preparation of 5-(6-(1H-pyrazol-1-yl)pyridin-3-yl)oxazole (Id)

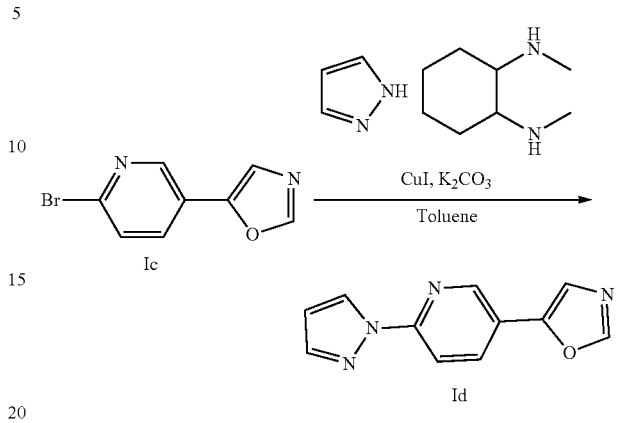

In a sealed tube, to a solution of intermediate Ic (1.000 g, 4.44 mmol) in dry toluene (6 mL) were added successively pyrazole (454 mg, 6.66 mmol), potassium carbonate (1.228 g, 8.88 mmol), rac-trans-N,N'-dimethylcyclohexane-1,2-diamine (137 µL, 0.89 mmol) and copper iodide (42 mg, 0.22 mmol). The reaction mixture was stirred at 110° C. for 3 days. The cooled mixture was diluted with water and extracted with EtOAc twice. The combined organics were washed with water, with saturated solution of NaCl, dried over MgSO₄, filtered and evaporated. The final product was purified by silica gel chromatography using 0 to 30% EtOAc/cyclohexane as eluent to give intermediate Id (817 mg, 87%). ¹H NMR (300 MHz, DMSO-d₆) δ 8.85 (d, J=2.3 Hz, 1H), 8.65 (dd, J=2.6, 0.5 Hz, 1H), 8.55 (s, 1H), 8.31 (dd, J=8.6, 2.3 Hz, 1H), 8.02 (dd, J=8.6, 0.7 Hz, 1H), 7.87 (d, J=1.6 Hz, 1H), 7.84 (s, 1H), 6.61 (dd, J=2.6, 1.7 Hz, 1H).

Preparation of 5-(6-(1H-pyrazol-1-yl)pyridin-3-yl)-2-chlorooxazole (Ie)

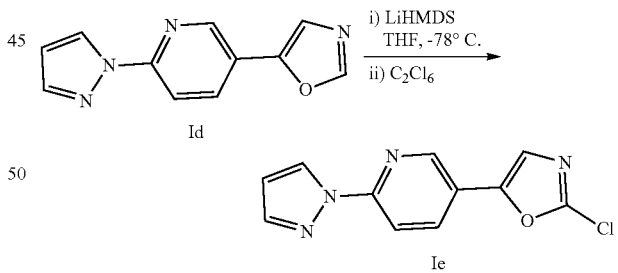

To a stirred solution of intermediate Id (817 mg, 3.85 mmol) in dry THF (26 ml) was added a solution of LiHMDS in dry THF (4.23 ml, 4.23 mmol) dropwise at −78° C. over 10 mins. The reaction mixture was stirred at −78° C. for 30 mins. Then, C₂Cl₆ (1.094 g, 4.62 mmol) was added and the reaction mixture was stirred at room temperature for 16 hours. The mixture was diluted with water and extracted with EtOAc twice. The combined organics were washed with water, with saturated solution of NaCl, dried over MgSO₄, filtered and evaporated. The final product was purified by silica gel chromatography using 0 to 30% EtOAc/cyclohexane as eluent to give intermediate Ie (736 mg, 78%). $^1$H NMR (300 MHz, DMSO-d$_6$) δ 8.81 (d, J=2.2 Hz, 1H), 8.65 (d, J=2.6 Hz, 1H), 8.27 (dd, J=8.6, 2.3 Hz, 1H), 8.02 (d, J=8.7 Hz, 1H), 7.92 (s, 1H), 7.87 (d, J=0.8 Hz, 1H), 6.72-6.55 (m, 1H).

Preparation of
N-(5-methoxy-2-methylphenyl)acetamide (If)

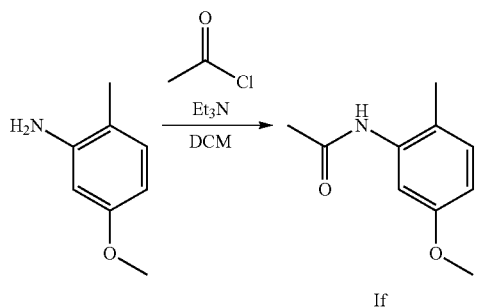

To a solution of 5-Methoxy-2-methyl-phenylamine (4.000 g, 29.16 mmol) in dry DCM (60 ml) were added successively dry Et$_3$N (12.2 ml, 87.48 mmol) and acetyl chloride (4.2 ml, 58.32 mmol) dropwise at 0° C. The reaction mixture was stirred at room temperature for 2 hours. The mixture was diluted with water and extracted with DCM twice. The combined organics were washed with water, with saturated solution of NaCl, dried over MgSO$_4$, filtered and evaporated. The final product was purified by silica gel chromatography using 40 to 60% EtOAc/cyclohexane as eluent to give intermediate If (4.952 g, 95%). $^1$H NMR (300 MHz, CDCl$_3$) δ 7.49 (d, J=2.2 Hz, 1H), 7.05 (d, J=8.4 Hz, 2H), 6.63 (dd, J=8.3, 2.3 Hz, 1H), 3.77 (s, 3H), 2.18 (s, 3H), 2.17 (s, 3H).

Preparation of 5-(6-(1H-pyrazol-1-yl)pyridin-3-yl)-N-(5-methoxy-2-methylphenyl)oxazol-2-amine
(001)

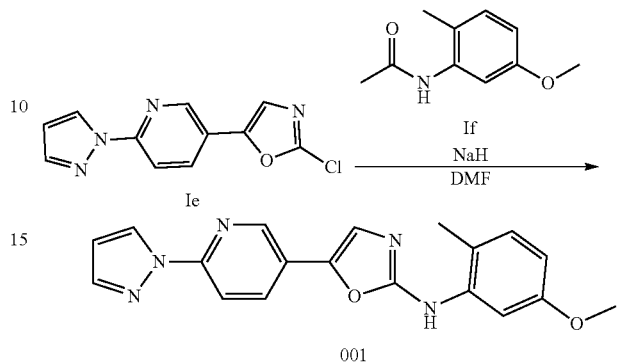

To a solution of sodium hydride 60% dispersion in mineral oil (162 mg, 4.06 mmol) in dry DMF (5 ml) was added a solution of intermediate If (363 mg, 2.03 mmol) in dry DMF (5 ml) dropwise at 0° C. The reaction mixture was stirred at room temperature for 1 hour and a solution of intermediate Ie (500 mg, 2.03 mmol) in dry DMF (5 ml) was added dropwise at 0° C. The reaction mixture was stirred for 3 hours at 0° C. The mixture was diluted with water and extracted with EtOAc twice. The combined organics were washed with a saturated solution of NaHCO$_3$ (3 times), with water, with saturated solution of NaCl, dried over MgSO$_4$, filtered and evaporated. The final product was purified by silica gel chromatography using 10 to 30% EtOAc/cyclohexane as eluent to give 001 (480 mg, 68%). $^1$H NMR (300 MHz, DMSO-d$_6$) δ 9.38 (s, 1H), 8.68 (d, J=2.1 Hz, 1H), 8.62 (d, J=2.4 Hz, 1H), 8.12 (dd, J=8.6, 2.3 Hz, 1H), 7.99 (d, J=8.6 Hz, 1H), 7.84 (s, 1H), 7.59 (s, 2H), 7.09 (d, J=8.3 Hz, 1H), 6.66-6.51 (m, 2H), 3.73 (s, 3H), 2.23 (s, 3H).

A.2. Compound 002

Synthetic Approach of Compound 002

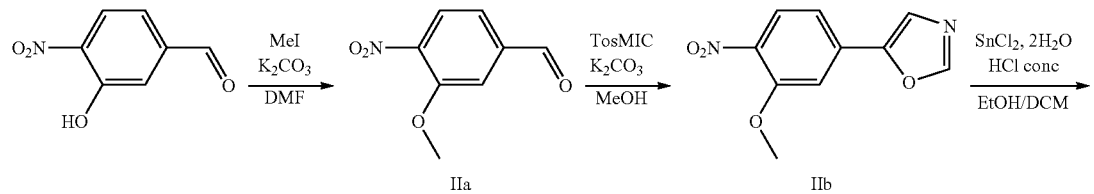

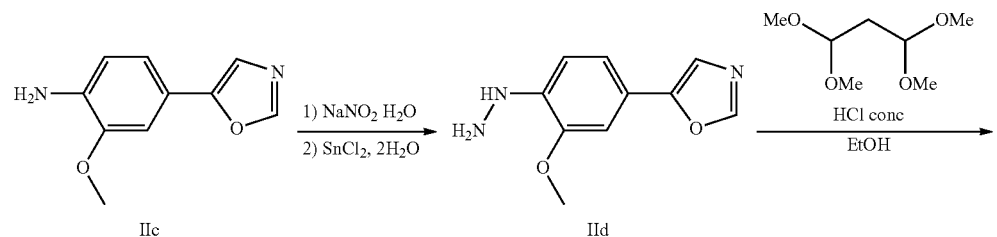

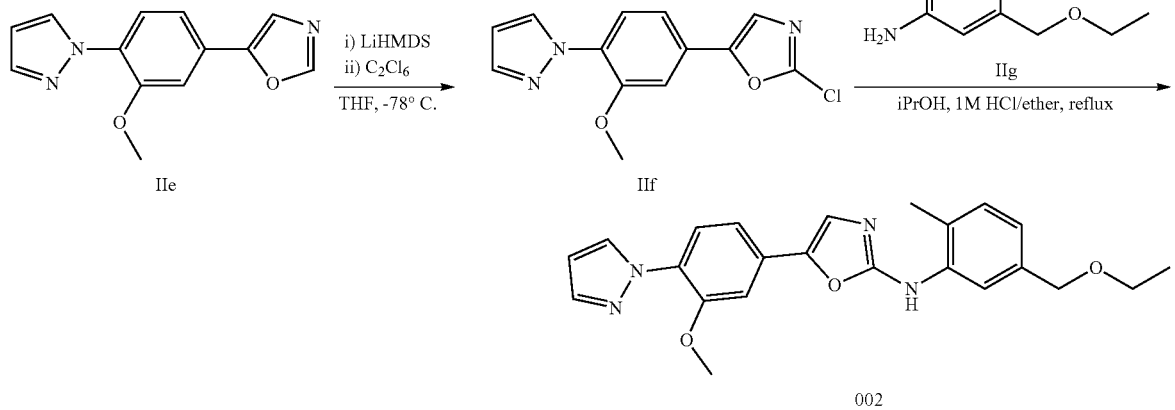

Preparation of 3-methoxy-4-nitrobenzaldehyde (IIa)

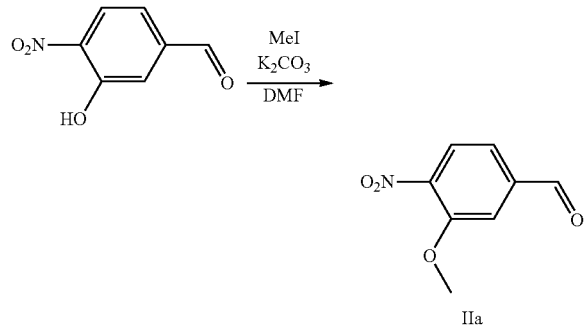

To a solution of 3-hydroxy-4-nitrobenzaldehyde (2.000 g, 11.98 mmol) in DMF (24 ml) were added K$_2$CO$_3$ (1.687 g, 12.22 mmol) and iodomethane (1.52 ml, 24.44 mmol). The reaction mixture was stirred at room temperature for 4 hours. The mixture was diluted with water and extracted with EtOAc twice. The combined organics were washed with a saturated solution of NaHCO$_3$ (3 times), with water, with saturated solution of NaCl, dried over MgSO$_4$, filtered and evaporated to give intermediate IIa (2.137 g, 98%). $^1$H NMR (500 MHz, CDCl$_3$) δ 10.06 (s, 1H), 7.93 (d, J=8.1 Hz, 1H), 7.60 (s, 1H), 7.54 (dd, J=8.1, 1.4 Hz, 1H), 4.04 (s, 3H).

Preparation of 5-(3-methoxy-4-nitrophenyl)oxazole (IIb)

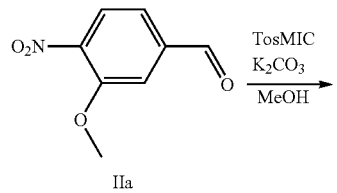

Prepared as for intermediate Ic above from intermediate IIa to give intermediate IIb (2.708 g, 100%). $^1$H NMR (500 MHz, CDCl$_3$) δ 8.00 (s, 1H), 7.95 (d, J=8.4 Hz, 1H), 7.52 (s, 1H), 7.35 (d, J=1.5 Hz, 1H), 7.31 (dd, J=8.4, 1.7 Hz, 1H), 4.05 (s, 3H).

Preparation of 2-methoxy-4-(oxazol-5-yl)aniline (IIc)

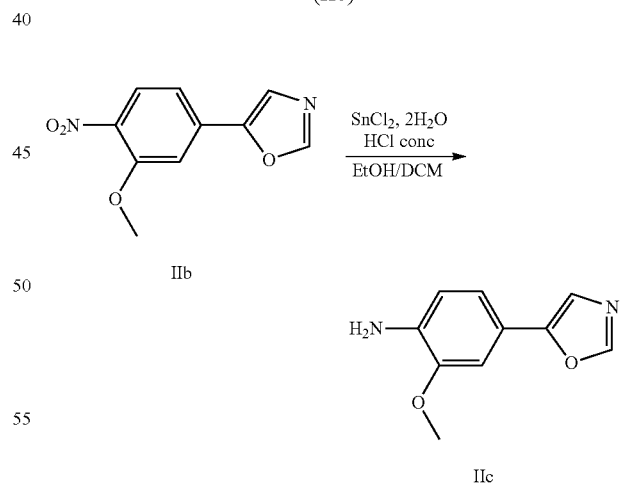

To a solution of intermediate IIb (2.708 g, 12.30 mmol) in EtOH/DCM (104/46 ml), were added SnCl$_2$.2H$_2$O (13.875 g, 61.50 mmol) and conc. HCl (10 ml). The reaction mixture was stirred at room temperature for 16 hours. Water was added and an aqueous solution of NaOH (2.5 M) was added until to get a basic pH. The crude product was extracted with DCM twice. The combined organics were washed with water, with saturated solution of NaCl, dried over MgSO$_4$, filtered and evaporated. The final product was purified by silica gel chromatography using 0 to 40% EtOAc/cyclohexane as eluent to give intermediate IIc (1.972 g, 84%). ¹H NMR (500 MHz, DMSO-d₆) δ 8.26 (s, 1H), 7.37 (s, 1H), 7.10 (d, J=1.8 Hz, 1H), 7.06 (dd, J=8.0, 1.8 Hz, 1H), 6.68 (d, J=8.1 Hz, 1H), 5.07 (s, 2H), 3.83 (s, 3H).

Preparation of 5-(4-hydrazinyl-3-methoxyphenyl)oxazole (IId)

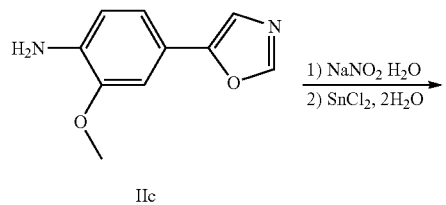

To a suspension of intermediate IIc (1.972 g, 10.37 mmol) in HCl 6N (25 ml) was added a solution of NaNO₂ (787 mg, 11.47 mmol) in H₂O (10 ml) dropwise at 0° C. The reaction mixture was stirred at 0° C. for 15 mins. Then, SnCl₂.2H₂O (6.784 g, 30.07 mmol) was added and the reaction mixture was stirred at 0° C. for 2 hours. A solution of NaOH 2.5N was added until to get basic pH and the crude product was extracted with EtOAc twice.

The combined organics were washed with water, with saturated solution of NaCl, dried over MgSO₄, filtered and evaporated to give intermediate IId (1.834 g, 86%). ¹H NMR (500 MHz, DMSO-d₆) δ 8.27 (s, 1H), 7.41 (s, 1H), 7.20 (dd, J=8.2, 1.7 Hz, 1H), 7.10 (d, J=1.7 Hz, 1H), 7.05 (d, J=8.2 Hz, 1H), 6.29 (s, 1H), 4.05 (s, 2H), 3.31 (s, 3H).

Preparation of 5-(3-methoxy-4-(1H-pyrazol-1-yl)phenyl)oxazole (IIe)

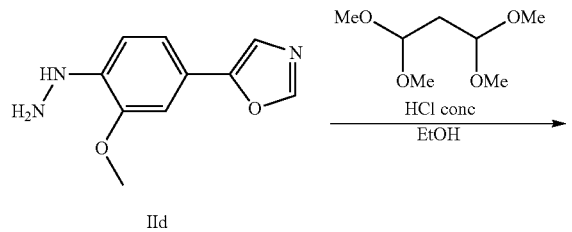

To a suspension of intermediate IId (1.834 g, 8.94 mmol) in EtOH (30 ml) were added malonaldehyde bis(dimethyl acetal) (1.63 ml, 9.84 mmol) and conc.HCl (1 ml). The reaction mixture was stirred at 70° C. for 2 hours. The cooled mixture was evaporated to dryness, diluted saturated solution of NaHCO₃ and extracted with EtOAc twice. The combined organics were washed with water, with saturated solution of NaCl, dried over MgSO₄, filtered and evaporated. The final product was purified by silica gel chromatography using 0 to 30% EtOAc/cyclohexane as eluent to give intermediate IIe (1.380 g, 64%). ¹H NMR (500 MHz, CDCl₃) δ 8.12 (d, J=2.1 Hz, 1H), 7.94 (s, 1H), 7.85 (d, J=8.3 Hz, 1H), 7.72 (d, J=1.4 Hz, 1H), 7.40 (s, 1H), 7.36 (dd, J=8.3, 1.8 Hz, 1H), 7.32 (d, J=1.7 Hz, 1H), 6.46-6.43 (m, 1H), 3.97 (s, 3H).

Preparation of 2-chloro-5-(3-methoxy-4-(1H-pyrazol-1-yl)phenyl)oxazole (IIf)

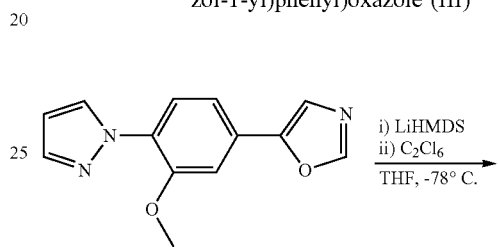

Prepared as for intermediate IIe above from intermediate IIe followed by silica gel chromatography using 0 to 20% EtOAc/cyclohexane as eluent to give intermediate IIf (1.380 g, 88%). ¹H NMR (500 MHz, CDCl₃) δ 8.13 (d, J=2.5 Hz, 1H), 7.86 (d, J=8.3 Hz, 1H), 7.72 (d, J=1.6 Hz, 1H), 7.33 (s, 1H), 7.30 (dd, J=8.3, 1.8 Hz, 1H), 7.24 (d, J=1.7 Hz, 1H), 6.48-6.42 (m, 1H), 3.98 (s, 3H).

Preparation of N-(5-(ethoxymethyl)-2-methylphenyl)-5-(3-methoxy-4-(1H-pyrazol-1-yl)phenyl)oxazol-2-amine (002)

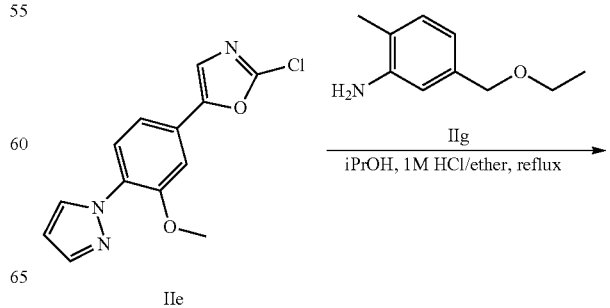

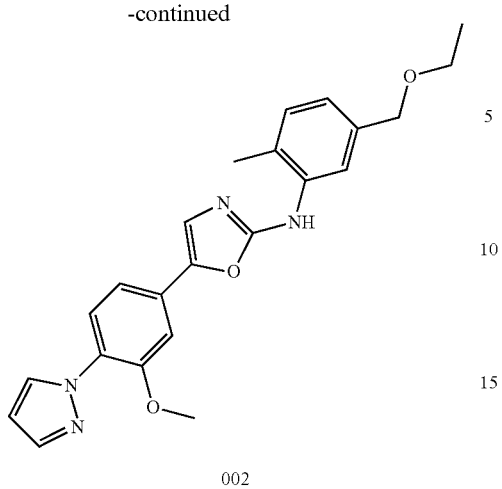

002

To a solution intermediate IIe (300 mg, 1.09 mmol) in dry iPrOH (2 ml) were added intermediate IIg (171 mg, 1.04 mmol) and solution of HCl in ether (220 μl, 0.22 mmol). The reaction mixture was stirred at 90° C. for 16 hours. The cooled mixture was evaporated to dryness, diluted with water and extracted with EtOAc twice. The combined organics were dried over MgSO$_4$, filtered and evaporated. The final product was purified by silica gel chromatography using 0 to 40% EtOAc/cyclohexane as eluent to give intermediate 002 (230 mg, 55%). $^1$H NMR (500 MHz, DMSO-d$_6$) δ 9.33 (s, 1H), 8.20 (d, J=2.3 Hz, 1H), 7.85 (s, 1H), 7.74-7.66 (m, 2H), 7.55 (s, 1H), 7.39 (d, J=1.6 Hz, 1H), 7.29 (dd, J=8.3, 1.7 Hz, 1H), 7.18 (d, J=7.7 Hz, 1H), 6.95 (dd, J=7.6, 1.2 Hz, 1H), 6.52-6.45 (m, 1H), 4.43 (s, 2H), 3.95 (s, 3H), 3.49 (q, J=7.0 Hz, 2H), 2.30 (s, 3H), 1.16 (t, J=7.0 Hz, 3H).

Synthetic Approach of (IIg)

Preparation of 4-ethoxymethyl-1-methyl-2-nitro-benzene (IIh)

To a solution of sodium ethoxide (75 mL, 246.42 mmol) in dry ethanol was added 4-chloromethyl-1-methyl-2-nitro-benzene (15.000 g, 82.14 mmol). The reaction mixture was stirred at room temperature for 16 hours. Water was added and ethanol was removed under reduced pressure. The crude product was extracted with DCM twice. The combined organics were washed with water, with saturated solution of NaCl, dried over MgSO$_4$, filtered and evaporated. The final product was purified by silica gel chromatography using 0 to 30% EtOAc/cyclohexane as eluent to give intermediate IIh (15.364 g, 96%). $^1$H NMR (300 MHz, CDCl$_3$) δ 7.95 (d, J=1.0 Hz, 1H), 7.48 (dd, J=7.8, 1.5 Hz, 1H), 7.31 (d, J=7.9 Hz, 1H), 4.52 (s, 2H), 3.56 (q, J=7.0 Hz, 2H), 2.58 (s, 3H), 1.26 (t, J=7.0 Hz, 3H).

Preparation of 5-ethoxymethyl-2-methyl-phenylamine (IIg)

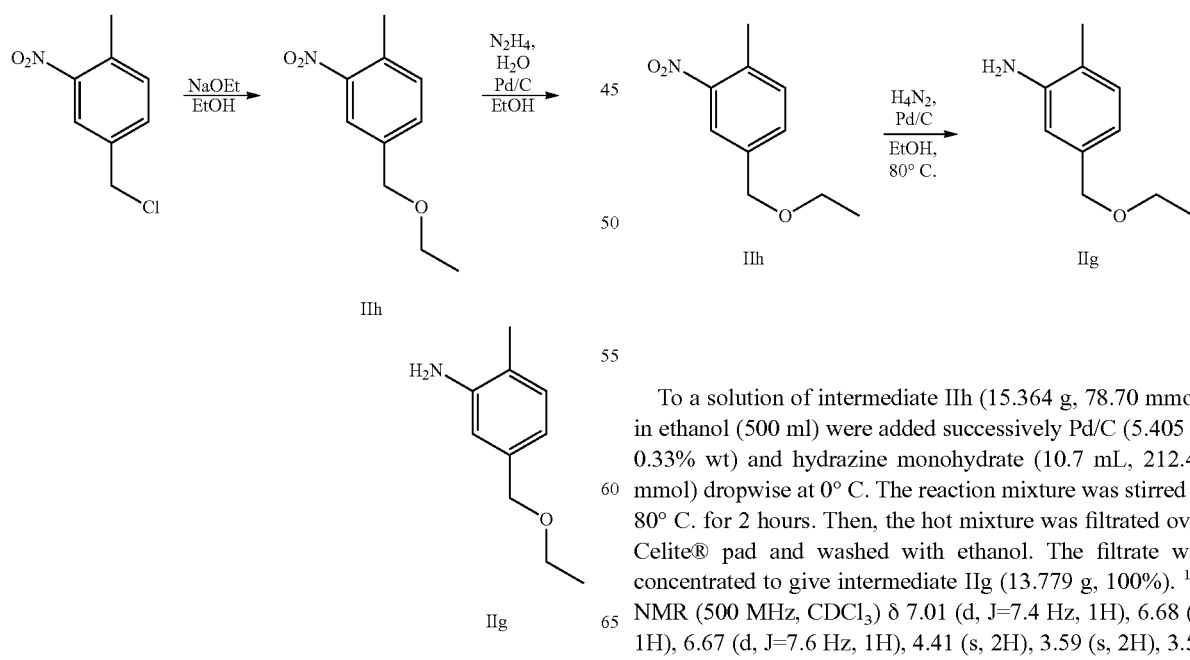

To a solution of intermediate IIh (15.364 g, 78.70 mmol) in ethanol (500 ml) were added successively Pd/C (5.405 g, 0.33% wt) and hydrazine monohydrate (10.7 mL, 212.49 mmol) dropwise at 0° C. The reaction mixture was stirred at 80° C. for 2 hours. Then, the hot mixture was filtrated over Celite® pad and washed with ethanol. The filtrate was concentrated to give intermediate IIg (13.779 g, 100%). $^1$H NMR (500 MHz, CDCl$_3$) δ 7.01 (d, J=7.4 Hz, 1H), 6.68 (s, 1H), 6.67 (d, J=7.6 Hz, 1H), 4.41 (s, 2H), 3.59 (s, 2H), 3.51 (q, J=7.0 Hz, 2H), 2.15 (s, 3H), 1.23 (t, J=7.0 Hz, 3H).

A.3. Compound 003

Synthetic Approach of Compound 003

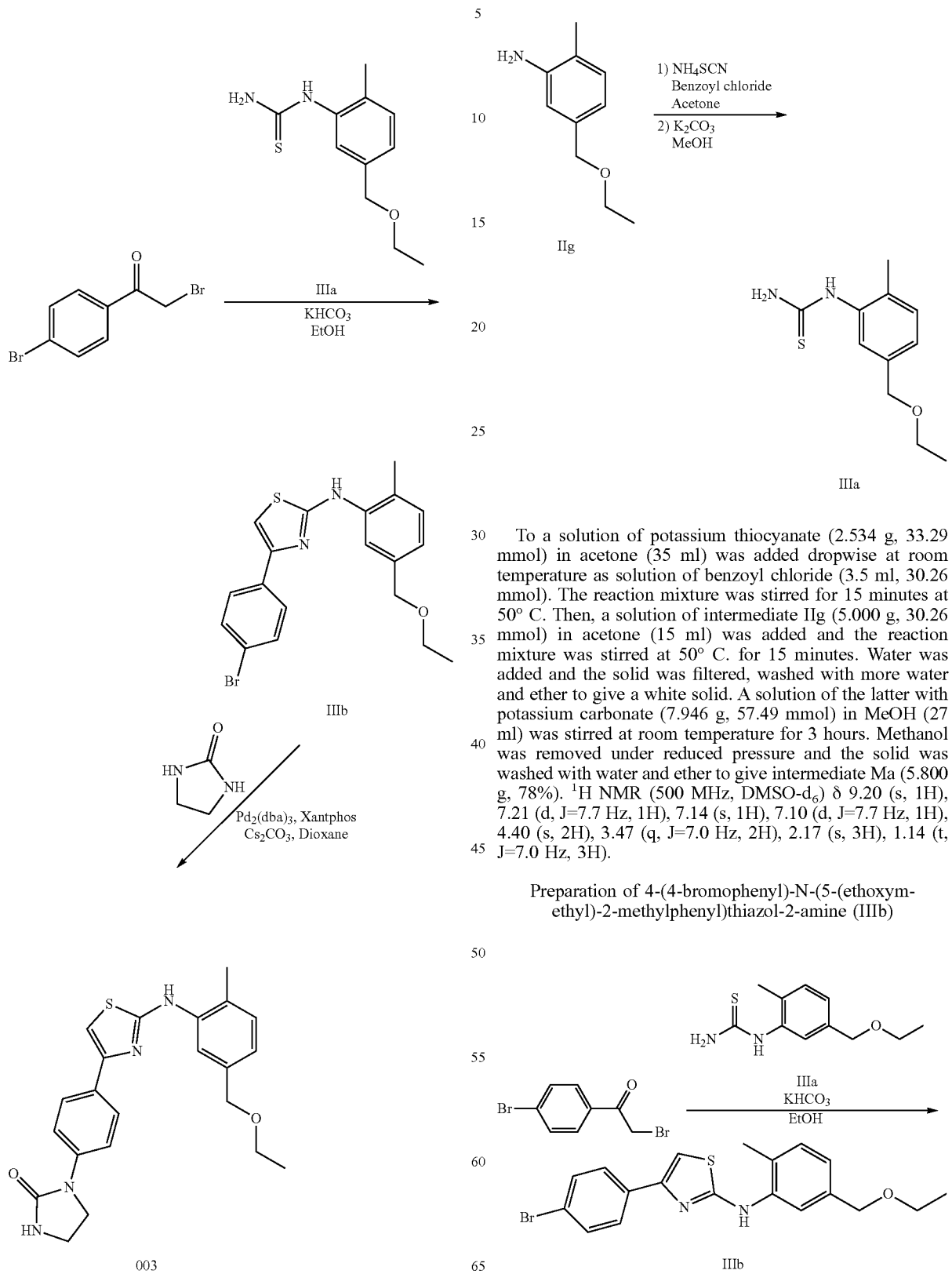

Preparation of 1-(5-(ethoxymethyl)-2-methylphenyl)thiourea (IIIc)

To a solution of potassium thiocyanate (2.534 g, 33.29 mmol) in acetone (35 ml) was added dropwise at room temperature as solution of benzoyl chloride (3.5 ml, 30.26 mmol). The reaction mixture was stirred for 15 minutes at 50° C. Then, a solution of intermediate IIg (5.000 g, 30.26 mmol) in acetone (15 ml) was added and the reaction mixture was stirred at 50° C. for 15 minutes. Water was added and the solid was filtered, washed with more water and ether to give a white solid. A solution of the latter with potassium carbonate (7.946 g, 57.49 mmol) in MeOH (27 ml) was stirred at room temperature for 3 hours. Methanol was removed under reduced pressure and the solid was washed with water and ether to give intermediate Ma (5.800 g, 78%). $^1$H NMR (500 MHz, DMSO-$d_6$) δ 9.20 (s, 1H), 7.21 (d, J=7.7 Hz, 1H), 7.14 (s, 1H), 7.10 (d, J=7.7 Hz, 1H), 4.40 (s, 2H), 3.47 (q, J=7.0 Hz, 2H), 2.17 (s, 3H), 1.14 (t, J=7.0 Hz, 3H).

Preparation of 4-(4-bromophenyl)-N-(5-(ethoxymethyl)-2-methylphenyl)thiazol-2-amine (IIIb)

To a solution of 2,4'-dibromoacetophenone (1.500 g, 5.39 mmol) in EtOH (54 ml) were added intermediate Ma (1.211 g, 5.39 mmol) and potassium hydrogen carbonate (1,621 g, 16.02 mmol). The reaction mixture was stirred at 80° C. for 16 hours. The cooled mixture was evaporated to dryness, diluted with water and extracted with EtOAc twice. The combined organics were dried over MgSO$_4$, filtered and evaporated. The final product was purified by silica gel chromatography using 0 to 30% EtOAc/cyclohexane as eluent to give intermediate IIIb (2.000 g, 92%). $^1$H NMR (500 MHz, DMSO-d$_6$) δ 9.37 (s, 1H), 8.01 (s, 1H), 7.82 (d, J=8.6 Hz, 2H), 7.58 (d, J=8.6 Hz, 2H), 7.35 (s, 1H), 7.18 (d, J=7.7 Hz, 1H), 6.95 (d, J=7.7 Hz, 1H), 4.44 (s, 2H), 3.50 (q, J=7.0 Hz, 2H), 2.27 (s, 3H), 1.16 (t, J=7.0 Hz, 3H).

Preparation of 1-{4-[2-(5-Ethoxymethyl-2-methyl-phenylamino)-thiazol-4-yl]-phenyl}-imidazolidin-2-one (003)

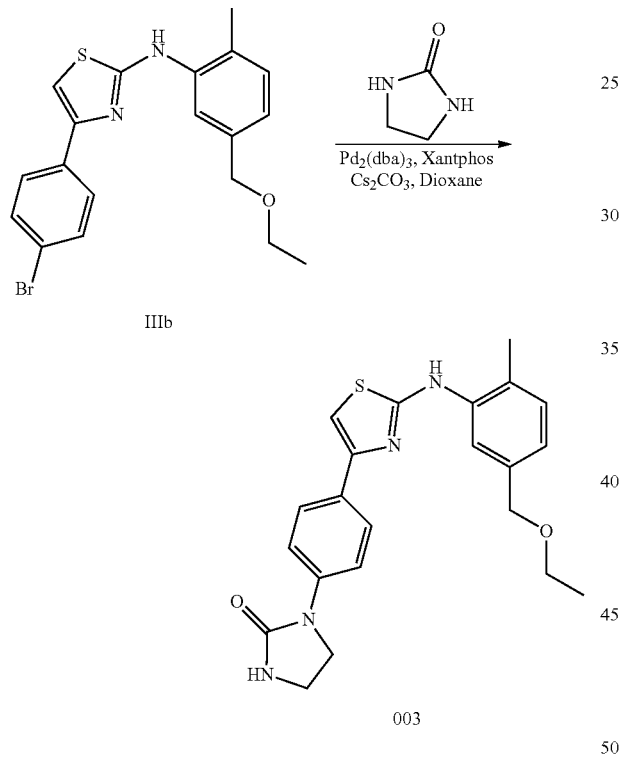

In a sealed tube, to a solution of IIIb (500 mg, 1.29 mmol) in dry dioxane (7 mL) were added successively 2-imidazolidinone (556 mg, 6.45 mmol), cesium carbonate (1.052 g, 3.23 mmol), Xantphos (75 mg, 0.13 mmol). The reaction mixture was degassed with nitrogen for 20 minutes before the addition of Pd$_2$(dba)$_3$ (35 mg, 0.04 mmol). Then, the reaction mixture was stirred at 110° C. for 16 hours. The cooled mixture was diluted with water and extracted with EtOAc twice. The combined organics were washed with water, with saturated solution of NaCl, dried over MgSO$_4$, filtered and evaporated. The final product was purified by silica gel chromatography using 60 to 90% EtOAc/cyclohexane as eluent to give intermediate 003 (260 mg, 52%). $^1$H NMR (500 MHz, DMSO-d$_6$) δ 9.29 (s, 1H), 8.05 (s, 1H), 7.81 (d, J=8.8 Hz, 2H), 7.58 (d, J=8.9 Hz, 2H), 7.18 (d, J=7.7 Hz, 1H), 7.12 (s, 1H), 6.96 (s, 1H), 6.93 (d, J=7.7 Hz, 1H), 4.44 (s, 2H), 3.91-3.83 (m, 2H), 3.50 (q, J=7.0 Hz, 2H), 3.45-3.37 (m, 2H), 2.27 (s, 3H), 1.17 (t, J=7.0 Hz, 3H).

A.4. Compound 004

Synthetic Approach of Compound 004

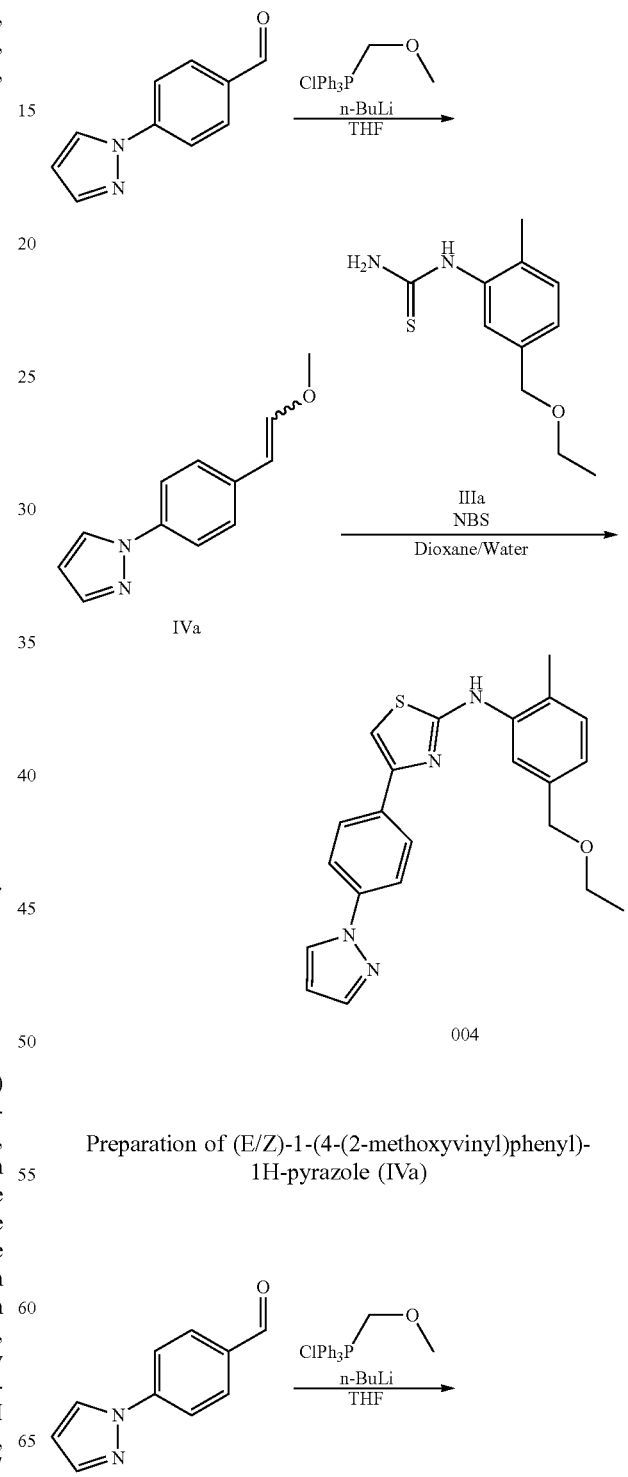

Preparation of (E/Z)-1-(4-(2-methoxyvinyl)phenyl)-1H-pyrazole (IVa)

-continued

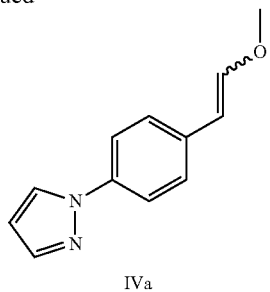

IVa

To a solution of (methoxymethyl)triphosphonium chloride (5.973 g, 17.43 mmol) in dry THF (40 mL) was added a solution of n-BuLi in dry THF (4.7 mL, 11.62 mmol) dropwise at 0° C. The reaction mixture was stirred at room temperature for 1 hour. Then, a solution of 4-(1H-pyrazol-1-yl)benzaldehyde (1.000 g; 5.81 mmol) in dry THF (20 mL) was added dropwise at 0° C. The reaction mixture was stirred at room temperature for 16 hours. The cooled mixture was diluted with a saturated solution of NH₄Cl and extracted with EtOAc twice. The combined organics were washed with water, with saturated solution of NaCl, dried over MgSO₄, filtered and evaporated. The final product was purified by silica gel chromatography using 0 to 20% EtOAc/cyclohexane as eluent to give intermediate (E/Z) 50/50 IVa (758 mg, 65%). ¹H NMR (500 MHz, CDCl₃) δ 7.90 (d, J=2.4 Hz, 1H), 7.88 (d, J=2.4 Hz, 1H), 7.71 (s, 2H), 7.65 (d, J=8.8 Hz, 2H), 7.62-7.56 (m, 4H), 7.30 (d, J=8.5 Hz, 2H), 7.07 (d, J=13.0 Hz, 1H), 6.47-6.43 (m, 2H), 6.17 (d, J=7.0 Hz, 1H), 5.83 (d, J=13.0 Hz, 1H), 5.24 (d, J=7.0 Hz, 1H), 3.80 (s, 3H), 3.70 (s, 3H).

Preparation of 5-(4-(1H-pyrazol-1-yl)phenyl)-N-(5-(ethoxymethyl)-2-methylphenyl)thiazol-2-amine (004)

To a solution of intermediate IVa (200 mg, 1.00 mmol) in dioxane/water (1/1 mL) was added N-bromosuccinimide (196 mg, 1.10 mmol). The reaction mixture was stirred at room temperature for 1 hour. Then, intermediate IIIa (224 mg, 1.00 mmol) was added and the reaction mixture was stirred at 80° C. for 16 hours. The cooled mixture was diluted with a saturated solution of NH₄Cl and extracted with EtOAc twice. The combined organics were washed with water, with saturated solution of NaCl, dried over MgSO₄, filtered and evaporated. The final product was purified by silica gel chromatography using 0 to 30% EtOAc/cyclohexane as eluent to give intermediate 004 (270 mg, 69%). ¹H NMR (500 MHz, DMSO-d₆) δ 9.42 (s, 1H), 8.50 (d, J=2.4 Hz, 1H), 7.83 (d, J=8.7 Hz, 2H), 7.79 (s, 1H), 7.75 (d, J=1.6 Hz, 1H), 7.67 (s, 1H), 7.60 (d, J=8.7 Hz, 2H), 7.20 (d, J=7.7 Hz, 1H), 6.98 (d, J=7.7 Hz, 1H), 6.60-6.52 (m, 1H), 4.42 (s, 2H), 3.48 (q, J=7.0 Hz, 2H), 2.27 (s, 3H), 1.15 (t, J=7.0 Hz, 3H).

A.5. Compound 005

Synthetic Approach of Compound 005

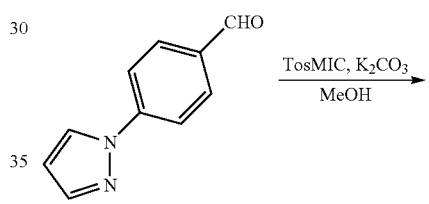

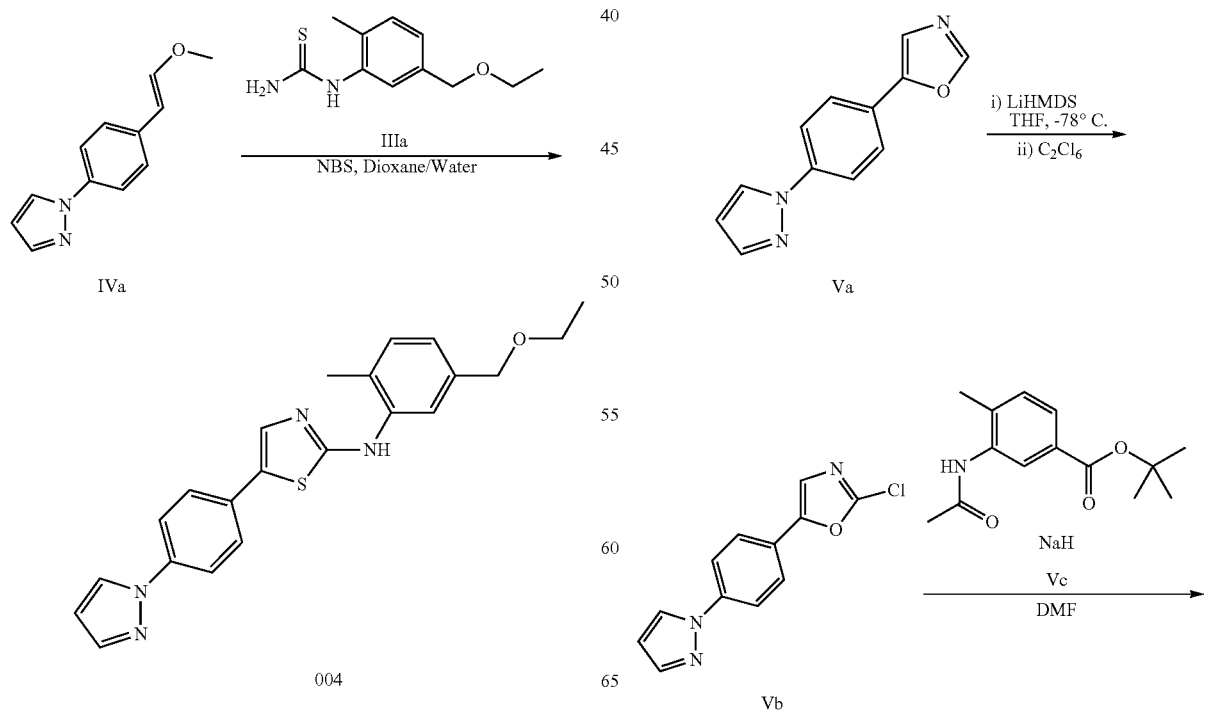

Preparation of 5-(4-(1H-pyrazol-1-yl)phenyl)oxazole (Va)

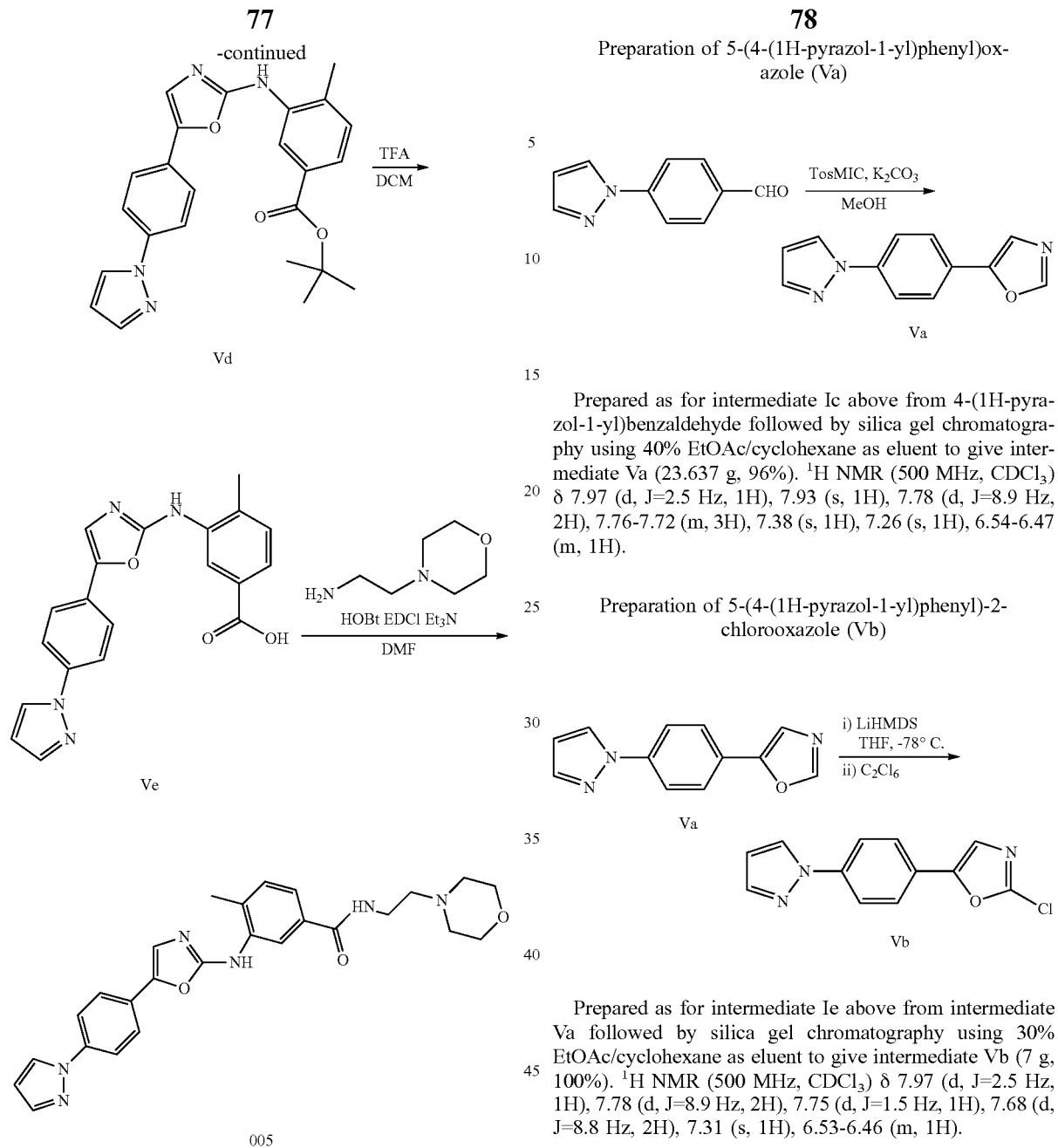

Prepared as for intermediate Ic above from 4-(1H-pyrazol-1-yl)benzaldehyde followed by silica gel chromatography using 40% EtOAc/cyclohexane as eluent to give intermediate Va (23.637 g, 96%). $^1$H NMR (500 MHz, CDCl$_3$) δ 7.97 (d, J=2.5 Hz, 1H), 7.93 (s, 1H), 7.78 (d, J=8.9 Hz, 2H), 7.76-7.72 (m, 3H), 7.38 (s, 1H), 7.26 (s, 1H), 6.54-6.47 (m, 1H).

Preparation of 5-(4-(1H-pyrazol-1-yl)phenyl)-2-chlorooxazole (Vb)

Prepared as for intermediate Ie above from intermediate Va followed by silica gel chromatography using 30% EtOAc/cyclohexane as eluent to give intermediate Vb (7 g, 100%). $^1$H NMR (500 MHz, CDCl$_3$) δ 7.97 (d, J=2.5 Hz, 1H), 7.78 (d, J=8.9 Hz, 2H), 7.75 (d, J=1.5 Hz, 1H), 7.68 (d, J=8.8 Hz, 2H), 7.31 (s, 1H), 6.53-6.46 (m, 1H).

Synthetic Approach of (Vc)

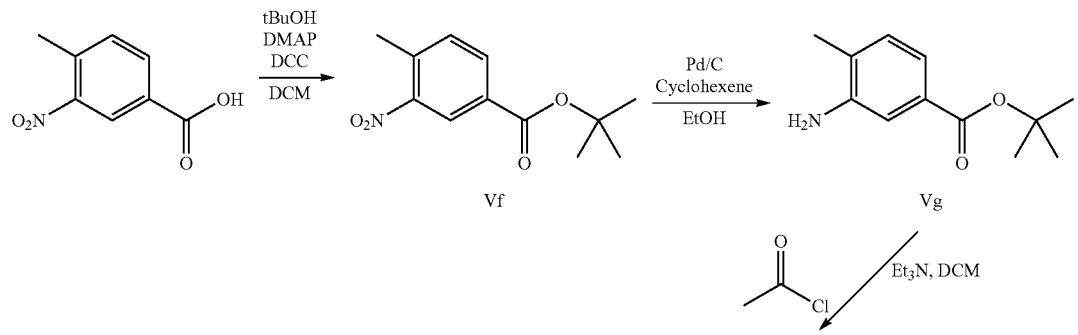

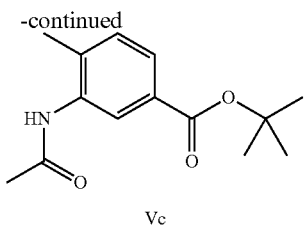
Vc

Preparation of tert-butyl 4-methyl-3-nitrobenzoate (Vf)

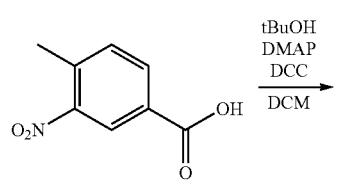

To a solution of 4-methyl-3-nitrobenzoic acid (6.000 g, 33.12 mmol) in dry DCM, were added successively DMAP (404 mg, 3.312 mmol), t-BuOH (2.946 g, 27.602 mmol) and DCC (8.200 g, 27.602 mmol) at 0° C. The reaction mixture was stirred at room temperature for 48 hours. Then, the reaction mixture was filtered, washed with more DCM, and the filtrate was concentrated. The final product was purified by silica gel chromatography using 0 to 20% EtOAc/cyclohexane as eluent to give intermediate Vf (6.793 g, 86%). $^1$H NMR (300 MHz, CDCl$_3$) δ 8.51 (d, J=1.6 Hz, 1H), 8.08 (dd, J=8.0, 1.7 Hz, 1H), 7.40 (d, J=8.0 Hz, 1H), 2.64 (s, 3H), 1.60 (s, 9H).

Preparation of tert-butyl 3-amino-4-methylbenzoate (Vg)

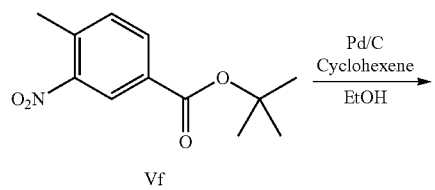

To a solution of intermediate Vf (6.793 g, 28.64 mmol) in EtOH (60 ml) and degassed with nitrogen were added Pd/C (1.200 g) and cyclohexene (60 ml). The reaction mixture was stirred at 80° C. for 16 hours. The reaction mixture filtered over Celite® pad, washed with more EtOH and the filtrate was concentrated to give intermediate Vg (6.200 g, 100%). $^1$H NMR (300 MHz, CDCl$_3$) δ 7.32 (d, J=7.8 Hz, 1H), 7.29 (s, 1H), 7.07 (d, J=7.8 Hz, 1H), 3.68 (s, 2H), 2.20 (s, 3H), 1.57 (s, 9H).

Preparation of tert-butyl 3-acetamido-4-methylbenzoate (Vc)

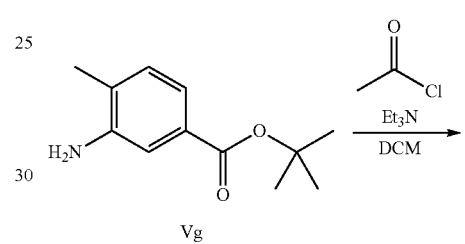

Prepared as for intermediate If above from intermediate Vg followed by purification by silica gel chromatography using 25 to 40% EtOAc/cyclohexane as eluent to afford intermediate Vc (6.296 g, 84%). $^1$H NMR (300 MHz, CDCl$_3$) δ 8.17 (s, 1H), 7.71 (d, J=7.7 Hz, 1H), 7.21 (d, J=8.0 Hz, 2H), 2.27 (s, 3H), 2.19 (s, 3H), 1.57 (s, 9H).

Preparation of tert-butyl 3-(5-(4-(1H-pyrazol-1-yl)phenyl)oxazol-2-ylamino)-4-methylbenzoate (Vd)

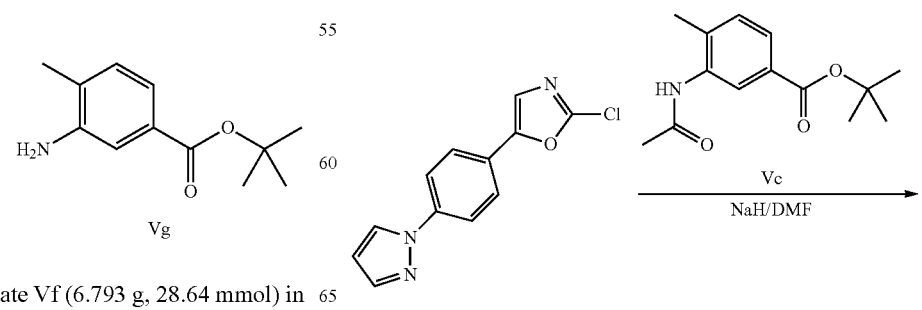

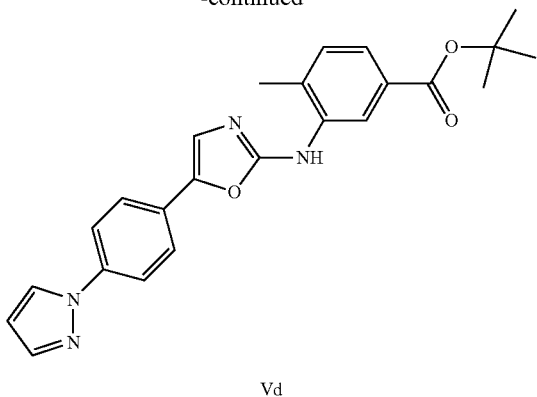

Vd

Prepared as for 001 above from intermediates Vb and Vc followed by purification by silica gel chromatography using 10 to 40% EtOAc/cyclohexane as eluent to afford intermediate Vf (1.100 g, 65%). $^1$H NMR (300 MHz, DMSO-d$_6$) δ 9.47 (s, 1H), 8.54 (d, J=2.3 Hz, 1H), 8.51 (d, J=1.5 Hz, 1H), 7.92 (d, J=8.8 Hz, 2H), 7.76 (d, J=1.5 Hz, 1H), 7.70 (d, J=8.8 Hz, 2H), 7.53 (d, J=1.6 Hz, 1H), 7.50 (s, 1H), 7.32 (d, J=7.9 Hz, 1H), 6.59-6.52 (m, 1H), 2.36 (s, 3H), 1.54 (s, 9H).

Preparation of 3-(5-(4-(1H-pyrazol-1-yl)phenyl) oxazol-2-ylamino)-4-methylbenzoic acid (Ve)

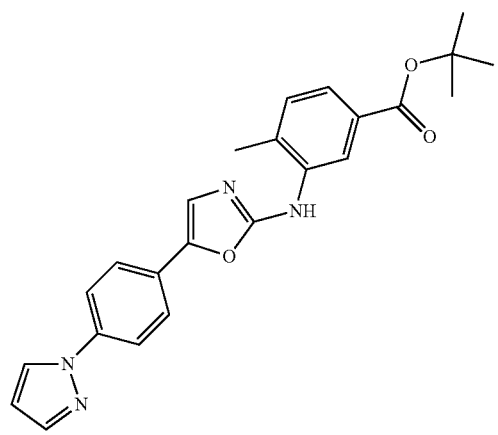

To a solution of intermediate Vd (1.100 g, 2.64 mmol) in DCM (13 ml) was added dropwise TFA (2.7 ml). The reaction mixture was stirred at room temperature for 16 hours. The reaction mixture was concentrated, the solid was triturated in Et$_2$O and filtered to give intermediate Ve (1.200 g, 96%). $^1$H NMR (300 MHz, DMSO-d$_6$) δ 9.55 (s, 1H), 8.57 (d, J=1.3 Hz, 1H), 8.54 (d, J=2.4 Hz, 1H), 7.93 (d, J=8.7 Hz, 2H), 7.76 (d, J=1.6 Hz, 1H), 7.71 (d, J=8.7 Hz, 2H), 7.57 (dd, J=7.8, 1.5 Hz, 1H), 7.53 (s, 1H), 7.33 (d, J=7.9 Hz, 1H), 6.62-6.48 (m, 1H), 2.37 (s, 3H).

Preparation of 3-(5-(4-(1H-pyrazol-1-yl)phenyl) oxazol-2-ylamino)-4-methyl-N-(2-morpholinoethyl) benzamide (005)

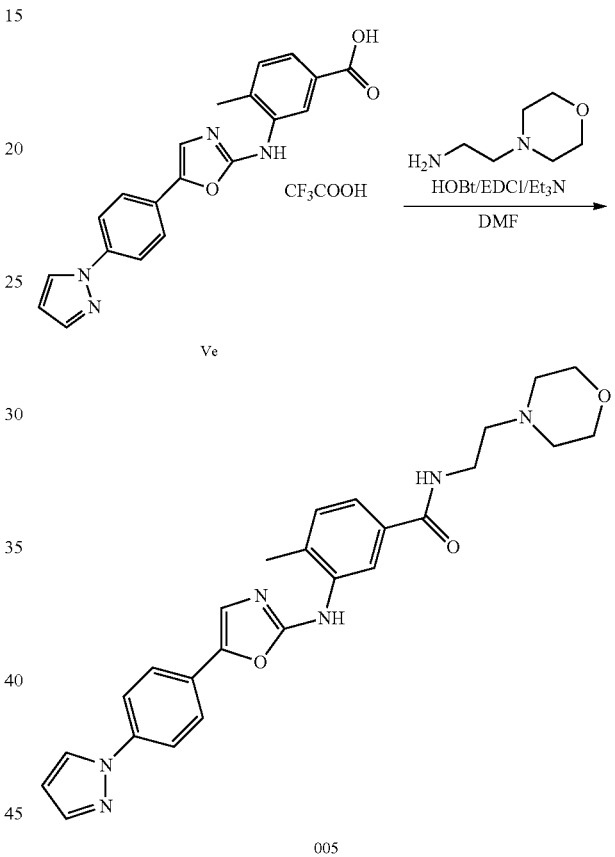

To a solution of intermediate Ve (200 mg, 0.42 mmol) in dry DMF (2 ml) were added successively HOBt (83 mg, 0.61 mmol), EDCI (159 mg, 0.83 mmol), Et$_3$N (464 µl, 6.32 mmol) and 2-morpholinoethanamine (72 µl, 0.55 mmol). The reaction mixture was stirred at room temperature for 16 hours. The mixture was diluted with water and extracted with EtOAc twice. The combined organics were washed with a saturated solution of NaHCO$_3$ (3 times), with water, with saturated solution of NaCl, dried over MgSO$_4$, filtered and evaporated. The final product was purified by silica gel chromatography using 0 to 20% MeOH/EtOAC as eluent to give 005 (165 mg, 83%). $^1$H NMR (300 MHz, DMSO-d$_6$) δ 9.41 (s, 1H), 8.54 (d, J=2.4 Hz, 1H), 8.32 (s, 1H), 8.29 (d, J=5.7 Hz, 1H), 7.92 (d, J=8.8 Hz, 2H), 7.76 (d, J=1.6 Hz, 1H), 7.69 (d, J=8.7 Hz, 2H), 7.47 (s, 1H), 7.45 (dd, J=7.9, 1.7 Hz, 1H), 7.28 (d, J=7.9 Hz, 1H), 6.59-6.53 (m, 1H), 3.61-3.52 (m, 4H), 3.42-3.33 (m, 2H), 2.47 (m, 2H), 2.42 (m, 4H), 2.34 (s, 3H).

83
A.6. Compound 006

Synthetic Approach of Compound 006

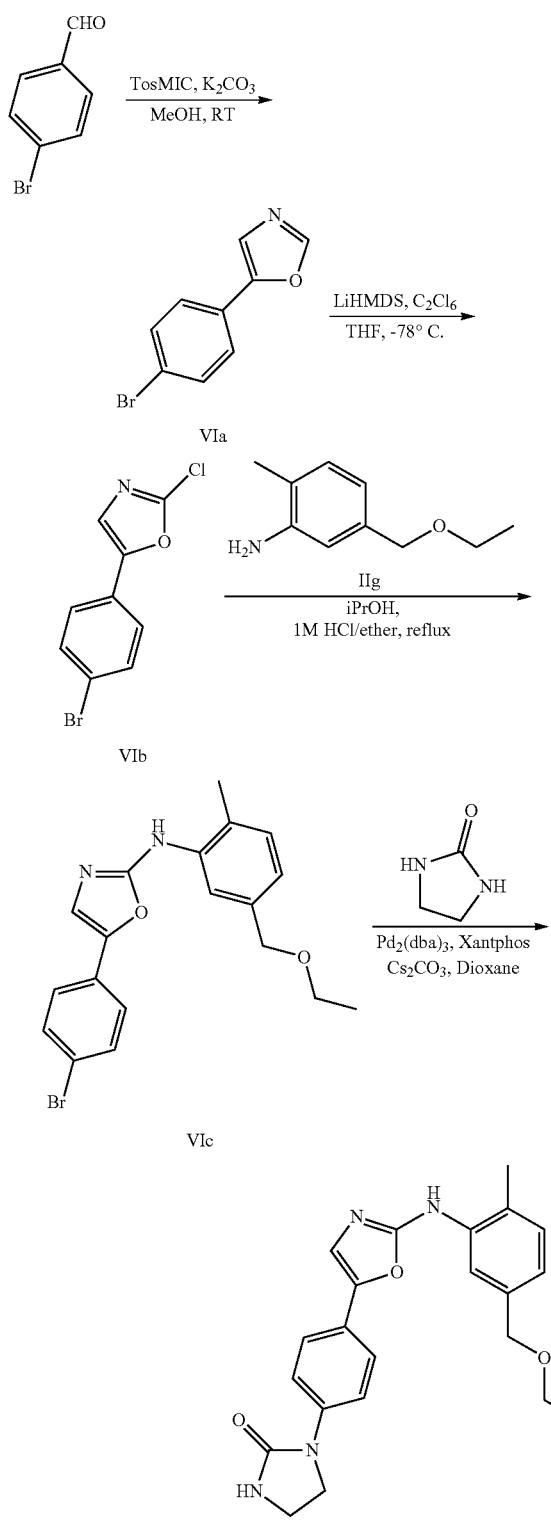

84
Preparation of 5-(4-bromophenyl)oxazole (VIa)

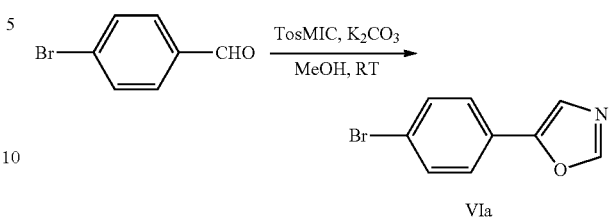

Prepared as for intermediate Ic above from 4-bromobenzaldehyde to give intermediate VIa (15.000 g, 95%). $^1$H NMR (300 MHz, CDCl$_3$) δ 7.92 (s, 1H), 7.56 (d, J=8.8 Hz, 2H), 7.51 (d, J=8.8 Hz, 2H), 7.36 (s, 1H).

Preparation of 5-(4-bromophenyl)-2-chlorooxazole (VIb)

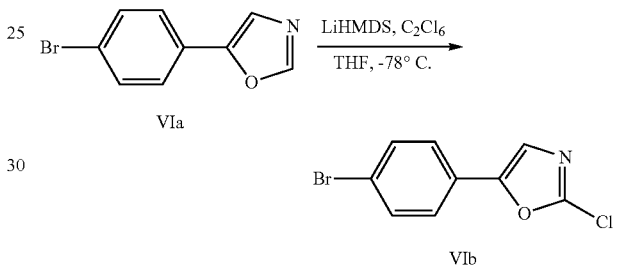

Prepared as for intermediate Ic above from intermediate VIa followed by silica gel chromatography using 5% EtOAc/cyclohexane as eluent to give intermediate VIb (9.000 g, 98%). $^1$H NMR (300 MHz, CDCl$_3$) δ 7.57 (d, J=8.6 Hz, 2H), 7.46 (d, J=8.6 Hz, 2H), 7.29 (s, 1H).

Preparation of 5-(4-bromophenyl)-N-(5-(ethoxymethyl)-2-methylphenyl)oxazol-2-amine (VIc)

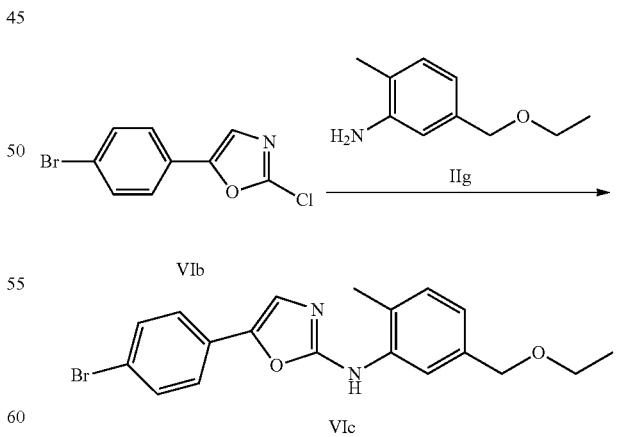

Prepared as for 002 above from intermediates VIb and IIg followed by silica gel chromatography using 0 to 20% EtOAc/cyclohexane as eluent to give intermediate VIc (4.234 g, 68%). $^1$H NMR (300 MHz, DMSO-d$_6$) δ 9.32 (s, 1H), 7.79 (s, 1H), 7.61 (d, J=8.6 Hz, 2H), 7.50 (d, J=9.9 Hz, 3H), 7.16 (d, J=7.7 Hz, 1H), 6.93 (d, J=7.6 Hz, 1H), 4.40 (s, 2H), 3.47 (q, J=7.0 Hz, 2H), 2.27 (s, 3H), 1.14 (t, J=7.0 Hz, 3H).

Preparation of 1-{4-[2-(5-Ethoxymethyl-2-methyl-phenylamino)-oxazol-5-yl]-phenyl}-imidazolidin-2-one (006)

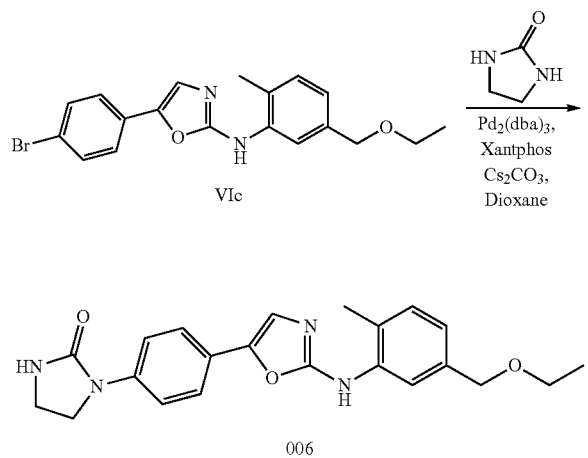

In a sealed tube, to a solution of VIc (500 mg, 1.29 mmol) in dry dioxane (7 mL) were added successively 2-imidazolidinone (556 mg, 6.45 mmol), cesium carbonate (1.052 g, 3.23 mmol), Xantphos (75 mg, 0.13 mmol). The reaction mixture was degassed with nitrogen for 20 minutes before the addition of $Pd_2(dba)_3$ (35 mg, 0.04 mmol). Then, the reaction mixture was stirred at 110° C. for 16 hours. The cooled mixture was diluted with water and extracted with EtOAc twice. The combined organics were washed with water, with saturated solution of NaCl, dried over $MgSO_4$, filtered and evaporated. The final product was purified by silica gel chromatography using 10 to 50% EtOAc/cyclohexane as eluent to give intermediate 006 (260 mg, 52%). $^1$H NMR (500 MHz, DMSO-$d_6$) δ 9.16 (s, 1H), 7.84 (s, 1H), 7.63 (d, J=8.9 Hz, 2H), 7.52 (d, J=8.8 Hz, 2H), 7.28 (s, 1H), 7.16 (d, J=7.7 Hz, 1H), 7.00 (s, 1H), 6.93 (d, J=7.6 Hz, 1H), 4.42 (s, 2H), 3.91-3.85 (m, 2H), 3.48 (q, J=7.0 Hz, 2H), 3.45-3.38 (m, 2H), 2.28 (s, 3H), 1.15 (t, J=7.0 Hz, 3H).

A.7. Compounds 007-064

Compounds 007-050 of table 1 were synthesized according to methods described above and general synthetic procedures.

B. Pharmacological Example—Anti-Tumoral Activity

B.1. Introduction

By the mid-1980s, many tumor cell lines had been established worldwide, and many were available from repositories such as American Type Culture Collection. In the late 1980s, the 'US National Cancer Institute 60 human tumor cell line anticancer drug screen' (NCI60) was developed as a screening tool of compounds for growth inhibitory activity. Consisting of 60 human tumor cell lines that represent 9 cancer types, the NCI60 has been a compound evaluation resource for the research community (Sharma et al., Nature Reviews, 2010, 10, 241; Shoemaker, Nature Reviews, 2006, 6, 813).

This high throughput cell-based profiling approach was crucial to the discovery of several agents that have subsequently been found to demonstrate therapeutic activity. Perhaps the most notable contribution of the NCI60 to current chemotherapy was the development of the proteasome inhibitor Bortezomib which was approved by the FDA in 2003.

Although the physiological relevance and usefulness of this approach for assessing drug efficacy remain controversial, most investigators agree that this remain our best tools for identification and characterization of medicinal agents that can potentially produce clinical benefit in cancer patients.

Compounds of formula (I) were tested against a panel of about 34 human tumor cell lines representing 17 cancer type, namely leukemia (represented by 1 cell line), lymphoma (4 cell lines), myeloma (1 cell line), colorectal (2 cell lines), head and neck (3 cell lines), lung (3 cell lines), melanoma (2 cell lines), pancreas (2 cell lines), prostate (2 cell lines), ovary (2 cell lines) breast (2 cell lines), kidney (2 cell lines), stomach (2 cell lines), liver (2 cell lines), glioblastoma (2 cell lines), osteosarcoma (1 cell line), Ewing Sarcoma (1 cell line).

B.2. Methods

Cell-Based Proliferation Screening of Compounds

CellTiter-Blue cell-based survival/proliferation assay (Promega G8080) was performed on tumor cell lines. A total of $1·10^4$ cells/well/50 μl were seeded in a 96-wells plate. Treatment was initiated by addition of a 2× drug solution of 1/10 serial dilutions ranging from 0 to 10 μM. Cells were grown for 48 h at 37° C. and then incubated with 10 μl/well of Promega CellTiter-Bleue reagent for 4 h at 37° C. The amount of resorufin dye formed was quantified by its fluorescence emission at 590 nm using a scanning multiwell spectrophotometer (OPTIMA, BMG labtech, France). A blank well without cells was used as a background control for the spectrophotometer.

Examples of Cell Lines Tested

A375, A4513, A498, A549, ACHN, AGS, BT20, BXPC3, CALU6, CLS354, DLD1, DU145, H1299, HCT116, HEP2, HEPG2, HGC27, HL60, HUT78, KARPAS299, MDAMB231, MELWO, MESSA, OPM2, PANC1, PC3, PLCPRF5, REC1, RL, SW579, TOV112D, U118, U2OS, U87MG.

B.3. Results

Anti-Tumoral Activity of Compounds of Formula (I)

TABLE 2

Anti-tumoral activity of compounds of formula (I) on hematopoietic tumor cell lines (measured IC50).

| Example | Leukemia | Lymphoma | | | | Myeloma |
| --- | --- | --- | --- | --- | --- | --- |
| | HL60 | HUT78 | KARPAS299 | REC1 | RL | OPM2 |
| 001 | + | + | ++ | ++ | N.D. | + |
| 002 | + | + | + | + | N.D. | + |
| 003 | ++++ | ++++ | ++++ | ++++ | N.D. | ++++ |
| 004 | + | + | + | + | N.D. | + |
| 005 | + | + | + | + | N.D. | + |
| 006 | ++++ | ++++ | ++++ | ++++ | N.D. | ++++ |
| 007 | +++ | ++++ | ++++ | ++++ | N.D. | +++ |
| 008 | ++++ | ++++ | ++++ | ++++ | N.D. | ++++ |
| 009 | + | N.D. | N.D. | N.D. | N.D. | + |
| 010 | ++++ | ++++ | ++++ | ++++ | N.D. | ++++ |
| 011 | + | + | + | + | N.D. | + |
| 012 | N.D. | N.D. | N.D. | N.D. | N.D. | N.D. |
| 013 | +++ | ++ | ++ | ++ | N.D. | +++ |
| 014 | + | + | +++ | + | N.D. | + |
| 015 | ++++ | ++++ | ++++ | ++++ | N.D. | +++ |
| 016 | + | + | + | + | N.D. | + |
| 017 | + | + | + | + | N.D. | + |
| 018 | ++++ | ++++ | ++++ | ++++ | N.D. | ++++ |
| 019 | N.D. | N.D. | N.D. | N.D. | N.D. | N.D. |
| 020 | ++++ | ++++ | ++++ | ++++ | N.D. | ++++ |
| 021 | +++ | ++ | +++ | +++ | N.D. | +++ |
| 022 | + | + | +++ | ++ | N.D. | ++ |
| 023 | +++ | +++ | +++ | +++ | N.D. | +++ |
| 024 | + | + | + | + | N.D. | + |
| 025 | + | + | + | + | N.D. | + |
| 026 | + | + | + | + | N.D. | + |
| 027 | + | + | + | + | N.D. | + |
| 028 | N.D. | N.D. | N.D. | N.D. | N.D. | N.D. |
| 029 | + | + | + | + | N.D. | + |
| 030 | + | + | + | + | N.D. | + |
| 031 | + | + | +++ | + | N.D. | + |
| 032 | + | + | + | + | N.D. | + |
| 033 | ++++ | ++++ | ++++ | ++++ | N.D. | ++++ |
| 034 | + | +++ | +++ | +++ | N.D. | + |
| 035 | + | ++ | ++ | ++ | N.D. | + |
| 036 | +++ | ++++ | ++++ | ++++ | N.D. | +++ |
| 037 | + | + | + | N.D. | + | + |
| 038 | +++ | + | + | +++ | N.D. | +++ |
| 039 | ++ | ++ | ++ | ++ | N.D. | + |
| 040 | + | + | + | + | N.D. | + |
| 041 | ++ | N.D. | N.D. | N.D. | N.D. | ++ |
| 042 | N.D. | N.D. | N.D. | N.D. | N.D. | N.D. |
| 043 | ++ | N.D. | N.D. | N.D. | N.D. | ++ |
| 044 | +++ | ++ | +++ | +++ | N.D. | ++ |
| 045 | + | + | + | + | N.D. | + |
| 046 | + | + | + | + | N.D. | + |
| 047 | N.D. | N.D. | N.D. | N.D. | N.D. | N.D. |
| 048 | +++ | ++ | ++ | ++ | N.D. | ++ |
| 049 | + | + | + | + | N.D. | + |
| 050 | ++ | + | +++ | ++ | N.D. | ++ |
| 051 | ++++ | N.D. | N.D. | N.D. | N.D. | ++++ |
| 052 | + | N.D. | N.D. | N.D. | N.D. | + |
| 053 | ++++ | N.D. | N.D. | N.D. | N.D. | ++++ |
| 054 | + | N.D. | N.D. | N.D. | N.D. | + |
| 055 | ++++ | N.D. | N.D. | N.D. | N.D. | ++++ |
| 056 | ++++ | N.D. | N.D. | N.D. | N.D. | ++++ |
| 057 | +++ | N.D. | N.D. | N.D. | N.D. | +++ |
| 058 | ++++ | N.D. | N.D. | N.D. | N.D. | ++++ |
| 059 | ++++ | N.D. | N.D. | N.D. | N.D. | ++++ |

TABLE 2-continued

Anti-tumoral activity of compounds of formula (I) on hematopoietic tumor cell lines (measured IC50).

| | Leukemia | Lymphoma | | | | Myeloma |
|---|---|---|---|---|---|---|
| Example | HL60 | HUT78 | KARPAS299 | REC1 | RL | OPM2 |
| 060 | ++ | N.D. | N.D. | N.D. | N.D. | ++ |
| 061 | + | N.D. | N.D. | N.D. | N.D. | + |
| 062 | +++ | N.D. | N.D. | N.D. | N.D. | +++ |
| 063 | N.D. | N.D. | N.D. | N.D. | N.D. | N.D. |
| 064 | N.D. | N.D. | N.D. | N.D. | N.D. | N.D. |

The IC50 given in table 2 above are expressed as:
++++: IC50 ≤ 100 nM
+++: 100 < IC50 ≤ 500 nM
++: 500 < IC50 ≤ 1000 nM
+: IC50 > 1000 nM
N.D.: Not Determined

TABLE 3

Anti-tumoral activity of compounds of formula (I) on solid tumor cell lines (measured IC50).

| | Lung | | | Breast | | Head & Neck | | |
|---|---|---|---|---|---|---|---|---|
| Ex. | A549 | CALU6 | H1299 | BT20 | MDAMB231 | CLS354_4 | HEP2 | SW579 |
| 001 | + | + | + | + | + | + | + | + |
| 002 | + | + | + | + | + | + | + | + |
| 003 | + | + | + | + | ++++ | ++++ | + | + |
| 004 | + | + | + | + | + | + | + | + |
| 005 | + | + | + | + | + | + | + | + |
| 006 | + | + | + | +++ | ++++ | ++++ | + | + |
| 007 | + | + | + | + | + | ++++ | +++ | + |
| 008 | N.D. | + | + | + | + | +++ | ++++ | ++ |
| 009 | + | + | + | + | + | + | + | + |
| 010 | + | ++ | +++ | + | + | ++++ | ++++ | ++++ |
| 011 | + | + | + | + | + | + | + | + |
| 012 | N.D. | N.D. | N.D. | N.D. | N.D. | N.D. | N.D. | N.D. |
| 013 | + | + | + | + | + | + | + | + |
| 014 | + | + | + | + | + | + | + | + |
| 015 | + | + | + | + | + | ++++ | + | + |
| 016 | + | + | + | + | + | + | + | + |
| 017 | + | + | + | + | + | + | + | + |
| 018 | ++++ | + | + | + | + | ++++ | ++++ | + |
| 019 | N.D. | N.D. | N.D. | N.D. | N.D. | N.D. | N.D. | N.D. |
| 020 | + | + | + | + | +++ | ++++ | + | + |
| 021 | + | + | + | + | + | +++ | + | + |
| 022 | + | + | + | + | + | + | + | + |
| 023 | + | + | + | + | + | +++ | + | + |
| 024 | + | + | + | + | + | + | + | + |
| 025 | + | + | + | + | + | + | + | + |
| 026 | + | + | + | + | + | + | + | + |
| 027 | + | + | + | + | + | + | + | + |
| 028 | N.D. | N.D. | N.D. | N.D. | N.D. | N.D. | N.D. | N.D. |
| 029 | + | + | + | + | + | + | + | + |
| 030 | + | + | + | + | + | + | + | + |
| 031 | + | + | + | + | + | + | + | + |
| 032 | + | + | + | + | + | + | + | + |
| 033 | + | ++++ | + | +++ | + | ++++ | ++++ | + |
| 034 | + | + | + | + | + | ++ | ++ | + |
| 035 | + | + | + | + | + | + | + | + |
| 036 | + | ++ | ++ | ++ | + | ++++ | +++ | + |
| 037 | + | + | + | + | + | + | + | + |
| 038 | + | + | + | + | + | + | ++ | + |
| 039 | + | + | + | + | + | + | + | + |
| 040 | + | + | + | + | + | + | + | + |
| 041 | + | + | + | + | + | + | + | + |
| 042 | N.D. | N.D. | N.D. | N.D. | N.D. | N.D. | N.D. | N.D. |
| 043 | + | + | + | + | + | + | + | + |
| 044 | + | + | + | + | + | ++ | + | + |
| 045 | + | + | + | + | + | + | + | + |
| 046 | + | + | + | + | + | + | + | + |
| 047 | N.D. | N.D. | N.D. | N.D. | N.D. | N.D. | N.D. | N.D. |
| 048 | + | + | + | + | + | ++ | + | + |
| 049 | + | + | + | + | + | + | + | + |

TABLE 3-continued

Anti-tumoral activity of compounds of formula (I) on solid tumor cell lines (measured IC50).

| | | | | | | | | |
|---|---|---|---|---|---|---|---|---|
| 050 | + | + | + | + | + | + | + | + |
| 051 | + | + | + | + | + | ++++ | +++ | + |
| 052 | + | + | + | + | + | + | + | + |
| 053 | + | + | + | + | + | ++++ | ++++ | + |
| 054 | + | + | + | + | + | + | + | + |
| 055 | ++++ | + | + | + | + | ++++ | ++++ | ++++ |
| 056 | + | + | + | + | + | ++++ | ++++ | ++++ |
| 057 | + | + | + | + | + | +++ | ++ | + |
| 058 | + | + | + | + | + | ++++ | +++ | + |
| 059 | + | + | + | + | + | ++++ | ++++ | ++++ |
| 060 | + | + | + | + | + | + | + | + |
| 061 | + | + | + | + | + | + | + | + |
| 062 | + | + | + | + | + | ++ | ++ | + |
| 063 | N.D. | N.D. | N.D. | N.D. | N.D. | N.D. | N.D. | N.D. |
| 064 | N.D. | N.D. | N.D. | N.D. | N.D. | N.D. | N.D. | N.D. |

| | Pancreas | | Stomach | | Liver | |
|---|---|---|---|---|---|---|
| Ex. | BXPC3 | PANC_1 | AGS | HGC27 | HEPG2 | PLC_PRF5 |
| 001 | + | + | + | + | + | + |
| 002 | + | + | + | + | + | + |
| 003 | ++++ | + | + | + | + | + |
| 004 | + | + | + | + | + | + |
| 005 | + | + | + | + | + | + |
| 006 | ++++ | + | + | + | + | + |
| 007 | + | + | ++++ | +++ | + | + |
| 008 | + | + | + | ++ | + | + |
| 009 | + | + | + | + | + | + |
| 010 | + | + | + | ++++ | + | + |
| 011 | + | + | + | + | + | + |
| 012 | N.D. | N.D. | N.D. | N.D. | N.D. | N.D. |
| 013 | + | + | + | + | + | + |
| 014 | + | + | + | + | + | + |
| 015 | + | + | + | + | + | + |
| 016 | + | + | + | + | + | + |
| 017 | + | + | + | + | + | + |
| 018 | + | + | + | ++ | + | + |
| 019 | N.D. | N.D. | N.D. | N.D. | N.D. | N.D. |
| 020 | ++ | + | + | + | + | + |
| 021 | + | + | + | + | + | + |
| 022 | + | + | + | + | + | + |
| 023 | + | + | + | + | + | + |
| 024 | + | + | + | + | + | + |
| 025 | + | + | + | + | + | + |
| 026 | + | + | + | + | + | + |
| 027 | + | + | + | + | + | + |
| 028 | N.D. | N.D. | N.D. | N.D. | N.D. | N.D. |
| 029 | + | + | + | + | + | + |
| 030 | + | + | + | + | + | + |
| 031 | + | + | + | + | + | + |
| 032 | + | + | + | + | + | + |
| 033 | +++ | + | ++++ | ++++ | ++ | ++ |
| 034 | + | + | + | + | + | + |
| 035 | + | + | + | + | + | + |
| 036 | + | + | ++++ | ++++ | +++ | + |
| 037 | + | + | + | + | + | + |
| 038 | + | + | + | + | + | + |
| 039 | + | + | + | + | + | + |
| 040 | + | + | + | + | + | + |
| 041 | + | + | + | + | + | + |
| 042 | N.D. | N.D. | N.D. | N.D. | N.D. | N.D. |
| 043 | + | + | + | + | + | + |
| 044 | + | + | + | + | + | + |
| 045 | + | + | + | + | + | + |
| 046 | + | + | + | + | + | + |
| 047 | N.D. | N.D. | N.D. | N.D. | N.D. | N.D. |
| 048 | + | + | + | + | + | + |
| 049 | + | + | + | + | + | + |
| 050 | + | + | + | + | + | + |
| 051 | + | + | + | + | + | + |
| 052 | + | + | + | + | + | + |
| 053 | + | + | +++ | +++ | + | + |
| 054 | + | + | + | + | + | + |
| 055 | + | + | + | ++ | + | + |
| 056 | + | + | + | + | + | + |
| 057 | + | + | + | + | + | + |

TABLE 3-continued

Anti-tumoral activity of compounds of formula
(I) on solid tumor cell lines (measured IC50).

| | | | | | | |
|---|---|---|---|---|---|---|
| 058 | + | + | + | + | + | + |
| 059 | ++ | + | + | + | + | + |
| 060 | + | + | + | + | + | + |
| 061 | + | + | + | + | + | + |
| 062 | + | + | + | + | + | + |
| 063 | N.D. | N.D. | N.D. | N.D. | N.D. | N.D. |
| 064 | N.D. | N.D. | N.D. | N.D. | N.D. | N.D. |

| | Colorectal | | Kidney | | Ovary | | Prostate | |
|---|---|---|---|---|---|---|---|---|
| Ex. | DLD_1 | HCT116 | A498 | ACHN | MESSA | TOV112D | DU145 | PC3 |
| 001 | + | + | + | + | + | + | + | + |
| 002 | + | + | + | + | + | + | + | + |
| 003 | ++++ | ++ | ++++ | ++++ | +++ | ++++ | + | ++++ |
| 004 | + | + | + | + | + | + | + | + |
| 005 | + | + | + | + | + | + | + | + |
| 006 | ++++ | + | +++ | ++++ | + | ++++ | + | ++++ |
| 007 | ++ | + | + | +++ | + | ++++ | + | +++ |
| 008 | + | ++++ | + | ++++ | + | ++++ | + | ++++ |
| 009 | + | + | + | + | + | + | + | + |
| 010 | + | ++++ | + | ++++ | + | ++++ | + | ++++ |
| 011 | + | + | + | + | + | + | + | + |
| 012 | N.D. | N.D. | N.D. | N.D. | N.D. | N.D. | N.D. | N.D. |
| 013 | + | + | + | + | + | + | + | ++ |
| 014 | + | + | + | + | + | + | + | + |
| 015 | + | + | ++ | + | + | ++ | + | ++++ |
| 016 | + | + | + | + | + | + | + | + |
| 017 | + | + | + | + | + | + | + | + |
| 018 | + | +++ | ++ | ++ | + | ++++ | + | + |
| 019 | N.D. | N.D. | N.D. | N.D. | N.D. | N.D. | N.D. | N.D. |
| 020 | +++ | + | + | + | + | + | + | ++++ |
| 021 | ++ | + | + | + | + | + | + | ++ |
| 022 | + | + | + | + | + | + | + | + |
| 023 | + | + | + | + | + | + | + | + |
| 024 | + | + | + | + | + | + | + | + |
| 025 | + | + | + | + | + | + | + | + |
| 026 | + | + | + | + | + | + | + | + |
| 027 | + | + | + | + | + | + | + | + |
| 028 | N.D. | N.D. | N.D. | N.D. | N.D. | N.D. | N.D. | N.D. |
| 029 | + | + | + | + | + | + | + | + |
| 030 | + | + | + | + | + | + | + | + |
| 031 | + | + | + | + | + | + | + | + |
| 032 | + | + | + | + | + | + | + | + |
| 033 | ++++ | +++ | +++ | ++++ | +++ | ++++ | + | ++++ |
| 034 | + | + | + | + | + | ++ | + | + |
| 035 | + | + | + | + | + | ++ | + | + |
| 036 | + | + | + | +++ | + | ++++ | + | +++ |
| 037 | + | + | + | + | + | + | + | + |
| 038 | + | + | + | + | + | + | + | + |
| 039 | + | + | + | + | + | + | + | + |
| 040 | + | + | + | + | + | + | + | + |
| 041 | + | + | + | + | + | +++ | + | + |
| 042 | N.D. | N.D. | N.D. | N.D. | N.D. | N.D. | N.D. | N.D. |
| 043 | + | + | + | + | + | +++ | + | + |
| 044 | + | + | + | + | + | + | + | ++ |
| 045 | + | + | + | + | + | + | + | + |
| 046 | + | + | + | + | + | + | + | + |
| 047 | N.D. | N.D. | N.D. | N.D. | N.D. | N.D. | N.D. | N.D. |
| 048 | + | + | + | + | + | + | + | + |
| 049 | + | + | + | + | + | + | + | + |
| 050 | + | + | + | + | + | + | + | + |
| 051 | + | + | + | + | + | ++++ | + | ++++ |
| 052 | + | + | + | + | + | + | + | + |
| 053 | + | ++++ | + | + | ++++ | + | + | ++++ |
| 054 | + | + | + | + | + | + | + | + |
| 055 | + | ++++ | + | + | + | ++++ | + | ++++ |
| 056 | + | + | + | +++ | + | ++++ | + | ++++ |
| 057 | + | + | + | + | + | ++++ | + | ++ |
| 058 | + | + | + | + | + | ++++ | + | ++++ |
| 059 | + | ++++ | + | + | + | ++++ | + | ++++ |
| 060 | + | + | + | + | + | + | + | + |
| 061 | + | + | + | + | + | + | + | + |
| 062 | + | + | + | + | + | ++++ | + | + |
| 063 | N.D. | N.D. | N.D. | N.D. | N.D. | N.D. | N.D. | N.D. |
| 064 | N.D. | N.D. | N.D. | N.D. | N.D. | N.D. | N.D. | N.D. |

TABLE 3-continued

Anti-tumoral activity of compounds of formula
(I) on solid tumor cell lines (measured IC50).

| | Melanoma | | Glioblastoma | | Osteosarcoma | Ewing |
|---|---|---|---|---|---|---|
| Ex. | A375 | MEL_WO | U118 | U87_MG | U2OS | A4513 |
| 001 | + | + | + | + | + | + |
| 002 | + | + | + | + | + | + |
| 003 | ++++ | ++++ | + | + | + | ++++ |
| 004 | + | + | + | + | + | + |
| 005 | + | + | + | + | + | + |
| 006 | ++++ | ++++ | + | + | +++ | ++++ |
| 007 | ++++ | + | + | + | + | +++ |
| 008 | ++++ | ++ | + | + | + | + |
| 009 | + | + | + | + | + | + |
| 010 | ++++ | ++++ | + | + | + | + |
| 011 | + | + | + | + | + | + |
| 012 | N.D. | N.D. | N.D. | N.D. | N.D. | N.D. |
| 013 | + | + | + | + | + | +++ |
| 014 | + | + | + | + | + | ++ |
| 015 | + | + | + | + | + | +++ |
| 016 | + | + | + | + | + | + |
| 017 | + | + | + | + | + | + |
| 018 | ++++ | + | + | + | +++ | ++++ |
| 019 | N.D. | N.D. | N.D. | N.D. | N.D. | N.D. |
| 020 | + | + | + | + | + | ++++ |
| 021 | + | + | + | + | + | +++ |
| 022 | + | + | + | + | + | ++ |
| 023 | + | + | + | + | + | +++ |
| 024 | + | + | + | + | + | + |
| 025 | + | + | + | + | + | + |
| 026 | + | + | + | + | + | + |
| 027 | + | + | + | + | + | + |
| 028 | N.D. | N.D. | N.D. | N.D. | N.D. | N.D. |
| 029 | + | + | + | + | + | + |
| 030 | + | + | + | + | + | + |
| 031 | + | + | + | + | + | + |
| 032 | + | + | + | + | + | + |
| 033 | ++++ | ++++ | +++ | +++ | +++ | ++++ |
| 034 | + | + | + | + | + | + |
| 035 | + | + | + | + | + | + |
| 036 | ++++ | ++ | + | + | + | +++ |
| 037 | + | + | + | + | + | + |
| 038 | + | + | + | + | + | ++ |
| 039 | + | + | + | + | + | + |
| 040 | + | + | + | + | + | + |
| 041 | + | + | + | + | + | +++ |
| 042 | N.D. | N.D. | N.D. | N.D. | N.D. | N.D. |
| 043 | + | + | + | + | + | +++ |
| 044 | + | + | + | + | + | +++ |
| 045 | + | + | + | + | + | + |
| 046 | + | + | + | + | + | + |
| 047 | N.D. | N.D. | N.D. | N.D. | N.D. | N.D. |
| 048 | + | + | + | + | + | ++ |
| 049 | + | + | + | + | + | + |
| 050 | + | + | + | + | + | ++ |
| 051 | + | + | + | + | + | +++ |
| 052 | + | + | + | + | + | + |
| 053 | + | ++++ | + | + | + | ++++ |
| 054 | + | + | + | + | + | + |
| 055 | ++++ | +++ | + | + | ++++ | ++++ |
| 056 | ++++ | + | + | + | + | ++++ |
| 057 | +++ | + | + | + | + | ++ |
| 058 | ++++ | + | + | + | + | +++ |
| 059 | ++++ | +++ | + | + | + | ++++ |
| 060 | + | + | + | + | + | + |
| 061 | + | + | + | + | + | + |
| 062 | ++++ | + | + | + | + | +++ |
| 063 | N.D. | N.D. | N.D. | N.D. | N.D. | N.D. |
| 064 | N.D. | N.D. | N.D. | N.D. | N.D. | N.D. |

The IC50 given in table 3 above are expressed as:
++++: IC50 ≤ 100 nM
+++: 100 < IC50 ≤ 500 nM
++: 500 < IC50 ≤ 1000 nM
+: IC50 > 1000 nM
N.D.: Not Determined The inventors observed a very effective antiproliferative effect on the cell lines listed above by the class of compounds of formula (I) of the invention. The listed compounds in Tables 2 and 3 are well representing the class of compounds of formula (I).

C. Absence of Protein Kinase Inhibition

An in vitro kinase profiling was conducted in order to evidence the absence of protein kinase inhibition by the compounds of the invention.

DiscoveRx (Ambit Biosciences) has developed a high-throughput system (KINOMEscan™) for screening of compounds against large numbers of human kinases (456 kinases).

The compounds of the invention were screened at the concentration of 1 µM, and results for primary screen binding interactions were reported as percent control (% Ctrl), where lower numbers indicate stronger hits. DMSO is used as a negative control (100% Ctrl) while a high affinity compound is used as a positive control (0% Ctrl). % Ctrl is calculated as follow:

$$\left(\frac{\text{test compound signal} - \text{positive control signal}}{\text{negative control signal} - \text{positive control signal}}\right) \times 100$$

Selectivity Score or S-score is a quantitative measure of compound selectivity. It is calculated by dividing the number of kinases that compounds bind to by the total number of distinct kinases tested, excluding mutant variants. S(10)=(number of kinases with % Ctrl<10)/(number of kinases tested), S(1)=(number of kinases with % Ctrl<1)/(number of kinases tested).

By way of example, the S-scores of compounds 003, 006 and 033 are shown in Table below.

TABLE

S-score table for examples 003, 006 and 033 tested at 1 µM

| Cpd n° | S-score Type | Number of hits/number of kinases | S-score | Kinase targets |
|---|---|---|---|---|
| 003 | S1 | 1/456 | 0.002 | PDGFRB |
| | S10 | 4/456 | 0.009 | KIT, KIT V559D, KIT L576P |
| 006 | S1 | 0/456 | 0.000 | None |
| | S10 | 0/456 | 0.000 | |
| 033 | S1 | 0/456 | 0.000 | CDKL3 |
| | S10 | 1/456 | 0.002 | |

Compounds of the invention, and especially compounds 003, 006 and 033 as shown above, do not efficiently interact with the 456 kinases tested. The remaining little kinase inhibitory activity cannot explain the observed anti-proliferative action as compounds have no common kinase target enzymes (compounds 003 and 033) and still show anti-proliferative activity with no kinase inhibition (compounds 006).

The invention claimed is:
1. A compound of Formula (I)

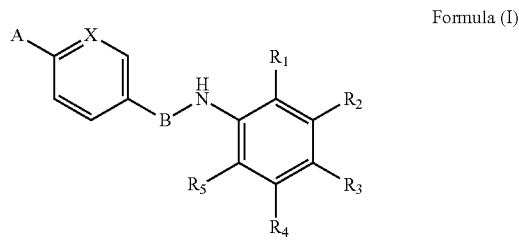

Formula (I)

or a pharmaceutically acceptable salt thereof, wherein:
$R_1$, $R_2$, and $R_5$ are each independently selected from hydrogen; heterocycle; cyano; —$CF_3$; —NRR'; —OH; halogen; alkyl group optionally substituted by one or more group selected from heterocycle, —NRR', —OR, or a solubilizing group; alkoxy group optionally substituted by one or more group selected from heterocycle, —NRR', —OR, or a solubilizing group; —CO—NRR'; —$SO_2$—NRR'; —NR—CO—R'; or —NR—$SO_2R'$;
wherein R and R' are each independently selected from hydrogen, cycloalkyl, heterocycle, solubilizing group, or alkyl group optionally substituted by one or more group selected from OR", NR"R'", NR"COR'", or solubilizing group; wherein R" and R'" are each independently selected from hydrogen, alkyl, or cycloalkyl;
$R_3$ is a hydrogen;
$R_4$ is selected from heterocycle; cyano; —OH; alkyl group optionally substituted by one or more group selected from heterocycle, —NRR', —OR, or a solubilizing group; alkoxy group optionally substituted by one or more group selected from heterocycle, —NRR', —OR, or a solubilizing group; or —CO—NRR';
wherein R and R' are each independently selected from hydrogen, cycloalkyl, heterocycle, solubilizing group, or alkyl group optionally substituted by one or more group selected from OR", NR"R'", NR"COR'", or solubilizing group; wherein R" and R'" are each independently selected from hydrogen, alkyl, or cycloalkyl;
A is a heterocycle group selected from triazolyl, oxotriazolyl, imidazolyl, oxoimidazolidinyl, pyrazolyl, pyridyl, oxopyridyl, thiazolyl or oxopyrrolidinyl; optionally substituted by one or more group selected from halogen, alkyl, aryl, hydroxyl, alkoxy, nitro, thiol, heterocycloalkyl, heteroaryl, cyano, cycloalkyl, a solubilizing group, —NRR', -alkyl-NRR'; —NR—CO—R', -alkyl-NR—CO—R', —CONRR', or —$SO_2NRR'$ group; wherein R and R' are each independently selected from hydrogen, alkyl, cycloalkyl, aryl, heterocycloalkyl, or heteroaryl groups;
B is a five-member ring heteroaryl group;
X is N or C—$R_6$, wherein $R_6$ is selected from hydrogen, cyano, $CF_3$, alkyl, or alkoxy;
wherein each solubilizing group independently is selected from
(i) —C(O)OR, —OH, —S(O)$_2$OR, —P(O)(OR)(OR')OH, or —NRR'; wherein R and R' are each independently selected from hydrogen; $C_1$-$C_{10}$ alkyl optionally substituted with at least one heteroatom selected from F, Cl, Br, I, O, or N; aryl; or heteroaryl; or (ii) —N—(CH$_2$)$_z$R, —N—(CH$_2$)$_z$—C(O)R, —N—(CH$_2$)$_z$—C(O)OR, —N—(CH$_2$)$_z$—S(O)$_2$R, —N—(CH$_2$)$_z$—S(O)$_2$OR, —N—(CH$_2$)$_z$—C(O)NRR';
wherein z is an integer ranging from 0 to 6; and R and R' are each independently selected from hydrogen; C$_1$-C$_{10}$ alkyl optionally substituted with at least one heteroatom selected from F, Cl, Br, I, O, or N; C$_1$-C$_{10}$ alkoxy; aryl; or heteroaryl; or (iii) any one of the following formulae:

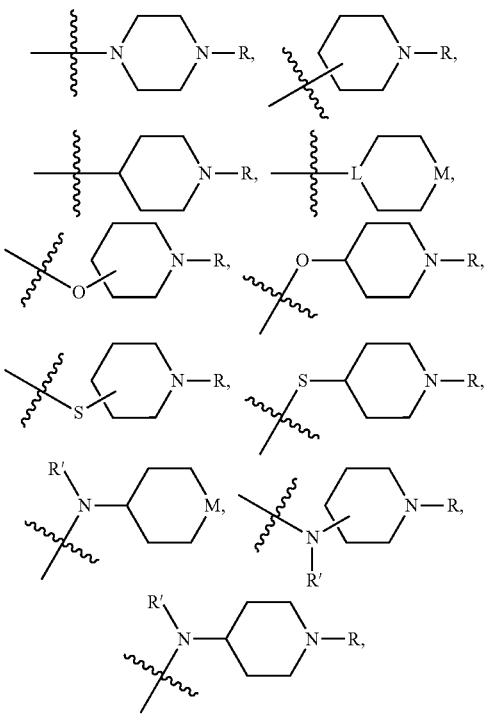

wherein:
L is selected from CH and N;
M is selected from —CH(R)—, —CH$_2$—, —O—, —S—, —NH—, —N(—(CH$_2$)$_z$—R)—, —N(—(CH$_2$)$_z$—C(O)R)—, —N(—(CH$_2$)$_z$—C(O)OR)—, —N(—(CH$_2$)$_z$—S(O)$_2$R)—, —N(—(CH$_2$)$_z$—S(O)$_2$OR)—, or —N(—(CH$_2$)$_z$—C(O)NRR')—;
z is an integer ranging from 0 to 6;
R and R' are each independently selected from hydrogen; aryl; heteroaryl; C$_1$-C$_{10}$ alkyl optionally substituted with at least one heteroatom selected from F, Cl, Br, I, O, or N; C$_1$-C$_{10}$ alkoxy; or NRR' wherein R and R' are each independently selected from hydrogen or C$_1$-C$_{10}$ alkyl optionally substituted with at least one heteroatom selected from F, Cl, Br, I, O, or N;
provided that L and M are not both simultaneously CH and CH$_2$, respectively;
provided that
B is not optionally substituted triazolyl; and
if B is thiazolyl, then A is not optionally substituted imidazolyl, or optionally substituted triazolyl.

2. The compound according to claim 1 or a pharmaceutically acceptable salt thereof, wherein X is CH and A is 2-oxoimidazolidinyl or pyrazolyl group.

3. The compound according to claim 1 of Formula (II):

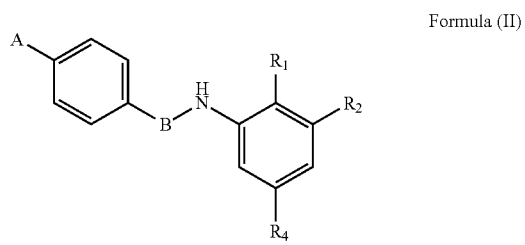

Formula (II)

or a pharmaceutically acceptable salt thereof, wherein
R$_1$ and R$_2$ are each independently selected from hydrogen; heterocycles; cyano; —CF$_3$; —NRR'; —OH; halogen; alkyl group optionally substituted by one or more group selected from heterocycle, NRR', OR, or a solubilizing group; alkoxy group optionally substituted by one or more group selected from heterocycle, NRR', OR, or a solubilizing group; —CO—NRR'; —SO$_2$—NRR'; —NR—CO—R', and —NR—SO$_2$R'; wherein R and R' are each independently selected from hydrogen, cycloalkyl, heterocycle, solubilizing group, or alkyl group optionally substituted by one or more group selected from OR", NR"R", NR"COR"'; or solubilizing group; wherein R" and R"' are each independently selected from hydrogen, alkyl, or cycloalkyl;

R$_4$ is selected from heterocycle; cyano; —OH; alkyl group optionally substituted by one or more group selected from heterocycle, —NRR', —OR, or a solubilizing group; alkoxy group optionally substituted by one or more group selected from heterocycle, —NRR', —OR, or a solubilizing group; or —CO—NRR';

wherein R and R' are each independently selected from hydrogen, cycloalkyl, heterocycle, solubilizing group, or alkyl group optionally substituted by one or more group selected from OR", NR"R"', NR"COR"', or solubilizing group; wherein R" and R"' are each independently selected from hydrogen, alkyl, or cycloalkyl;

B is a five-member ring heteroaryl group;

A is a heterocycle group selected from triazolyl, oxotriazolyl, imidazolyl, oxoimidazolidinyl, pyrazolyl, pyridyl, oxopyridyl, thiazolyl, or oxopyrrolidinyl; optionally substituted by one or more group selected from halogen, alkyl, aryl, hydroxyl, alkoxy, nitro, thiol, heterocycloalkyl, heteroaryl, cyano, cycloalkyl, a solubilizing group, —NRR', -alkyl-NRR'; —NR—CO—R', -alkyl-NR—CO—R', —CONRR', or —SO$_2$NRR' group; wherein R and R' are each independently selected from hydrogen, alkyl, cycloalkyl, aryl, heterocycloalkyl, or heteroaryl groups;

wherein each solubilizing group independently is as described in claim 1;

provided that
B is not optionally substituted triazolyl; and
if B is thiazolyl, then A is not optionally substituted imidazolyl or optionally substituted triazolyl.

4. The compound according to claim 1 of Formula (III):

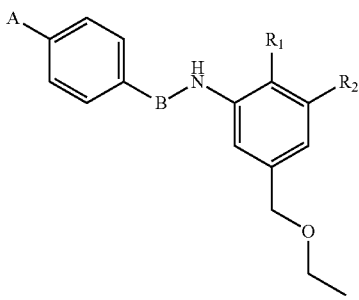

Formula (III)

or a pharmaceutically acceptable salt thereof, wherein
R₁ and R2 are each independently selected from hydrogen; heterocycles; cyano; —CF₃; —NRR'; —OH; halogen; alkyl group optionally substituted by one or more group selected from heterocycle, NRR', OR, or a solubilizing group; alkoxy group optionally substituted by one of more group selected from heterocycle, NRR', OR, or a solubilizing group; —CO—NRR'; —SO₂—NRR'; —NR—CO—R'; and —NR—SO₂R'; wherein R and R' are each independently selected from hydrogen, cycloalkyl, heterocycle, solubilizing group, or alkyl group optionally substituted by one or more group selected from OR", NR"R'", NR"COR'", or solubilizing group; wherein R" and R'" are each independently selected from hydrogen, alkyl, or cycloalkyl;
B is a five-member ring heteroaryl group;
A is a heterocycle group selected from triazolyl, oxotriazolyl, imidazolyl, oxoimidazolidinyl, pyrazolyl, pyridyl, oxopyridyl, thiazolyl, or oxopyrrolidinyl; optionally substituted by one or more group selected from halogen, alkyl, aryl, hydroxyl, alkoxy, nitro, thiol, heterocycloalkyl, heteroaryl, cyano, cycloalkyl, a solubilizing group, —NRR', -alkyl-NRR'; —NR—CO—R', -alkyl-NR—CO—R', —CONRR', or —SO₂NRR' group; wherein R and R' are each independently selected from hydrogen, alkyl, cycloalkyl, aryl, heterocycloalkyl, or heteroaryl groups;
wherein each solubilizing group independently is as described in claim 1;
provided that
B is not optionally substituted triazolyl; and
if B is thiazolyl, then A is not optionally substituted imidazolyl or optionally substituted triazolyl.

5. The compound according to claim 1 or a pharmaceutically acceptable salt thereof, wherein R₁ is methyl, R2, R₃ and R₅ are hydrogen and R4 is —CH₂OC₂H₅.

6. The compound according to claim 1, or a pharmaceutically acceptable salt thereof, selected from
(5-Methoxy-2-methyl-phenyl)-[5-(6-pyrazol-1-yl-pyridin-3-yl)-oxazol-2-yl]-amine;
(5-Ethoxymethyl-2-methyl-phenyl)-[5-(3-methoxy-4-pyrazol-1-yl-phenyl)-oxazol-2-yl]-amine;
1-{4-[2-(5-Ethoxymethyl-(2-methyl-phenylamino))-thiazol-4-yl]-phenyl}-imidazolidin-2-one;
(5-Ethoxymethyl-2-methyl-phenyl)-[5-(4-pyrazol-1-yl-phenyl)-thiazol-2-yl]-amine;
4-Methyl-N-(2-morpholin-4-yl-ethyl)-3-[5-(4-pyrazol-1-yl-phenyl)-oxazol-2-ylamino]-benzamide;
1-{4-[2-(5-Ethoxymethyl-(2-methyl-phenylamino))-oxazol-5-yl]-phenyl}-imidazolidin-2-one;
(5-Ethoxymethyl-2-methyl-phenyl)-[5-(6-pyrazol-1-yl-pyridin-3-yl)-oxazol-2-yl]-amine;
1-{4-[5-(5-Ethoxymethyl-(2-methyl-phenylamino))-[1,3,4]oxadiazol-2-yl]-phenyl}-imidazolidin-2-one;
(5-Ethoxymethyl-2-methyl-phenyl)-[5-(4-pyrazol-1-yl-phenyl)-[1,3,4]oxadiazol-2-yl]-amine;
1-{4-[5-(5-Ethoxymethyl-(2-methyl-phenylamino))-[1,2,4]thiadiazol-3-yl]-phenyl}-imidazolidin-2-one;
(5-Methoxy-2-methyl-phenyl)-[5-(4-pyrazol-1-yl-phenyl)-thiazol-2-yl]-amine;
1-{4-[2-(5-Methoxy-2-methyl-phenylamino)-thiazol-5-yl]-phenyl}-imidazolidin-2-one;
1-{4-[2-(5-Ethoxymethyl-(2-methyl-phenylamino))-thiazol-5-yl]-phenyl}-imidazolidin-2-one;
(5-Ethoxymethyl-2-methyl-phenyl)-[4-(4-pyrazol-1-yl-phenyl)-thiazol-2-yl]-amine;
{4-Methyl-3-[4-(4-pyrazol-1-yl-phenyl)-thiazol-2-ylamino]-phenyl}-methanol;
1-{4-[2-(3-Ethoxymethyl-(5-methyl-phenylamino))-thiazol-4-yl]-phenyl}-imidazolidin-2-one;
1-{4-[2-(3-Ethoxymethyl-(5-methyl-phenylamino))-oxazol-5-yl]-phenyl}-imidazolidin-2-one;
(3-Ethoxymethyl-phenyl)-[5-(4-pyrazol-1-yl-phenyl)-oxazol-2-yl]-amine;
(3-Ethoxymethyl-5-methyl-phenyl)-[5-(4-pyrazol-1-yl-phenyl)-oxazol-2-yl]-amine;
(3,5-Bis-(ethoxymethyl)-phenyl)-[5-(4-pyrazol-1-yl-phenyl)-oxazol-2-yl]-amine;
(5-Methoxy-2-methyl-phenyl)-[5-(4-pyrazol-1-yl-phenyl)-oxazol-2-yl]-amine;
[5-(2-Amino-ethoxymethyl)-2-methyl-phenyl]-[5-(4-pyrazol-1-yl-phenyl)-oxazol-2-yl]-amine;
N-(2-{4-Methyl-3-[5-(4-pyrazol-1-yl-phenyl)-oxazol-2-ylamino]-benzyloxy}-ethyl)-acetamide;
2-{4-Methyl-3-[5-(4-pyrazol-1-yl-phenyl)-oxazol-2-ylamino]-benzyloxy}-ethanol;
{4-Methyl-3-[5-(4-pyrazol-1-yl-phenyl)-oxazol-2-ylamino]-phenyl}-methanol;
{2-Methyl-5-[(2-morpholin-4-yl-ethylamino)-methyl]-phenyl}-[5-(4-pyrazol-1-yl-phenyl)-oxazol-2-yl]-amine;
[2-Methyl-5-(2-morpholin-4-yl-ethoxy)-phenyl]-[5-(4-pyrazol-1-yl-phenyl)-oxazol-2-yl]-amine;
[5-(2-Dimethylamino-ethoxy)-2-methyl-phenyl]-[5-(4-pyrazol-1-yl-phenyl)-oxazol-2-yl]-amine;
4,N-Dimethyl-3-[5-(4-pyrazol-1-yl-phenyl)-oxazol-2-ylamino]-benzamide;
4-Methyl-N-[2-(4-methyl-piperazin-1-yl)-ethyl]-3-[5-(4-pyrazol-1-yl-phenyl)-oxazol-2-ylamino]-benzamide;
(5-Ethoxymethyl-2-methyl-phenyl)-[5-(4-pyrazol-1-yl-phenyl)-oxazol-2-yl]-amine;
(5-Ethoxymethyl-2-methyl-phenyl)-[5-(4-[1,2,4]triazol-1-yl-phenyl)-oxazol-2-yl]-amine;
(5-Ethoxymethyl-2-methyl-phenyl)-[5-(4-[1,2,3]triazol-1-yl-phenyl)-oxazol-2-yl]-amine;
(5-Ethoxymethyl-2-methyl-phenyl)-[5-(4-[1,2,3]triazol-2-yl-phenyl)-oxazol-2-yl]-amine;
(5-Ethoxymethyl-2-methyl-phenyl)-[5-(4-imidazol-1-yl-phenyl)-oxazol-2-yl]-amine;
(5-Ethoxymethyl-2-methyl-phenyl)-[5-(4-thiazol-2-yl-phenyl)-oxazol-2-yl]-amine;
(5-Ethoxymethyl-2-methyl-phenyl)-{5-[4-(3-methyl-pyrazol-1-yl)-phenyl]-oxazol-2-yl}-amine;
(5-Ethoxymethyl-2-methyl-phenyl)-{5-[4-(4-methyl-pyrazol-1-yl)-phenyl]-oxazol-2-yl}-amine;
(5-Ethoxymethyl-2-methyl-phenyl)-{5-[4-(5-methyl-pyrazol-1-yl)-phenyl]-oxazol-2-yl}-amine;

(5-Ethoxymethyl-2-methyl-phenyl)-{5-[4-(3-methoxy-pyrazol-1-yl)-phenyl]-oxazol-2-yl}-amine;

2-{4-[2-(5-Ethoxymethyl-(2-methyl-phenylamino))-oxazol-5-yl]-phenyl}-2,4-dihydro-[1,2,4]triazol-3-one;

1-{4-[2-(5-Ethoxymethyl-(2-methyl-phenylamino))-oxazol-5-yl]-phenyl}-3-methyl-imidazolidin-2-one;

1-(2-Amino-ethyl)-3-{4-[2-(5-ethoxymethyl-(2-methyl-phenylamino))-oxazol-5-yl]-phenyl}-imidazolidin-2-one;

N-[2-(3-{4-[2-(5-Ethoxymethyl-(2-methyl-phenylamino))-oxazol-5-yl]-phenyl}-2-oxo-imidolidin-1-yl)-ethyl]-acetamide;

1-{4-[2-(5-Ethoxymethyl-(2-methyl-phenylamino))-oxazol-5-yl]-phenyl}-pyrrolidin-2-one;

(5-Ethoxymethyl-2-methyl-phenyl)-[5-(4-pyridin-2-yl-phenyl)-oxazol-2-yl]-amine;

1-{4-[2-(5-Ethoxymethyl-(2-methyl-phenylamino))-oxazol-5-yl]-phenyl}-1H-pyridin-2-one;

3-{4-[2-(5-Ethoxymethyl-(2-methyl-phenylamino))-oxazol-5-yl]-phenyl}-1H-pyridin-2-one;

(R)-1-(4-(2-((5-(ethoxymethyl)-2-methylphenyl)amino)oxazol-5-yl)phenyl)-5-methylimidazolidin-2-one;

4-(4-(2-((5-(ethoxymethyl)-2-methylphenyl)amino)oxazol-5-yl)phenyl)-5-methyl-2,4-dihydro-3H-1,2,4-triazol-3-one;

1-(4-(2-((3,5-bis(ethoxymethyl)phenyl)amino)oxazol-5-yl)phenyl)imidazolidin-2-one;

1-(4-(2-((5-(ethoxymethyl)-2-methylphenyl)amino)oxazol-5-yl)phenyl)-3-(2-methoxyethyl)imidazolidin-2-one;

1-(5-(2-((5-(ethoxymethyl)-2-methylphenyl)amino)oxazol-5-yl)pyridin-2-yl)imidazolidin-2-one;

1-(4-(2-((3-(ethoxymethyl)-5-(2-methoxyethoxy)phenyl)amino)oxazol-5-yl)phenyl)imidazolidin-2-one;

5-(4-(1H-pyrazol-5-yl)phenyl)-N-(5-(ethoxymethyl)-2-methylphenyl)oxazol-2-amine;

(R)-1-(5-(2-((5-(ethoxymethyl)-2-methylphenyl)amino)oxazol-5-yl)pyridin-2-yl)-5-methylimidazolidin-2-one;

1-(4-(2-((3-(ethoxymethyl)-5-(2-hydroxyethoxy)phenyl)amino)oxazol-5-yl)phenyl)imidazolidin-2-one;

5-(4-(1H-pyrazol-4-yl)phenyl)-N-(5-(ethoxymethyl)-2-methylphenyl)oxazol-2-amine;

N-(5-(ethoxymethyl)-2-methylphenyl)-5-(4-(1-methyl-1H-pyrazol-5-yl)phenyl)oxazol-2-amine;

4-(6-(1H-pyrazol-1-yl)pyridin-3-yl)-N-(5-(ethoxymethyl)-2-methylphenyl)thiazol-2-amine;

1-(4-(2-((3-(ethoxymethyl)phenyl)amino)oxazol-5-yl)phenyl)imidazolidin-2-one; and 1-(4-(2-((3-(ethoxymethyl)phenyl)amino)thiazol-4-yl)phenyl)imidazolidin-2-one.

7. A pharmaceutical composition comprising a compound according to claim 1, or a pharmaceutically acceptable salt thereof, and at least one pharmaceutically acceptable excipient, carrier, or both.

8. The pharmaceutical composition according to claim 7, wherein the compound according to claim 1, or the pharmaceutically acceptable salt thereof, is the sole active pharmaceutical ingredient in the pharmaceutical composition.

9. The pharmaceutical composition according to claim 7, wherein the pharmaceutical composition further comprises an active pharmaceutical ingredient other than the compound according to claim 1, or the pharmaceutically acceptable salt thereof.

10. The pharmaceutical composition according to claim 7, wherein the composition is a medicament.

11. A method for treating hematological disorders, proliferative disorders, or both, in a subject in need thereof, the method comprising a step of topical administration to the subject of a composition comprising a compound according to claim 1, or a pharmaceutically acceptable salt thereof.

12. The method according to claim 11, wherein the hematological disorder is selected from lymphoma; leukemia; multiple myeloma (MM); myelodysplatic syndrome (MDS); or myelodysplasia with myelofibrosis.

13. The method according to claim 11, wherein the proliferative disorder is cancer.

14. The method according to claim 11, wherein the composition further comprises an active pharmaceutical ingredient other than the compound according to claim 1, or the pharmaceutically acceptable salt thereof.

15. The method according to claim 11, wherein the hematological disorder is a leukemia selected from Acute Myeloid Leukemia (AML), Acute Lymphoblastic Leukemia (ALL), Chronic Lymphoid Leukemia (CLL), or Chronic Myeloid Leukemia (CML).

16. The method according to claim 11, wherein the proliferative disorder is cancer selected from head and neck cancer, melanoma, kidney carcinoma, stomach carcinoma, liver carcinoma, colorectal carcinoma, pancreas carcinoma, lung carcinoma, neuronal carcinoma, glioblastoma multiforme, osteosarcoma, Ewing sarcoma, breast carcinoma, ovary carcinoma, or prostate carcinoma.

17. The method according to claim 11, wherein the composition comprises the compound according to claim 1, or the pharmaceutically acceptable salt thereof, and at least one pharmaceutically acceptable excipient, carrier, or both.

18. The method according to claim 11, wherein the compound according to claim 1, or the pharmaceutically acceptable salt thereof, is the sole active pharmaceutical ingredient in the composition.

19. The method according to claim 11, wherein the composition further comprises an active pharmaceutical ingredient other than the compound according to claim 1, or the pharmaceutically acceptable salt thereof; and wherein the method comprises a step of administration of the composition for sequential, simultaneous or separate treatment of the hematological disorder, the proliferative disorder, or both.

* * * * *